(12) United States Patent
Butler et al.

(10) Patent No.: US 8,691,164 B2
(45) Date of Patent: Apr. 8, 2014

(54) CELL SORTING SYSTEM AND METHODS

(75) Inventors: William Frank Butler, La Jolla, CA (US); Haichuan Zhang, San Diego, CA (US); Philippe Marchand, Poway, CA (US); Keunho Ahn, La Jolla, CA (US); Yi Zhang, San Diego, CA (US); John Francis, San Diego, CA (US); Benjamin Lai, San Diego, CA (US); Eugene Tu, San Diego, CA (US)

(73) Assignee: Celula, Inc., San Diego, CA (US)

( * ) Notice: Subject to any disclaimer, the term of this patent is extended or adjusted under 35 U.S.C. 154(b) by 1044 days.

(21) Appl. No.: 11/781,848

(22) Filed: Jul. 23, 2007

(65) Prior Publication Data
US 2008/0261295 A1    Oct. 23, 2008

Related U.S. Application Data

(60) Provisional application No. 60/925,563, filed on Apr. 20, 2007.

(51) Int. Cl.
*C12M 1/36* (2006.01)

(52) U.S. Cl.
USPC ........... 422/505; 422/502; 422/503; 422/504; 422/509; 435/286.5; 435/287.1; 436/180

(58) Field of Classification Search
USPC ............. 435/286.5, 287.1; 436/180; 422/100, 422/502–505, 509
See application file for complete search history.

(56) References Cited

U.S. PATENT DOCUMENTS

| | | | |
|---|---|---|---|
| 4,756,427 A | 7/1988 | Göhde et al. | |
| 4,893,886 A | 1/1990 | Ashkin et al. | |
| 5,726,404 A | 3/1998 | Brody | |
| 5,876,675 A | 3/1999 | Kennedy | |
| 5,994,056 A | 11/1999 | Higuchi | |
| 6,048,498 A | 4/2000 | Kennedy | |
| 6,171,785 B1 | 1/2001 | Higuchi | |
| 6,174,675 B1 | 1/2001 | Chow et al. | |
| 6,251,343 B1 | 6/2001 | Dubrow et al. | |

(Continued)

FOREIGN PATENT DOCUMENTS

| | | |
|---|---|---|
| WO | WO 2007/009983 A1 | 1/2007 |
| WO | WO 2007/081385 A2 | 7/2007 |
| WO | WO 2007/081386 A2 | 7/2007 |
| WO | WO 2007/140015 A2 | 12/2007 |

OTHER PUBLICATIONS

Buican, et al., "Automated Single-Cell Manipulation and Sorting by Light Trapping", Applied Optics, v. 26, n. 24, Dec. 15, 1987, 5311-5316.

(Continued)

*Primary Examiner* — Shogo Sasaki
(74) *Attorney, Agent, or Firm* — David B. Murphy; O'Melveny & Myers

(57) ABSTRACT

Apparatus and Methods are provided for a microfabricated fluorescence activated cell sorter based on a switch for rapid, active control of cell routing through a microfluidic channel network. This sorter enables low-stress, highly efficient sorting of populations of small numbers of cells (i.e., 1000-100,000 cells). The invention includes packaging of the microfluidic channel network in a self-contained plastic cartridge that enables microfluidic channel network to macro-scale instrument interconnect, in a sterile, disposable format. Optical and/or fluidic switching forces are used alone or in combination to effect switching.

17 Claims, 51 Drawing Sheets b) Two external valve operation and response.

(56) References Cited

U.S. PATENT DOCUMENTS

| | | | |
|---|---|---|---|
| 6,321,791 | B1 | 11/2001 | Chow |
| 6,432,720 | B2 | 8/2002 | Chow |
| 6,488,895 | B1 | 12/2002 | Kennedy |
| 6,506,609 | B1 | 1/2003 | Wada et al. |
| 6,524,830 | B2 | 2/2003 | Kopf-Sill |
| 6,534,013 | B1 | 3/2003 | Kennedy |
| 6,592,821 | B1 | 7/2003 | Wada et al. |
| 6,632,619 | B1 * | 10/2003 | Harrison et al. ............ 435/7.2 |
| 6,670,153 | B2 | 12/2003 | Stern |
| 6,744,038 | B2 | 6/2004 | Wang et al. |
| 6,778,724 | B2 | 8/2004 | Wang et al. |
| 6,783,647 | B2 * | 8/2004 | Culbertson et al. ........... 204/453 |
| 6,784,420 | B2 | 8/2004 | Wang et al. |
| 6,808,075 | B2 | 10/2004 | Böhm et al. |
| 6,808,882 | B2 | 10/2004 | Griffiths et al. |
| 6,814,934 | B1 | 11/2004 | Higuchi |
| 6,815,664 | B2 | 11/2004 | Wang et al. |
| 6,833,542 | B2 | 12/2004 | Wang et al. |
| 6,915,679 | B2 | 7/2005 | Chien et al. |
| 6,936,811 | B2 | 8/2005 | Kibar |
| 7,068,874 | B2 | 6/2006 | Wang et al. |
| 7,091,048 | B2 | 8/2006 | Parce et al. |
| 7,129,091 | B2 | 10/2006 | Ismagilov et al. |
| 7,138,269 | B2 | 11/2006 | Blankenstein |
| 7,153,673 | B2 | 12/2006 | Stern |
| 7,584,857 | B2 | 9/2009 | Böhm et al. |
| 7,745,221 | B2 * | 6/2010 | Butler et al. .................... 436/63 |
| 2003/0159999 | A1 * | 8/2003 | Oakey et al. ................. 210/695 |
| 2005/0109410 | A1 * | 5/2005 | Gilbert et al. ................ 137/827 |
| 2005/0164372 | A1 | 7/2005 | Kibar |
| 2005/0172476 | A1 | 8/2005 | Stone et al. |
| 2005/0207940 | A1 * | 9/2005 | Butler et al. .................... 422/73 |
| 2006/0060767 | A1 | 3/2006 | Wang et al. |
| 2006/0078888 | A1 | 4/2006 | Griffiths et al. |
| 2006/0094119 | A1 | 5/2006 | Ismagilov et al. |
| 2006/0169642 | A1 * | 8/2006 | Oakey et al. ................. 210/695 |
| 2007/0003442 | A1 | 1/2007 | Link et al. |
| 2007/0077572 | A1 | 4/2007 | Tawfik et al. |
| 2007/0172954 | A1 | 7/2007 | Ismagilov et al. |
| 2008/0003142 | A1 | 1/2008 | Link et al. |
| 2008/0213821 | A1 | 9/2008 | Liu et al. |

OTHER PUBLICATIONS

Dittrich, et al., "An Integrated Microfluidic System for Reaction, High-Sensitivity Detection, and Sorting of Fluorescent Cells and Particles", Analytical Chemistry, v. 75, n. 21, Nov. 1, 2003, 5767-5774.

Durr, et al., "Microdevices for Manipulation and Accumulation of Micro- and Nanoparticles by Dielectrophoresis", Electrophoresis, v. 24, 2003, 722-731.

Fiedler, et al., "Dielectrophoretic Sorting of Particles and Cells in a Microsystem", Analytical Chemistry, v. 70, n. 9, May 1, 1998, 1909-1915.

Fu, et al., "A Microfabricated Fluorescence-Activated Cell Sorter", Nature Biotechnology, v. 17, Nov. 1999, 1109-1111.

Fu, et al., "An Integrated Microfabricated and Cell Sorter", Analytical Chemistry, v. 74, n. 11, Jun. 1, 2002, 2451-2457.

Huang, et al., "Electric Manipulation of Bioparticles and Macromolecules on Microfabricated Electrodes", Analytical Chemistry, v. 73, n. 7, Apr. 1, 2001, 1549-1559.

Kopp, et al., "Chemical Amplification: Continuous Flow PCR on a Chip", Science, v. 280, May 15, 1998, 1046-1048.

Li, et al., "Transport, Manipulation, and Reaction of Biological Cells On-Chip Using Electrokinetic Effects", Analytical Chemistry, v. 69, n. 8, Apr. 15, 1997, 1564-1568.

Shapiro, et al., *Practical Flow Cytometry*, Chapter 4—How Flow Cytometers Work, pp. 101-273; Chapter 6—Flow Sorting, pp. 257-271, Wiley-Liss, New York, 2003.

Wolff, et al., "Integrating Advanced Functionality in a Microfabricated High-Throughput Fluorescent-Activated Cell Sorter", Lab Chip, v. 3, 2003, 22-27.

Chabert, et al., "Automated Microdroplet Platform for Sample Manipulation and Polymerase Chain Reaction", Anal. Chem., vol. 78, No. 22, Nov. 15, 2006, 7722-7728.

He et al., "Selective Encapsulation of Single Cells and Subcellular Organelles Into Picoliter- and Femtoliter-Volume Droplets", Anal. Chem., vol. 77, No. 6, Mar. 15, 2005, 1539-1544.

Hong, et al., "A Nanoliter-Scale Nucleic Acid Processor With Parallel Architecture", Nature Biotechnology, vol. 22, No. 4, Apr. 2004, 435-439.

Link, et al., "Electric Control of Droplets in Microfluidic Devices", Angew. Chem. Int. Ed., vol. 45, 2006, 2556-2560.

Liu, et al., "A Nanoliter Rotary Device for Polymerase Chain Reaction", Electrophoresis, vol. 23, 2002, 1531-1536.

Marcus, "Single Mammalian Cell Gene Expression Analysis Using Microfluidics", Thesis in Partial Fulfillment of the Requirements for the Degree of Doctor of Philosophy, California Institute of Technology, Pasadena, CA, 2006 (Defended Apr. 11, 2006), i-164.

Martin, et al, "Generation of Larger Numbers of Separated Microbial Populations by Cultivation in Segmented-Flow Microdevices", Lab Chip, vol. 3, 2003, 202-207.

Song, et al., "Droplet-Based Microfluidics, Reactions in Droplets in Microfludic Channels", Angew. Chem. Int. Ed., vol. 45, 2006, 7336-7356.

Sugiara, et al., "Size Control of Calcium Alginate Beads Containing Living Cells Using Micro-Nozzle Array", Biomaterials, vol. 26, 2005, 3327-3331.

International Search Report for PCT/US2008/060015 dated May 30, 2011.

Doig et al., "The Use of Microscale Processing Technologies for Quantitification of Biocatalytic Baeyer-Villiger Oxidation Kinetics", Biology and Bioengineering, vol. 80, No. 1, Oct. 5, 2002, pp. 42-49.

Marcus, et al., "Parallel Picoliter RT-PCR Assays Using Microfluidics", Analytical Chemistry, vol. 78, No. 3, Feb. 1, 2006, pp. 956-958 and supporting information pp. S-1 to S-2.

Shiku, et al., "Respiration Activity of Single Bovine Embryos Entrapped in a Cone-Shaped Microwell Monitored by Scanning Electrochemical Microscopy", Analytica Chimica Acta, vol. 522, 2004, pp. 51-58.

Yamamura, et al., "Single-Cell Microarray for Analyzing Cellular Response", Analytical Chemistry, vol. 77, No. 24, Dec. 15, 2005, pp. 8050-8056 and supporting information pp. S-1 to S-3.

* cited by examiner

Sheath flow: 50/50 splitting of cells

Skewed particle flow via differential sheath flow rate
Fluorescence-Negative/Optical Switch not triggered

Skewed particle flow via differential sheath flow rate
Fluorescence-Positive/Optical Switch triggered

Skewed particle flow via differential channel width
Fluorescence-Positive/Optical Switch triggered Higher flow rate
Fluorescence-Negative
Non-target Cells Lower flow rate
Fluorescence-Positve
Target Cells A.) 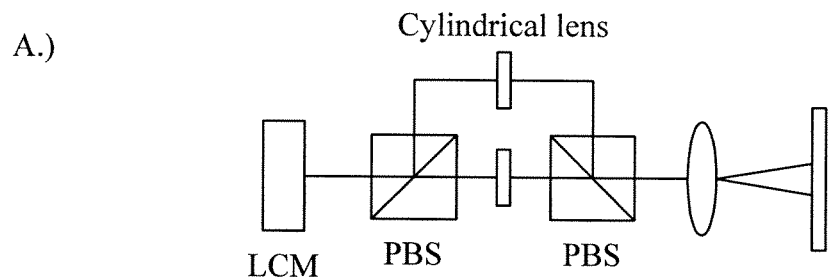
B.) 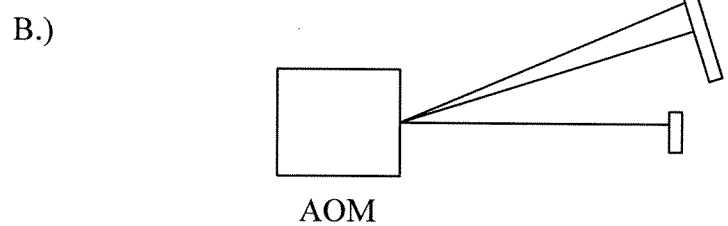
C.) 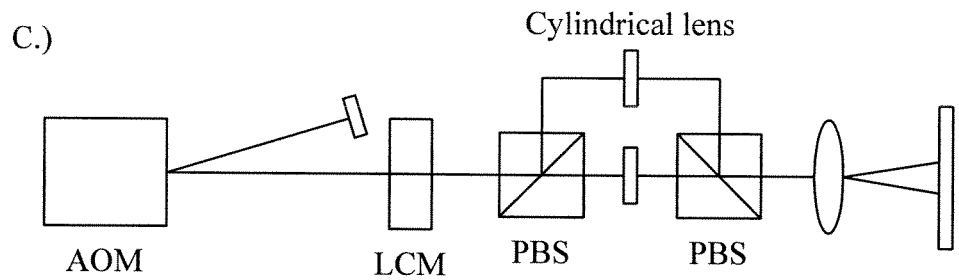
FIG. 8

Method for timing and triggering optical switch laser
- Single laser and separate detectors used to detect particle and trigger switch laser

Detector Arrangement:
Sort parameter Positive/Optical Switch triggered

Method for timing and triggering optical switch laser
- Separate lasers and detectors used to detect particle, determine particle flow rate and trigger switch laser

Detector Arrangement:
Sort parameter negative/Optical Switch not triggered

Junction where sheath buffer flowing from the sides, surrounds and focuses the sample into a single file. This creates a sample core flowing in the center of the main channel.

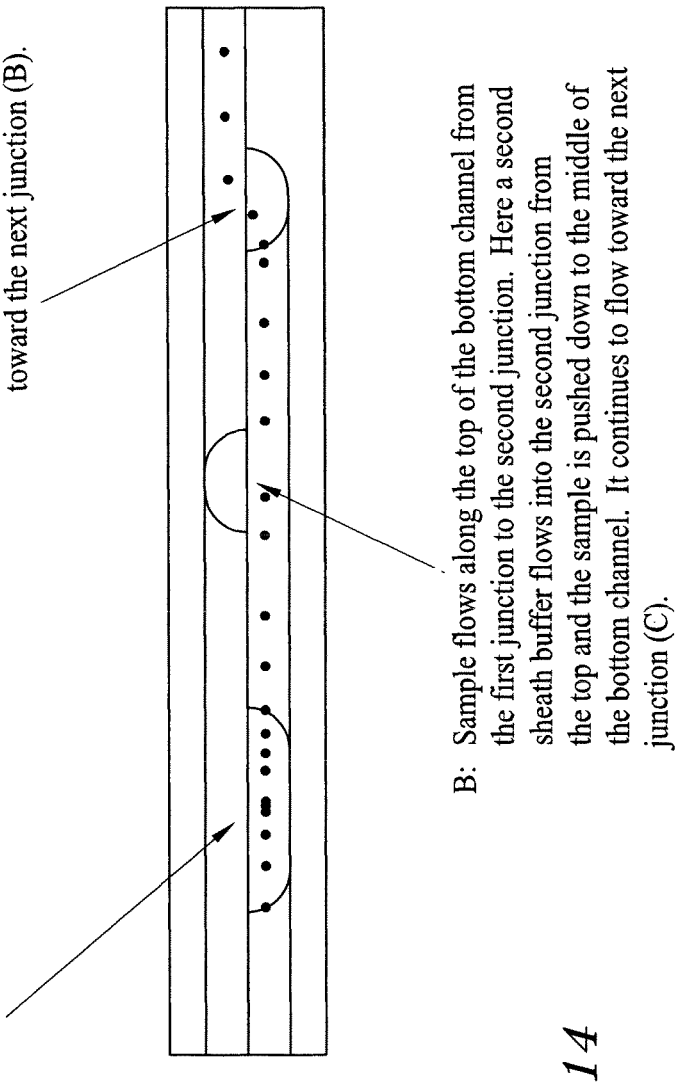

FIG. 14

A: Sample flows from top, into the junction and down into the channel in the bottom where the side sheath buffer flows into the junction from the sides. The sample is slightly focused and pushed to the top wall of the bottom channel as it continues to flow toward the next junction (B).

B: Sample flows along the top of the bottom channel from the first junction to the second junction. Here a second sheath buffer flows into the second junction from the top and the sample is pushed down to the middle of the bottom channel. It continues to flow toward the next junction (C).

C: Sample flows along the middle of the bottom channel from the second junction to the third junction. Here a third sheath buffer flows into the third junction from the sides and the sample is pinched into single file down in the middle of the main channel in the bottom substrate.

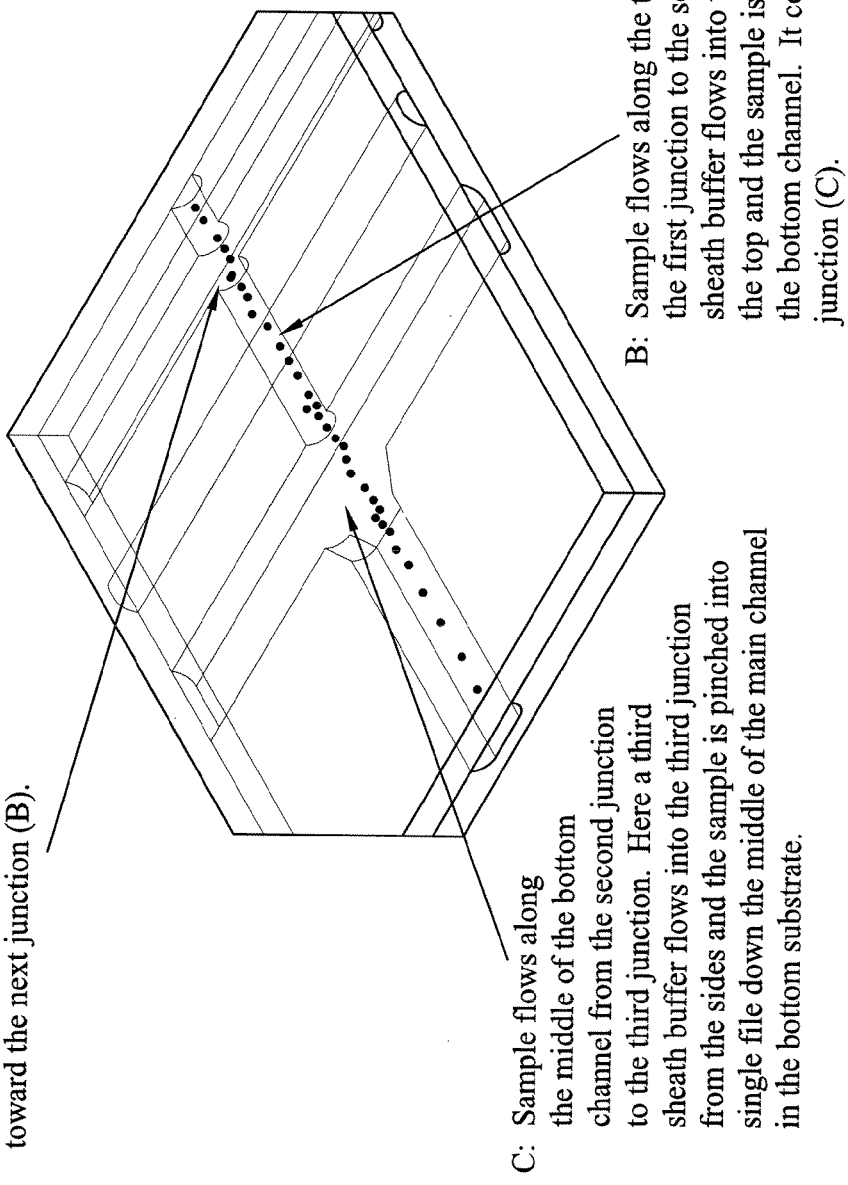

FIG. 15

A: Sample flows from top, into the junction and down into the channel in the bottom where the side sheath buffer flows into the junction from the sides. The sample is slightly focused and pushed to the top wall of the bottom channel as it continues to flow toward the next junction (B).

B: Sample flows along the top of the bottom channel from the first junction to the second junction. Here a second sheath buffer flows into the second junction from the top and the sample is pushed down to the middle of the bottom channel. It continues to flow toward the next junction (C).

C: Sample flows along the middle of the bottom channel from the second junction to the third junction. Here a third sheath buffer flows into the third junction from the sides and the sample is pinched into single file down the middle of the main channel in the bottom substrate.

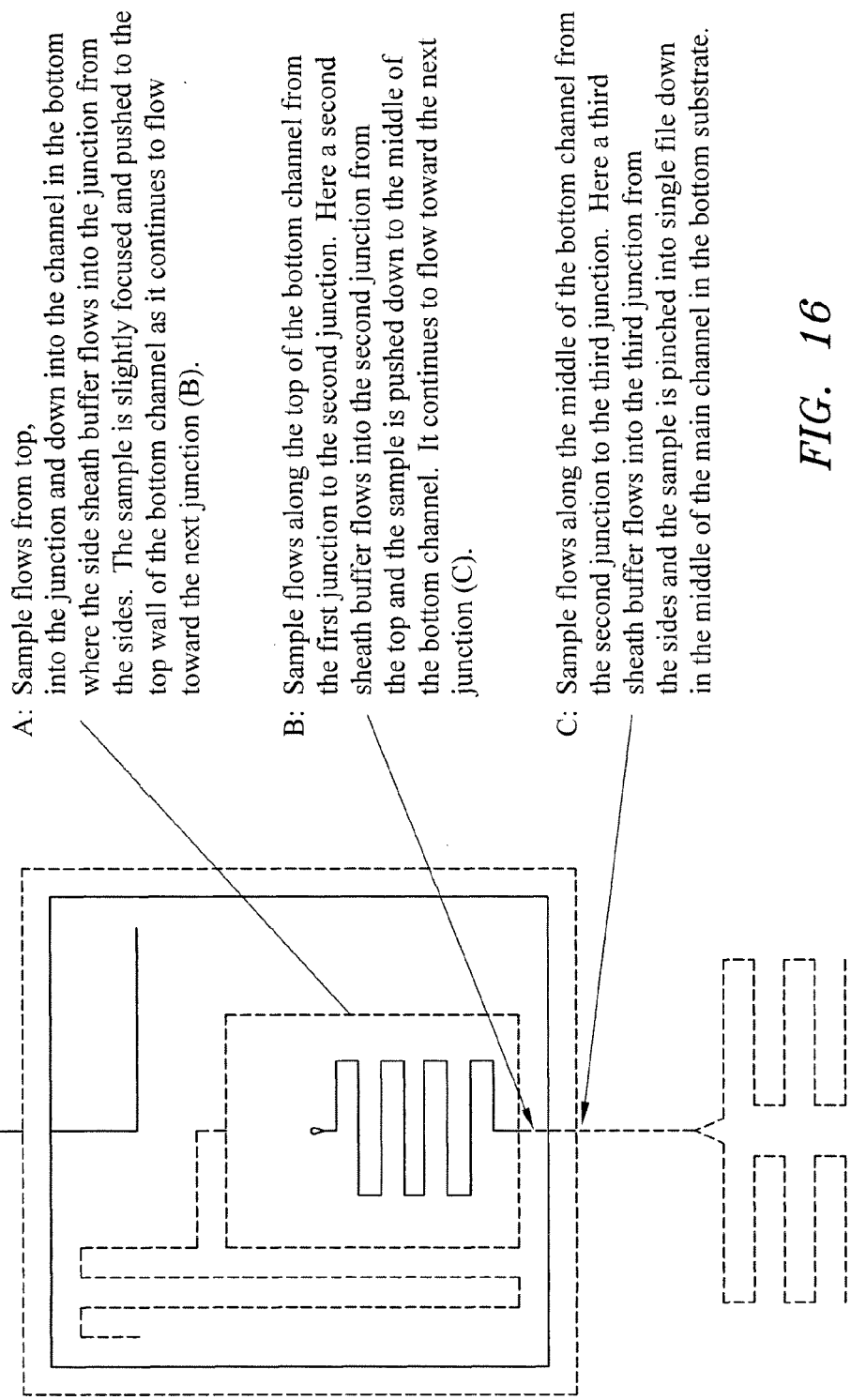

Dashed: Channels in one substrate
Solid: Channels in other substrate

A: Sample flows from top, into the junction and down into the channel in the bottom where the side sheath buffer flows into the junction from the sides. The sample is slightly focused and pushed to the top wall of the bottom channel as it continues to flow toward the next junction (B).

B: Sample flows along the top of the bottom channel from the first junction to the second junction. Here a second sheath buffer flows into the second junction from the top and the sample is pushed down to the middle of the bottom channel. It continues to flow toward the next junction (C).

C: Sample flows along the middle of the bottom channel from the second junction to the third junction. Here a third sheath buffer flows into the third junction from the sides and the sample is pinched into single file down in the middle of the main channel in the bottom substrate.

FIG. 16

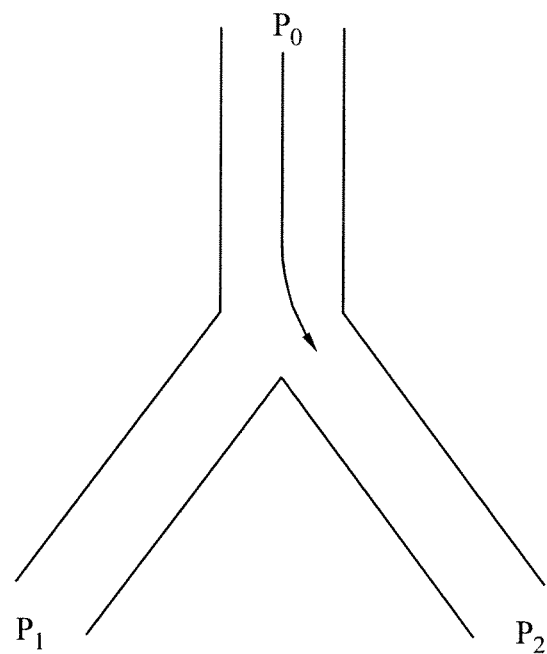
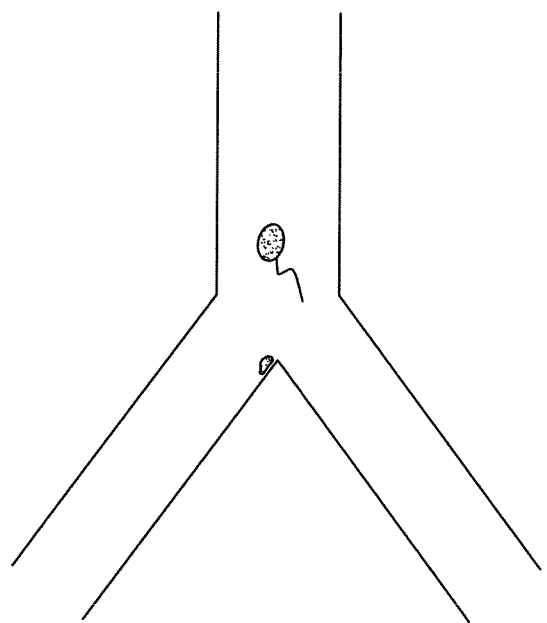
FIG. 23

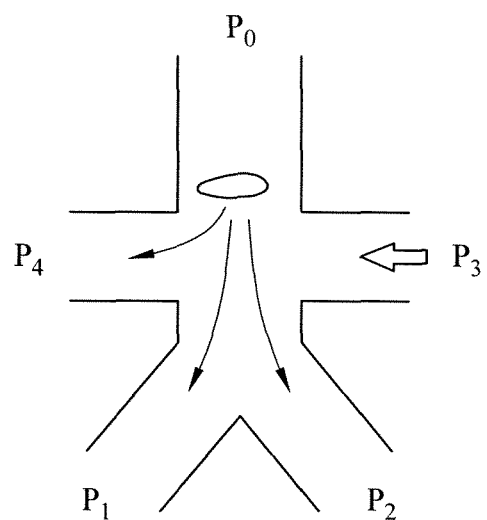
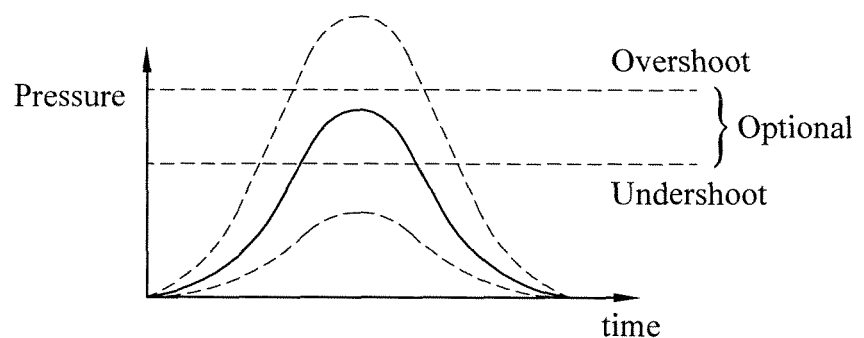
*FIG. 24a* b) An example that shows 5 millisecond switching window of previous microfluidic switching.

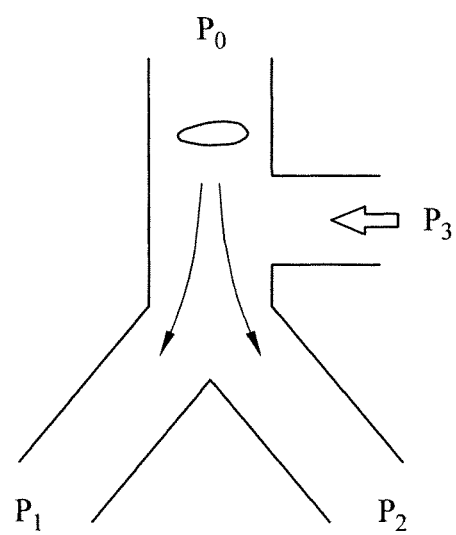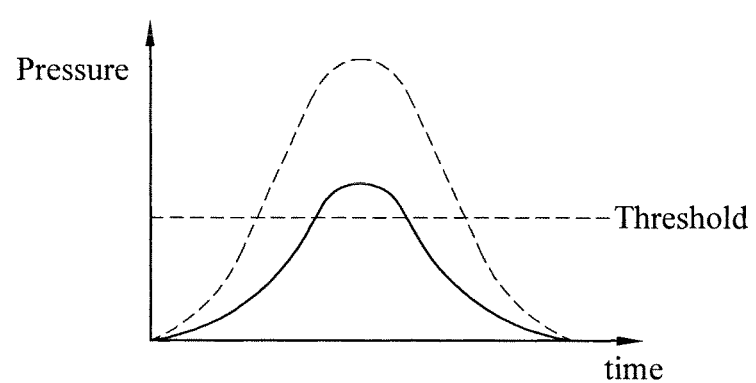
FIG. 25a d) An example that shows 1 millisecond switching window of new microfluidic switching with single side channel.

a) Single external valve operation and response.

b) Two external valve operation and response.

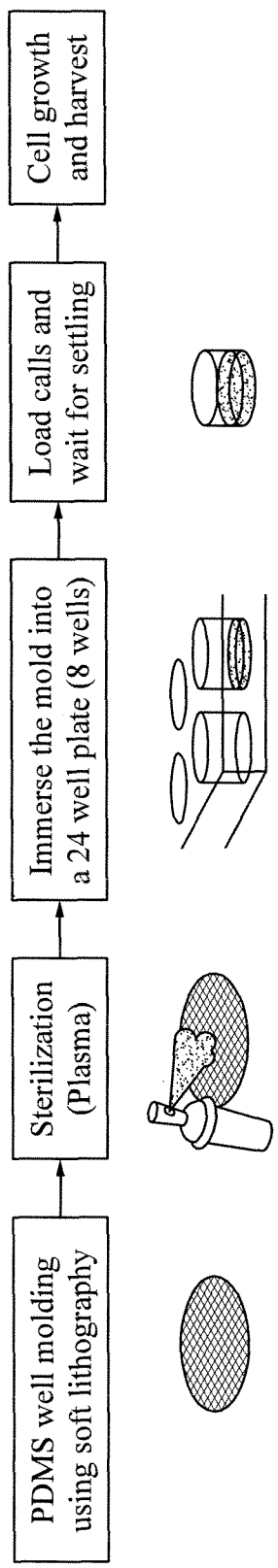
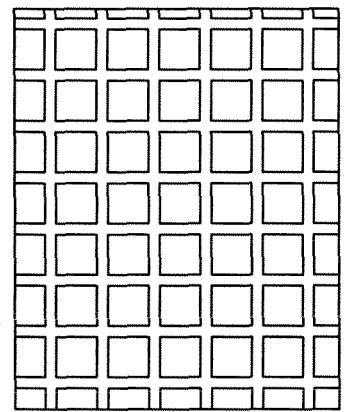
a) Schematic diagram of dilution cloning procedure
FIG. 33

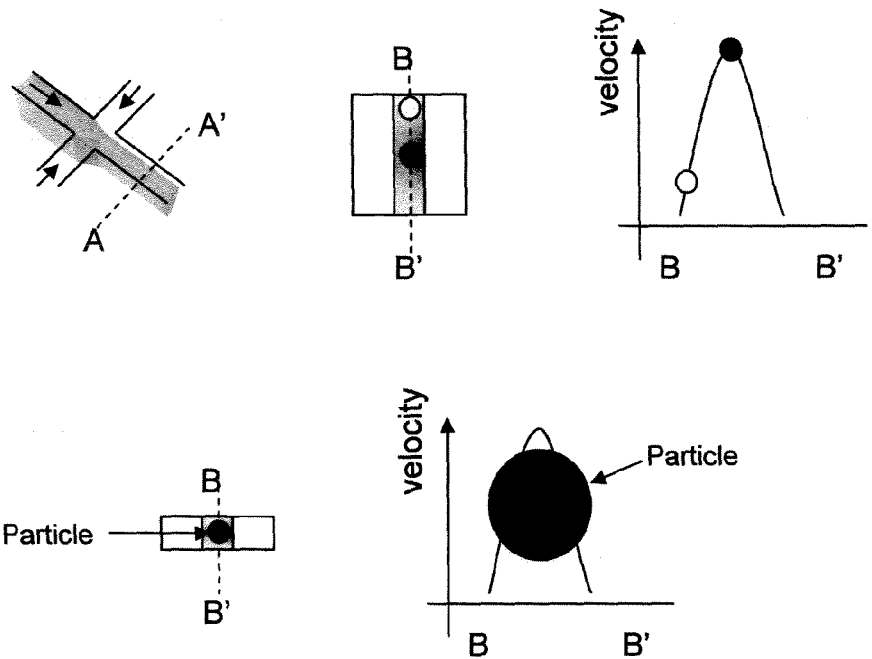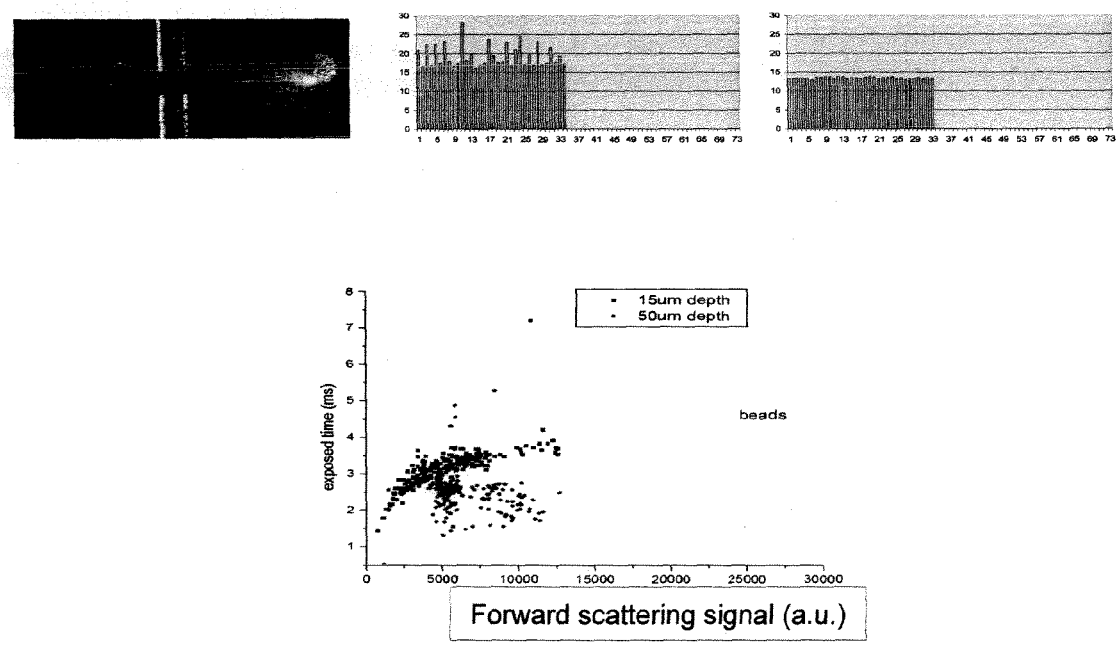
*Fig. 34*

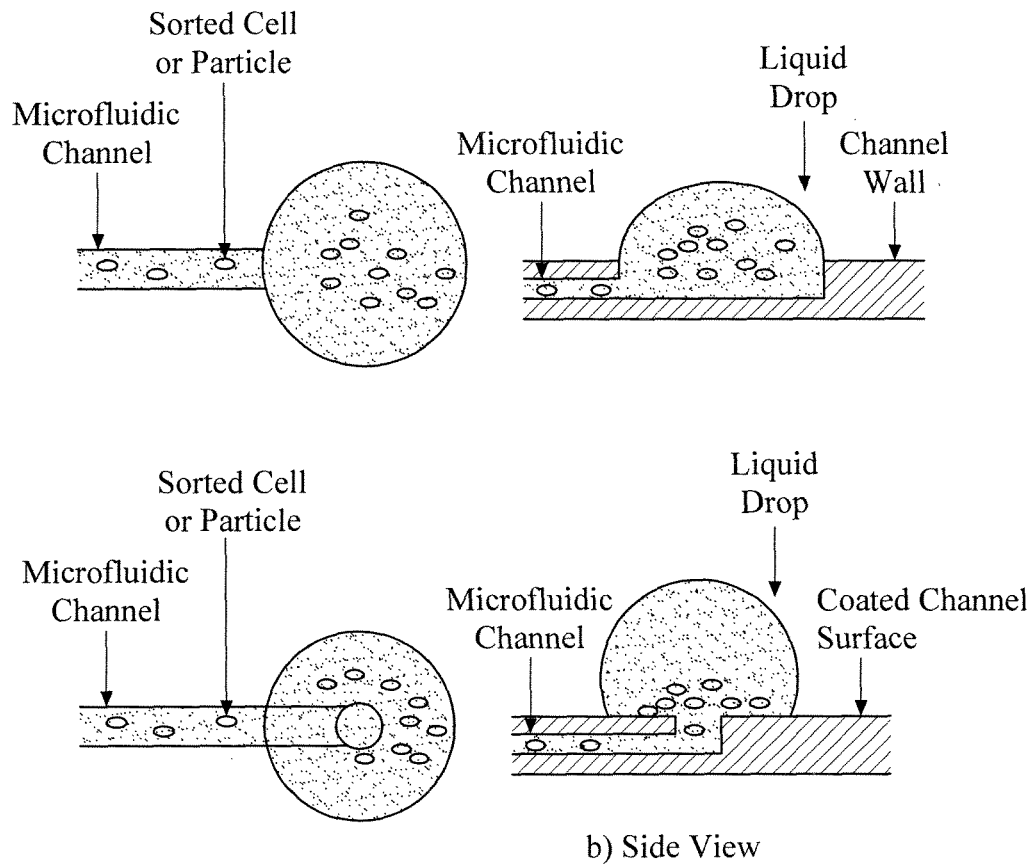
a) Tow view of a collection reservoir
b) Side View
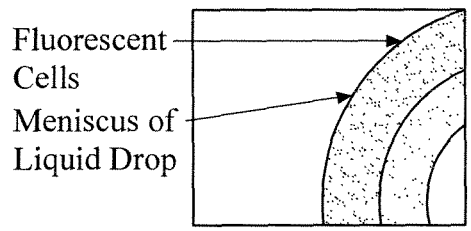
c) Real top view image of a collected drop containing sorted cells
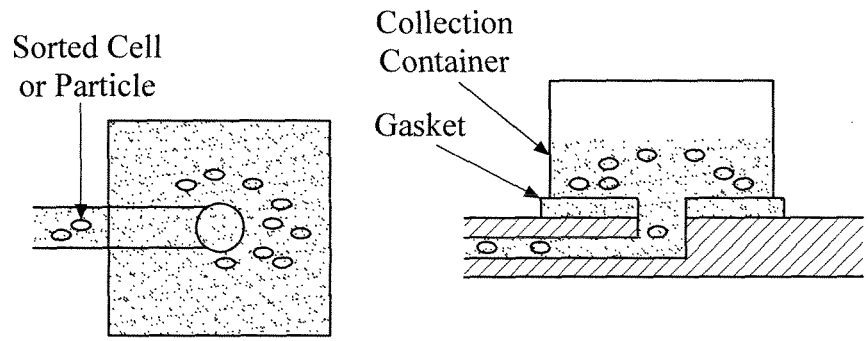
FIG. 36

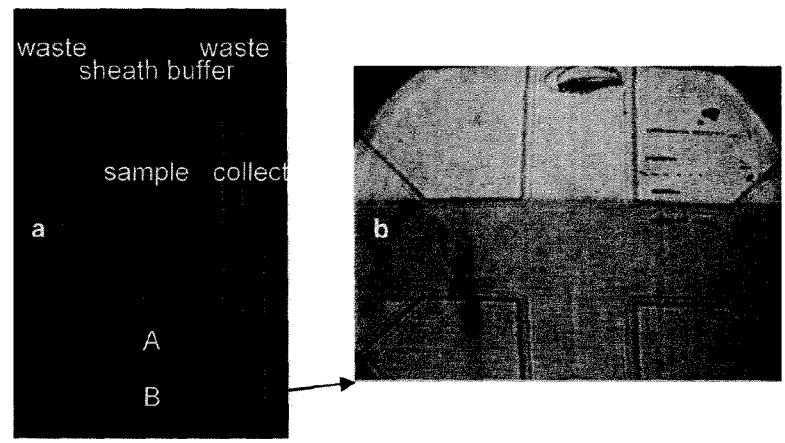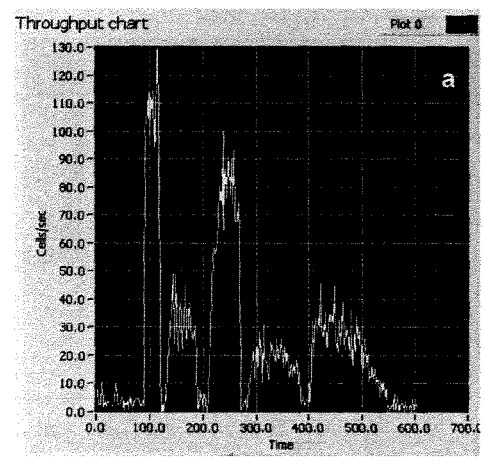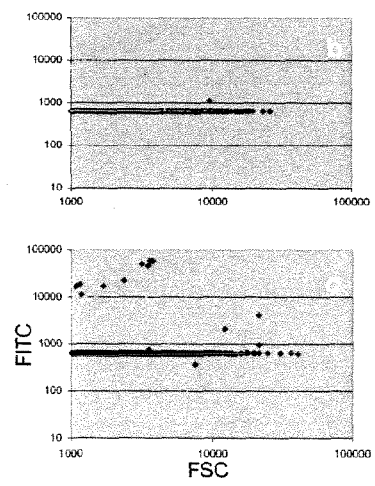
Fig. 38

CELL SORTING SYSTEM AND METHODS

PRIORITY CLAIM

This application claims priority to U.S. Provisional Application No. 60/925,563, filed Apr. 20, 2007, entitled "Cell Sorting System And Methods", which is incorporated herein by reference as if fully set forth herein.

FIELD OF THE INVENTION

This invention relates to methods and apparatus for the use of forces in a microfluidic channel network to provide a switch that enables selective routing of target cells through the network to sort them from non-target cells and collect them. Of particular interest are optical or fluidic switching forces.

BACKGROUND OF THE INVENTION

Conventional fluorescent activated cell sorters (FACS) are widely used in research and clinical applications[1]. These instruments are capable of very fast, multiparameter analysis and sorting but generally require large sample volumes, a trained operator for operation and maintenance, and are difficult to sterilize. FACS instruments are able to analyze as few as 10,000 and as many as tens of millions of cells. However, below 100,000 cells the ability to perform sorting diminishes[1]. Other separation methods such as magnetic beads don't require as many cells as FACS but they suffer from nonspecific binding, aggregation of cells and beads, and from the possibility that the beads themselves could interfere in subsequent processing steps. Thus, for sorting precious, small samples or cells from primary tissue, a cell sorter that is capable of handling small sample volumes with low cell numbers and that allows efficient recovery of the sorted populations addresses a unique scientific niche.

Microfabricated cytometers have the potential to sort with as few as 1,000 cells while concomitantly consuming less reagents in an easy to use, closed system. The latter is important because, unlike conventional FACS instruments, aerosols are not created, reducing the risks of contamination of the sorted cells and of working with biohazardous materials. Several microfabricated cell sorters have been described, but mostly as "proof of concept". Fu, et al.[2] reported 30-fold enrichment of E. coli at a throughput of 17 cells/s. Only 20% of the bacteria were viable after sorting and the sort purity in the target reservoir was 30%. In a subsequent study[3], the throughput increased to 44 cells/s but the target purity decreased to less than 10%, with recovery reported as 39%. Wolff, et al.[4] were able to sort beads from chicken red blood cells at a throughput of 12,000 events/s, with 100-fold enrichment. However, purity in the target well was about 1%. In these studies, enrichment was defined as the increase in the concentration of the target population in the collection well compared to the starting concentration. Purity referred to the accuracy of the sort and was the percentage of target cells sorted over all cells sorted into the collection well. Recovery was defined as the number of cells counted by the fluorescent detector vs. cells recovered from the collection well. The latter two studies used pressure switches in microfluidic devices that switched the entire fluid flow path and, consequently, any particles contained within the fluid plug. The mechanical compliance in these switches caused the fluid switch speed to be the rate limiting step for throughput[3]. Electrokinetic flow control has also been reported, e.g., electroosmosis[2,5,6] or dielectrophoresis[7,8,9], but the high electric field gradients and physicochemical restrictions on the ionic strength of the buffer are non-ideal conditions for cells.

Buican et al.[9] first proposed the use of optical forces for the deflection of particles through a fluidic channel. The force exerted on a particle by an optical beam is a function of the optical power and the relative optical properties of the particle and its surrounding fluid medium. Forces on the order of 1 pN/mW can be achieved for biological cells approximately 10 µm in diameter. While the optical force is small, the force necessary to deflect a cell into an adjacent flowstream is also small, e.g. 900 pN to move a 10 µm diameter cell, 20-40 µm laterally across the flow in a few milliseconds. This is the force necessary to overcome the viscous drag force on the cell at the velocity implied by this lateral motion.

The principles behind the optical forces and general background technology may be found in U.S. Pat. No. 6,744,038, which is incorporated herein by reference as if fully set forth herein.

Various pneumatic pressure modulation systems and methods for particle sorting in microfluidic devices have been known to the prior art. By alternating pneumatic pressure interfacing to a microfluidic device, particles including cells flowing in the microfluidic channel can be directed to desired branch or branches, so that a low cost sorting functionality can be achieved.

SUMMARY OF THE INVENTION

As described below, these forces are used to realize a switch in a microfluidic channel network, operable as a cell sorting system. The switch is triggered by detection of a fluorescence signal from target cells flowing in the microfluidic channel network upstream of the switch position, although other detection modalities such as light scattering could equally be used for activation of the switch. The switch is used to direct cells or particles into one of a multiple number of output channel flow streams without modifying the underlying flow, whereby the desired cells are collected for further use. It is desirable that the flow in a microfluidic channel is typically laminar at a very low Reynolds number. Consequently, any cell flowing in a particular lamina, or flow stream, will stay in that flow stream in the absence of any forces transverse to the lamina. The switch utilizes forces on a cell to accomplish just this, the transport of cells transverse to the lamina to move the cells from a flow stream that exits a bifurcation junction through one output channel to a flow stream that exits the bifurcation junction through the second output channel.

In one embodiment, a cell sorter comprises a cell inlet adapted to receive one or more cells in a fluidic medium; a first and second buffer inlets fluidically coupled to the cell inlet to provide buffer solution to the sorter, a fluidic channel fluidically coupled to the cell inlet and first and second buffer inlets, a first lateral flow channel fluidically coupled to the fluidic channel, first and second outputs fluidically coupled to the fluidic channel, the outputs being located downstream of the lateral flow channel, a detector adapted to detect cells of a given state and to generate a signal in response thereto, the detector positioned to detect cells at a position upstream of the first lateral flow channel, a lateral force switch coupled to the detector and actuatable in response to the signal to cause fluid to move within the lateral flow channel; whereby when a cell of a given state is detected, the lateral force switch is activated to provide a lateral force on the cell so as to move the cell such that it selectively exits into the first or second outputs.

The invention described in the following paragraphs details the methodology used to create a switch and the approaches used to optimize the switch, the design of the microfluidic channel network and the properties of the flow of cells or particles in the microfluidic network in order to achieve enhanced sorting performance. In the event of an optical switch, the optical switch generally works by projecting an optical illumination field into the microfluidic channel network in the vicinity of the cell's trajectory in an established flow in a microfluidic channel. The interaction of the cell with the optical field produce forces on the cell that transport it transverse to the established flow such that it moves from one flowstream to another flowstream in the established flow, without trapping the cell or significantly altering its motion in the primary flow.

In the following text the terms cells and particles both will be understood to mean any of biological cells, biological particles, natural organic or inorganic particles and man-made organic or inorganic particles. The size range of the cells sorted in the microfluidic channel network is typically that of biological cells, with diameters ranging from approximately 1 µm to approximately 50 µm. More generally, cells with diameters ranging from approximately 100 nm to approximately 100 µm are candidates for sorting by means of a switch in a microfluidic channel network.

In one embodiment, an optical switch is utilized. In general a laser has been used to produce the optical beam used in the optical switch. The laser currently used for the optical switch is a near-IR, continuous wave laser that is known not to harm the viability of biological cells at the power densities and exposure times used to demonstrate optical switching. Alternate laser sources may be considered for different applications, including visible or near-UV wavelength lasers if damage to the particles is not an issue, or pulsed lasers where a large flux of light can be used to move the particle very quickly. However, the source of the optical beam does not need to be limited to a laser, even though further discussion of the invention uses a laser to produce the optical switch.

In yet another embodiment, a fluidic switch may be utilized. Preferably, a pneumatic based fluidic switch may be utilized. In another embodiment, a microfluidic chip design for cell sorter uses pneumatic pressure modulation. A single side channel for flow switching or cell sorting may be used in microfluidic devices. The described channel geometry provides for efficient pneumatic flow switching in microfluidic devices. In yet another aspect, a coupling of two switching valves on a single side channel minimizes pneumatic switching response time. In yet another aspect, a cartridge holder is provided for pneumatic control of microfluidic chips.

With particular application to a fluid switching system, a fluidic sorter switching system comprises an inlet adapted to receive a fluidic medium; a fluidic channel fluidically coupled to the inlet, first and second lateral flow channels fluidically coupled to the fluidic channel, first and second pneumatic valves connected to the first and second lateral flow channels, first and second outputs fluidically coupled to the fluidic channel, the outputs being located downstream of the lateral flow channel, and a control system, the control system being coupled to the first and second valves, the control system providing timed control signals to actuate the first and second pneumatic valves, characterized in that the first valve is opened prior to the second valve being opened. In yet another aspect, the switch is further characterized in that the first valve is closed after the second valve is opened and prior to the second valve closing. In yet another aspect, the second lateral flow channel and second pneumatic valve may be eliminated to achieve sorting using a single lateral channel with one or two pneumatic valves.

In yet another embodiment, a microfluidic cell sorter uses both optical switch and pneumatic pressure modulation. An optical and opto-mechanical design is also provided. Preferably two laser illumination modules and dark illumination module are utilized. High performance high NA (numeric aperture) objective lens are preferably used to collect fluorescence.

In yet other aspects of the inventions, fluorescence signal detection and processing systems and methods are utilized. An ADC is preferably used to convert the analog signal to digital signal. In one embodiment, digital signal processing algorithm is implemented in a FPGA.

Optionally, auto alignment of the cartridge is provided. This invention solves the auto alignment problem for cartridge loading in the system.

In yet other aspects, the inventions relate to the application software design for the microfluidic sorter instrument. Streaming raw data from external device between multiple executable applications and processes in a format that is recordable, lossless, and high speed (10 Mega-Bits-Per-Second or greater).

In yet other embodiments, a microfluidic cartridge priming station is provided. The invention describes of priming station for priming of microfluidic devices.

In yet other aspects, dilution cloning for growth monitoring and selection of cells, e.g., fetal cells, is provided. The invention describes dilution cloning method for growth monitoring and selection of such cells.

BRIEF DESCRIPTION OF THE DRAWINGS

FIGS. 8a, 8b and 8c show optical designs for modulation and/or shuttering of the optical switch.

FIG. 14 is an illustration of the side view of a microfluidic channel network that provides sequential sheath flow pinch of the cell flow in the vertical direction and then in the horizontal direction, resulting in full 2-dimensional sheath flow pinch of the cell flow in the main channel.

FIG. 15 is a 3-dimensional illustration of the microfluidic channel network described in FIG. 14.

FIG. 16 is a schematic of a representative photolithography mask design for both bottom and top glass substrates that when bonded together form the microfluidic channel network illustrated in FIGS. 14 and 15.

FIG. 23 is a plan view of a prior art "Y" shaped sorting junction in a microfluidic channel network that shows a particle trajectory for pneumatic based fluidic switching FIGS. 24a and 24b are plan views of a "Y" shaped sorting junction in a microfluidic channel with a two-channel fluid switch that shows possible particle trajectories under various pneumatic differential pressures.

FIGS. 25a and 25b are plan views of a "Y" shaped sorting junction in a microfluidic channel with a one-channel fluid switch that shows possible particle trajectories under various pneumatic differential pressures.

FIG. 33 shows dilution cloning for growth monitoring and selection of fetal cells. The invention describes dilution cloning method for growth monitoring and selection of fetal cells.

FIG. 34 is a shallow microfluidic channel for one-dimensional flow focusing. The invention describes a method to overcome intrinsic velocity dispersion of one-dimensional flow focusing for microfluidic flow cytometry or sorting.

FIG. 36 is a microfluidic outlet port configurations for efficient sample collection. The invention describes several sample collection methods after cell or particle sorting using microfluidic devices.

FIG. 38 is a microfluidic analysis chip for sample analysis and recovery. The invention describes several microfluidic devices for sample analysis and recovery with less dilution

DETAILED DESCRIPTION OF THE INVENTION

Figure 1:
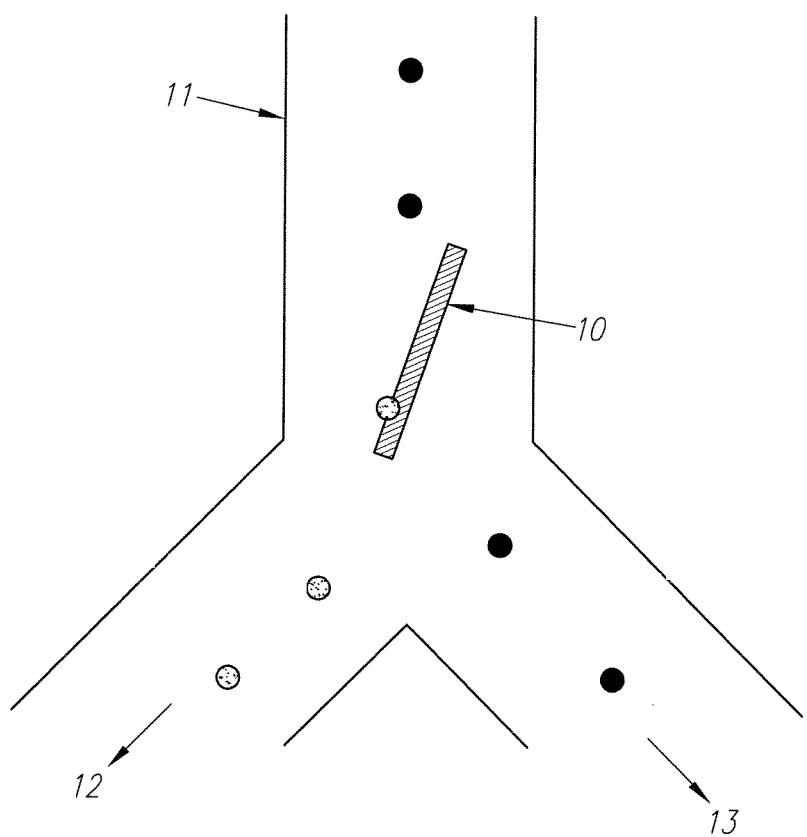
FIG. 1 is a plan view of a "Y" shaped sorting junction in a microfluidic channel network.

FIG. 1 shows one embodiment of an optical switch 10 that serves to sort cells in a 1×2 microfluidic channel network, i.e. a network with one main input channel 11 and two output channels 12 and 13 extending from a bifurcation junction. A "Y" geometry for the bifurcation junction is shown in FIG. 1, but other bifurcations such as a "T" geometry may also be used. In general these microfluidic channels are produced in optically transparent substrates to enable projection of the optical switch and other cell detection optics into the channel. This substrate is typically, but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 μm to 100 μm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels.

The flow conditions are set such that when the optical beam, in this case from a laser, is turned off or blocked so that the beam does not impinge on the junction region, all cells will preferentially flow into one of the output channels, for example the right output channel 13. When the optical beam is turned on or unblocked, the beam strikes the junction region and optical forces generated by the interaction of the cells with the optical beam direct the cells into the left output channel 12. In this example, the optical pattern chosen for directing the cells is a long, thin line of laser illumination at some angle relative to the direction of fluid flow. Optical gradient forces displace the cells laterally, away from the main stream line of cells, such that switched cells then exit the main channel into one output channel, for example 12 while unswitched cells from the main stream of cells exit into the other output channel, for example 13. The setting and control of the flow conditions in the microfluidic channel network can be achieved by direct drive pumping, pneumatic pumping, electro-kinetics, capillary action, gravity, or other means to generate fluidic flow.

The performance of the sorting mechanism in terms of throughput (the temporal rate of cells entering the sorting region at the top of the bifurcation junction), yield efficiency (the fraction of target cells in the target output channel, 12), and purity (the ratio of the number of target cells to the total number of cells in the target output channel, 12), are impacted by various factors, each of which affects the implementation of the optical switch. The optical switch can be characterized by several parameters such as the shape of the optical pattern projected into the sorting junction region of the microfluidic channel network, the position of the pattern with respect to the bifurcation junction, any motion of the optical pattern with respect to its initial position and shape, the duration of activation of the optical switch, the wavelength and power of the laser source used to produce the optical switch pattern, etc. The selection of particular values of these parameters for the optical switch is a critical function of, among other things, the topology and geometry of the microfluidic channel system, the flow rates (cell velocities) within the microchannel system, the ability to control the position of cells flowing in the main channel (whether they are flowing in the center of the main channel or off-set to one side), the amount of displacement of the cells necessary to achieve reliable switching, the depth of the channels, the shape of the channels, and the forces produced by the cells' interactions with the optical switch.

In general, when cells are introduced into the flow in the main channel they may move down the channel at any transverse position within the flow. Consequently the cells may be moving at differing velocities, depending upon their transverse positions due to the well known parabolic (for cylindrical microfluidic channels) or quasi-parabolic (for more general cross sections) velocity profile of pressure driven flow in microfluidic channels. This would make it difficult to bias the flow of all cells to one output channel, say 13, as shown in FIG. 1. Any implementation of an optical switch with this flow geometry would necessarily result in low throughput and inefficient use of the laser power available to produce the optical switch. Any implementation of a fluidic switch with this flow geometry would result in low throughput, purity and yield due to the variable cell time of flight between the detection region and the switching region. The use of appropriate flow conditions can help alleviate these restrictions on the performance of the optical or the fluidic switch.

Figure 2:
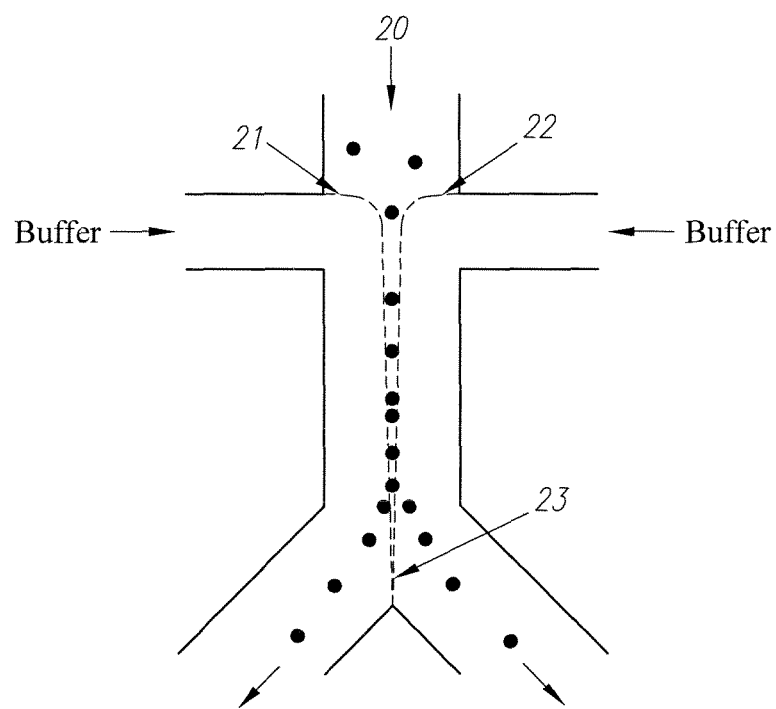
FIG. 2 is a plan view of a microfluidic channel network that incorporates both a sheath flow pinch junction and a "Y" shaped sorting junction connected by a main channel, with 50/50 splitting of cells in the flow, collectively referred to as a 50/50 optical switch network.
Figure 24B:
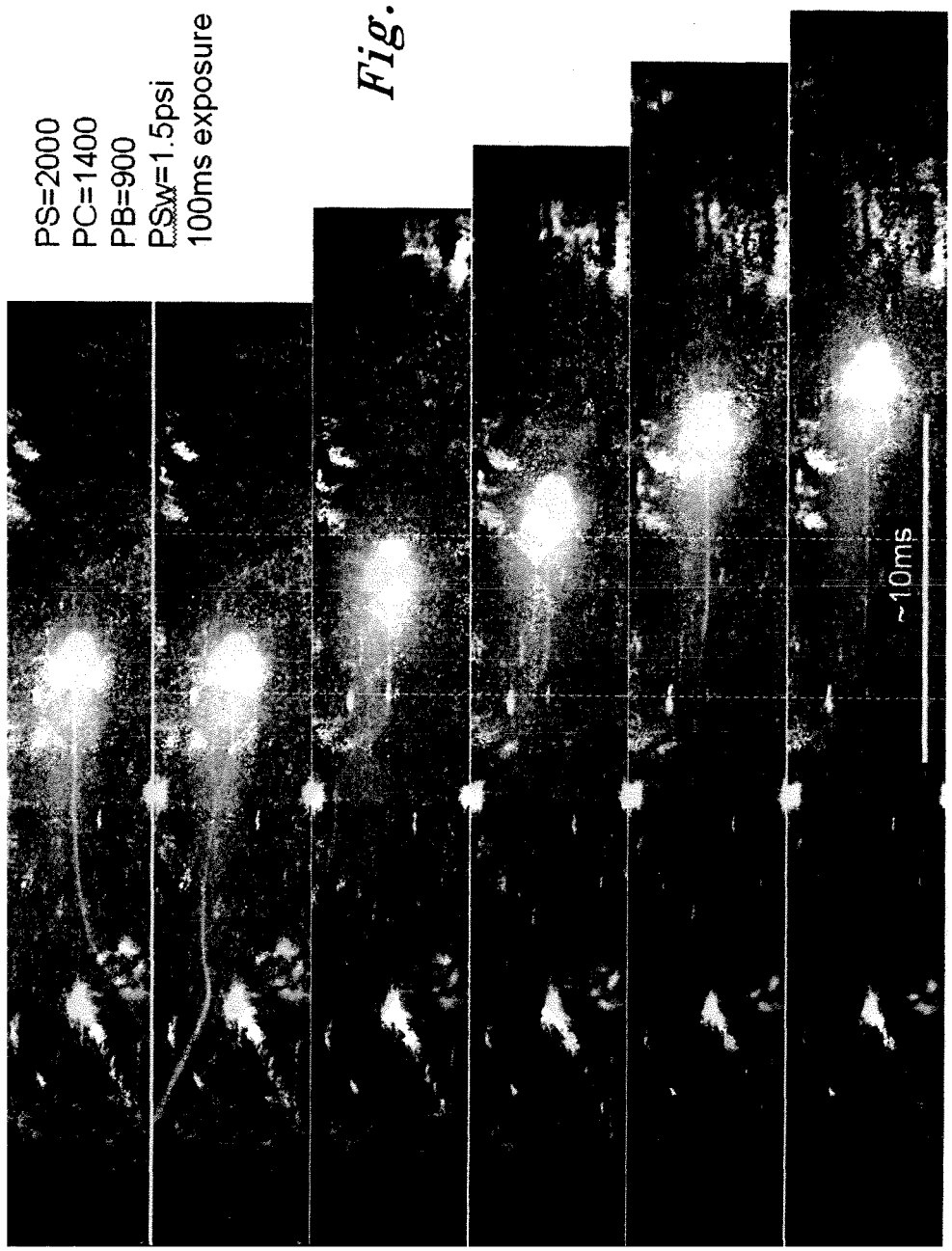

Establishing the appropriate flow conditions can be done in many ways. In one embodiment, 1-dimensional focusing of cells (horizontally in the planar view shown) into a single file in the center of the main channel is achieved by pinching the cell input channel flow 20 with added flow of buffer from both the left 21 and right 22 sides, using a sheath flow approach as shown in FIG. 2. Maintaining the cells in the center of the main channel is achieved by having equal flow from each side. This flow effectively creates a fluidic splitting plane 23, as shown in FIG. 2, and this ultimately will result in a 50/50 splitting of the fluid and cells at the bifurcation junction. Implementation of an optical switch to sort target cells from a mixed population of cells using this microfluidic channel design and flow conditions requires an optical switch that actively switches both target cells to one output channel, say 12 as shown in FIG. 1 and non-target cells to the other output channel, say 13. Implementation of a fluidic switch to sort target cells from a mixed population of cells using this microfluidic channel design and flow conditions requires an fluidic switch that actively switches both target cells to one output channel, say 12 as shown in FIG. 1 and non-target cells to the other output channel, say 13. A two-channel fluidic switch in FIG. 24 is an example of such an embodiment.

Figure 3A:
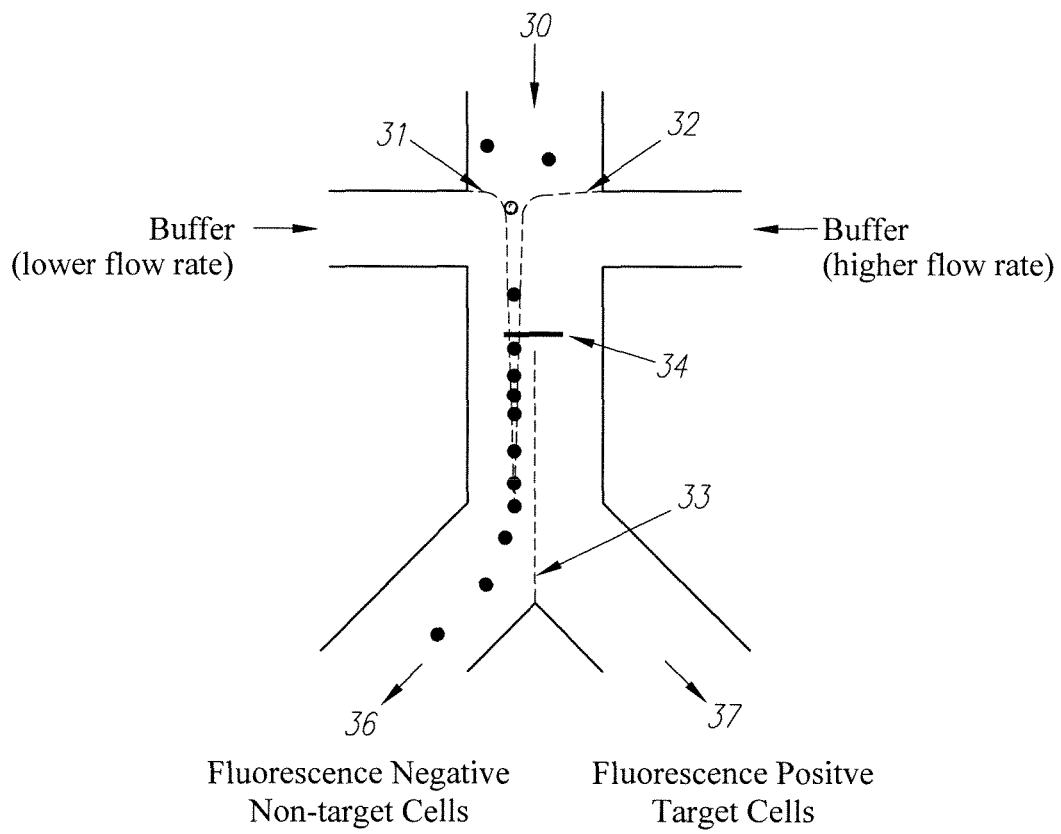
FIGS. 3a and 3b are plan views of a microfluidic channel network that incorporates both a sheath flow pinch junction and a "Y" shaped sorting junction connected by a main channel, with skewed splitting of cells in the flow via differential sheath flow, collectively referred to as a sheath flow skewed optical switch network, with an optical switch.
Figure 3B:
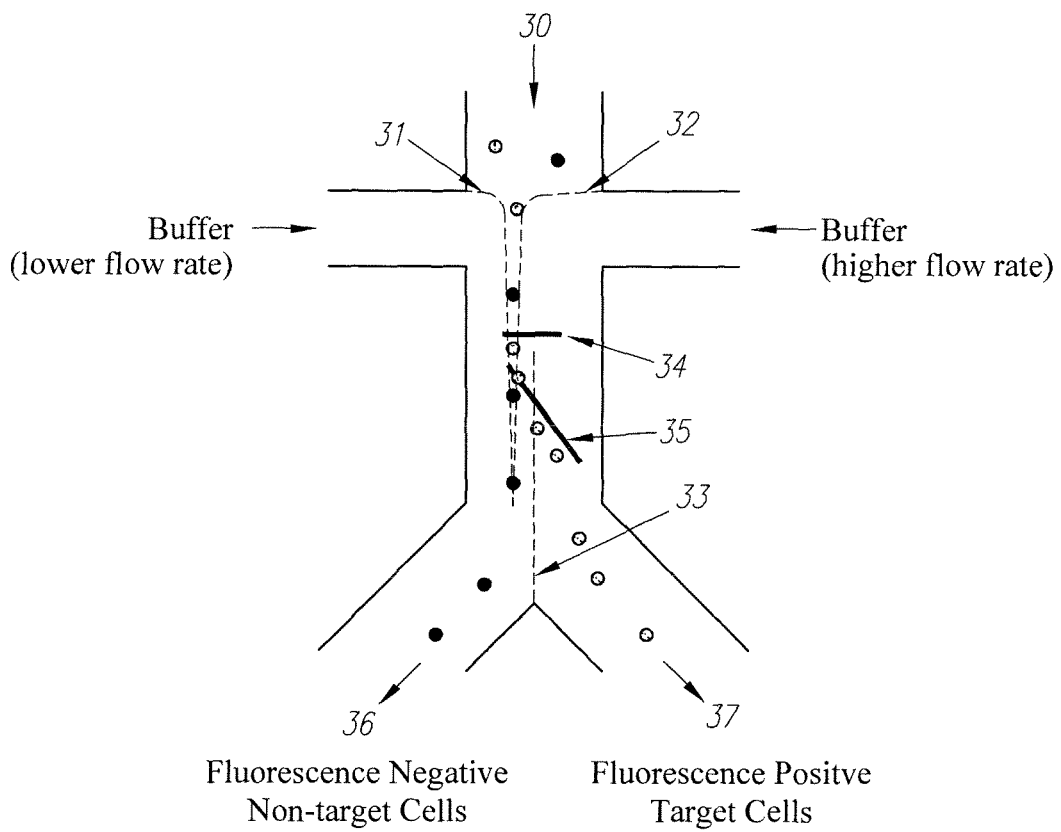

Alternatively, the focused line of cells can be positioned off-set from the center of the main channel by putting unequal flows into the side sheath flow channels, FIG. 3*a-b*. This effectively causes a skewed flow of cells from the input channel 30 to one side of the splitting plane 33 within the main channel. The side of the main channel to which the cell flow is skewed will be opposite to the side in which the sheath flow has the higher flow rate. That is, when the right sheath buffer 32 flows faster than the left sheath buffer 31, the line of cells is skewed toward the left of the flow in the main channel, as shown in FIG. 3*a-b*. However, the left sheath flow could also have the higher flow which would push the line of cells toward the right side of the main channel. Also shown in FIG. 3*a-b* are a fluorescence detector 34 and an optical switch 35. The fluorescence detector is used as a means to decide which cells to sort, and will be discussed in further detail later. It is evident from FIG. 3*b* that an effective sort involves moving a cell across the splitting plane from a flow stream that exits the bifurcation junction to the fluorescence-negative non-target cell microfluidic channel 36 into a flow stream that exits the bifurcation junction to the fluorescence-positive, target cell microfluidic channel 37. Manipulation of the sheath buffer flow rate can be achieved either by separately controlling the flow rate in the respective side channels using direct drive pumping, pneumatic pumping, electro-kinetics, capillary action, gravity, or other means to generate fluidic flow, or by specifically designing the microfluidic sheath network to ensure that central flow (50/50 splitting) or off-set flow occurs, through careful balancing of the pressure drops in each of the microfluidic channels.

Figure 4A:
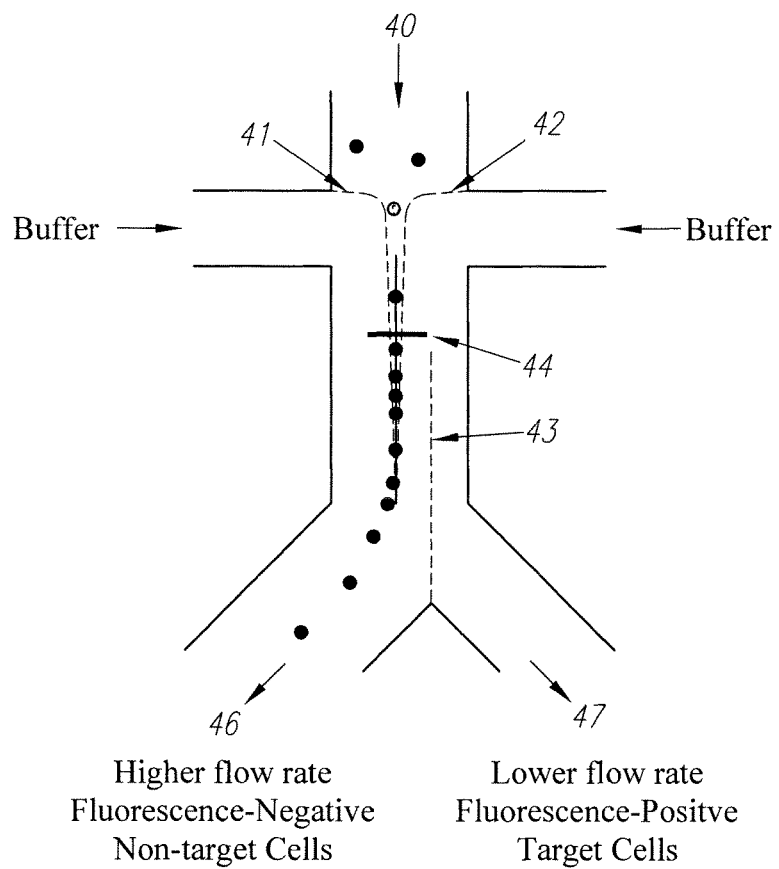
FIGS. 4a and 4b are plan views of a microfluidic channel network that incorporates both a sheath flow pinch junction and a "Y" shaped sorting junction connected by a main channel, with skewed splitting of cells in the flow via differential outlet channel width, collectively referred to as an outlet flow skewed optical switch network, with an optical switch.
Figure 4B:
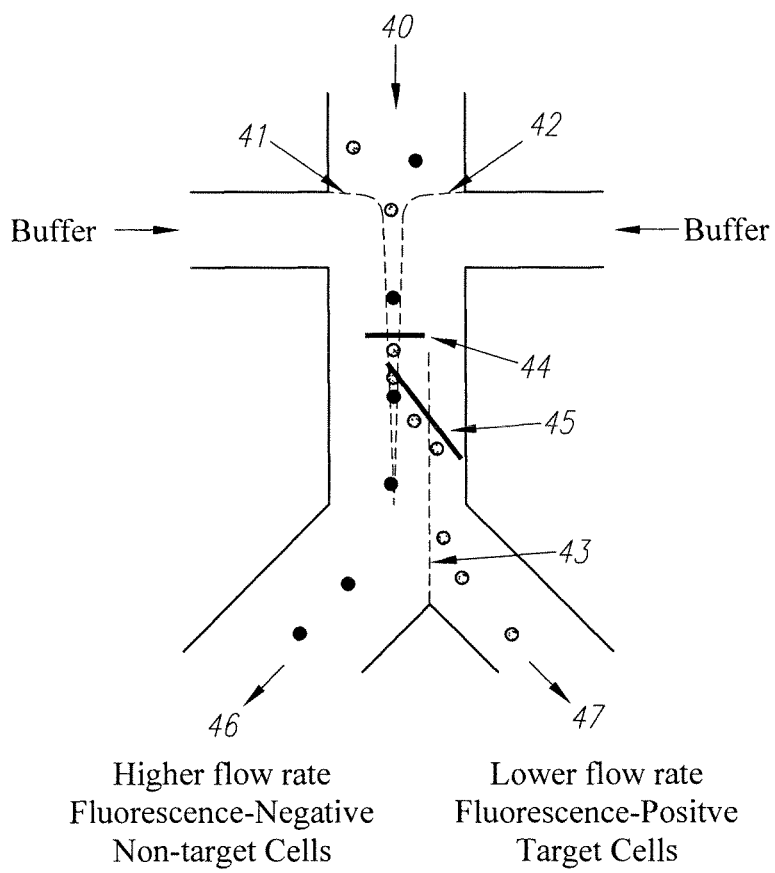

An alternative approach to achieve the preferential flow of all cells from the input flow 40 in the main channel into one output microfluidic channel, say the fluorescence-negative channel 46, prior to fluorescence detection 44, is to obtain central pinching using equal sheath buffer flow rates 41 and 42, but then preferentially bias the cell flow into fluorescence-negative channel by having a larger volumetric fluid flow out of the bifurcation junction into the fluorescence-negative output channel 46 relative to the fluorescence-positive output channel 47. This is demonstrated in FIG. 4*a-b*, in which the left output channel 46 is wider than the right output channel 47. This configuration effectively places the splitting plane 43 to the right of the centrally located cell stream. Therefore, with the cells in the desired position, the optical or fluidic switch 45 is then used to translate the target cells across the splitting plane into the target cell, fluorescence-positive, right output channel. This approach is equally effective by having the right output channel wider than the left output channel, whereby target cells are translated by the optical or fluidic switch across the splitting plane, which is now located to the left of the centrally located cell stream, and are consequently sorted into the left output channel. Thus, by specifically designing the microfluidic channel outlet network, or by actively controlling the outlet back pressure in the respective outlet channels, the flow of cells into a desired output channel can be controlled.

The use of either central flow or an off-set flow, and the respective distance of the focused cell flow from a fluidic splitting plane, ultimately dictates the magnitude of the displacement of the cells necessary to achieve reliable switching. This further dictates the length of the laser line and the laser power required to achieve reliable optical switching or the amplitude and duration of the pneumatic pulses required to achieve reliable fluidic switching. The closer the cell stream is to the splitting plane, the shorter the displacement required, and the more efficient the sorting process becomes. For enhanced purity of the sorted population and for high throughput, the single switch, either optical or fluidic, in a mono-directional arrangement requires the sample stream be offset from the splitting plane. In this manner the occurrence of a mistaken sort is minimized. For samples heterogeneous in size, such as single cell suspensions of primary tissues where cells and debris may vary in diameter from 1 μm to 50 μm, it is advantageous to favor a larger off-set at the cost of throughput. For more homogeneous samples, e.g., cell lines or polystyrene beads, a smaller off-set may be selected to allow increased throughput.

An alternative to this design is to use a bidirectional optical switch which utilizes two laser lines. With this approach one laser line sorts the desired cells to one output channel, and the other laser line sorts all other cells into the other output channel. This approach can be used with either the 50/50, FIG. 2, or the offset, FIGS. 3 and 4, splitting configuration. In the latter case when a cell is not in the switching zone, one may choose to leave the laser on in either of its two positional states, or one may also shutter the laser during this time. The optical switch can also be made bi-directional by having two mirror-image laser lines impinging on the switching region, located just above the bifurcation junction, which independently turn on to direct cells to either of the two outputs stemming from the bifurcation junction.

Figure 5:
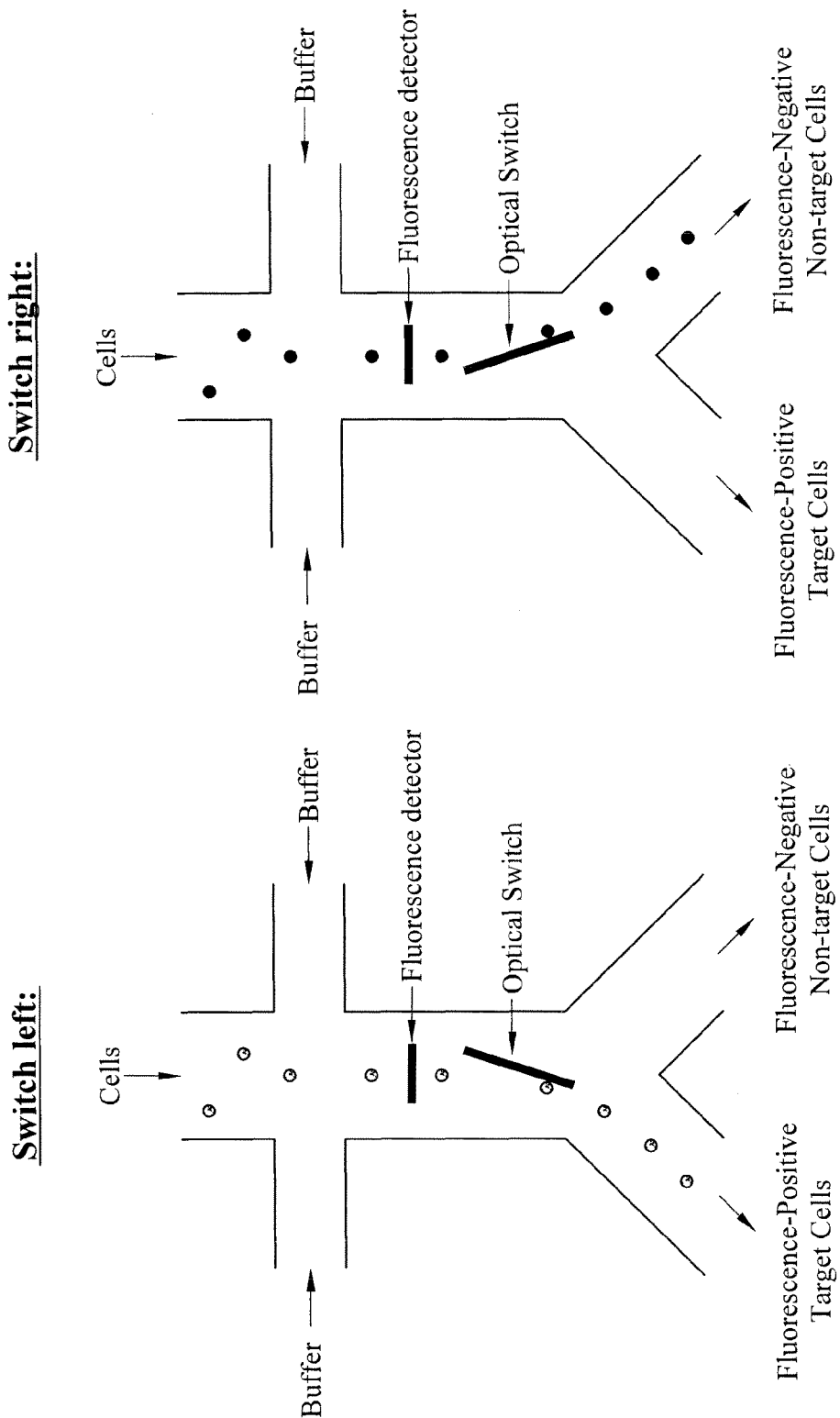
FIG. 5 is a 50/50 optical switch network with a bi-directional laser line optical switch.
Figure 6:
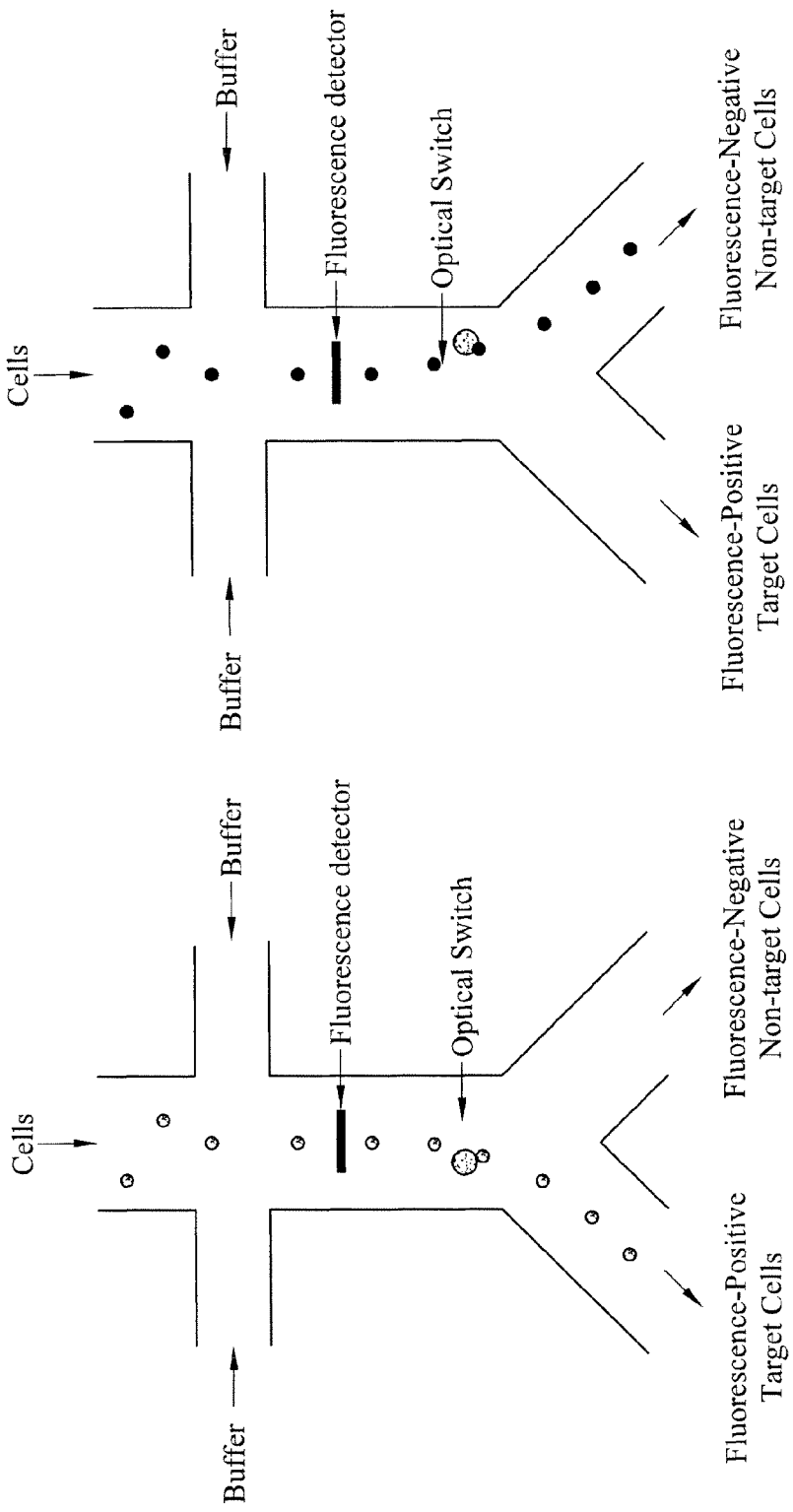
FIG. 6 is a 50/50 optical switch network with a bi-directional laser spot optical switch.

A schematic of the bi-directional optical switch using laser lines in a 1×2 microfluidic network is shown in FIG. 5. A similar bi-directional optical switch has also be achieved with laser spots directed to either side of the channel, as shown in FIG. 6. As with the mono-directional optical switch, a single laser source can be used in the bi-directional optical switch, or alternatively the bi-directional optical switch can use two independent laser sources. The bi-directional design potentially offers some performance advantages versus the mono-directional design. The first is that purity is potentially maximized because every cell is directed by the laser. Secondly, the fluid flow is simplified because equal flow can be directed out each of the two output ports, instead of some predetermined ratio of flow.

Figure 7A:
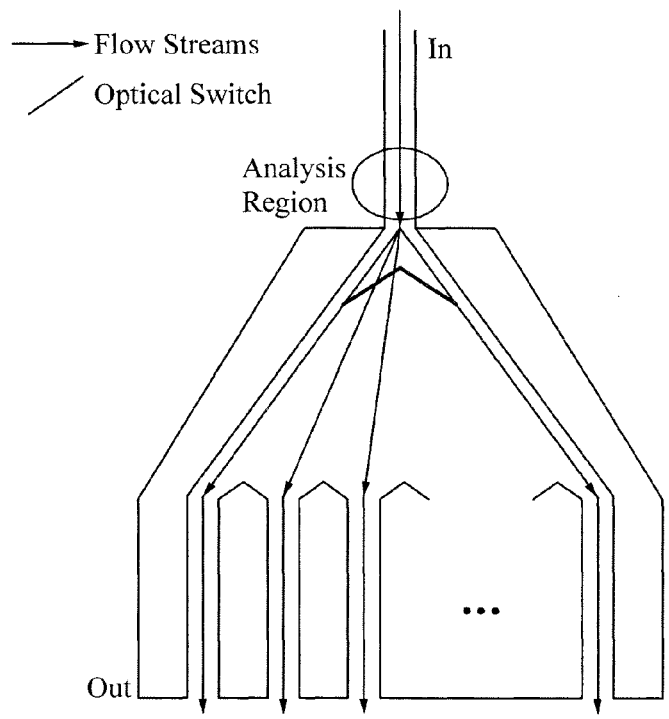
FIGS. 7a, 7b and 7c are plan views of laser line optical switches in larger microfluidic channel networks with more than two outlet channels.
Figure 7B:
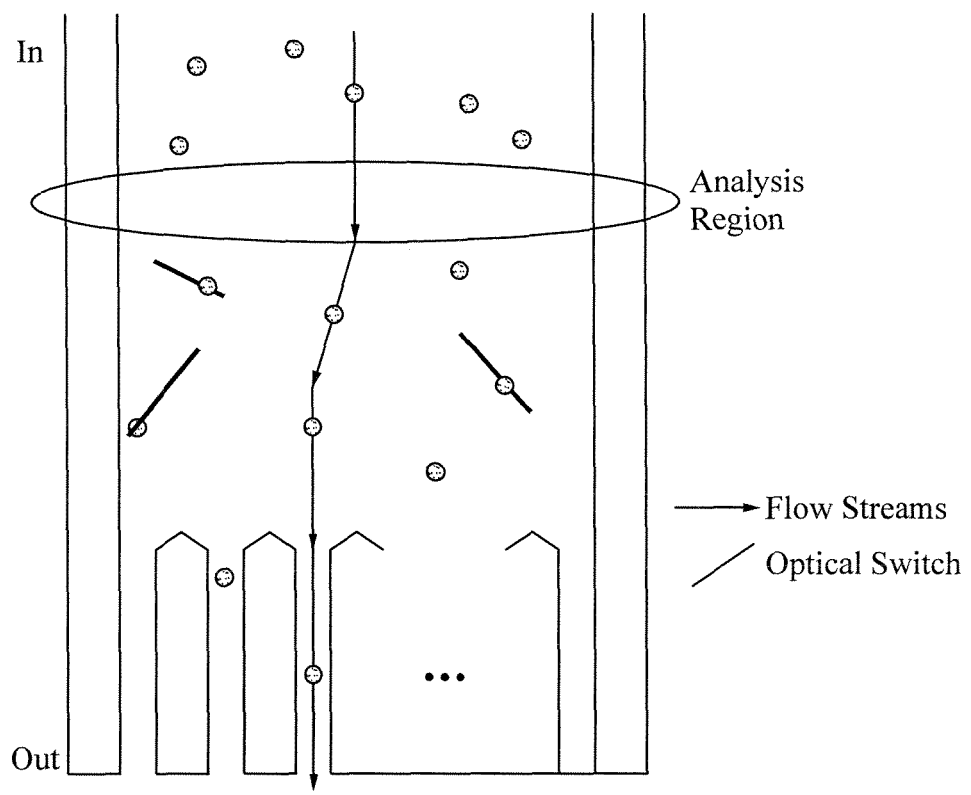
Figure 7C:
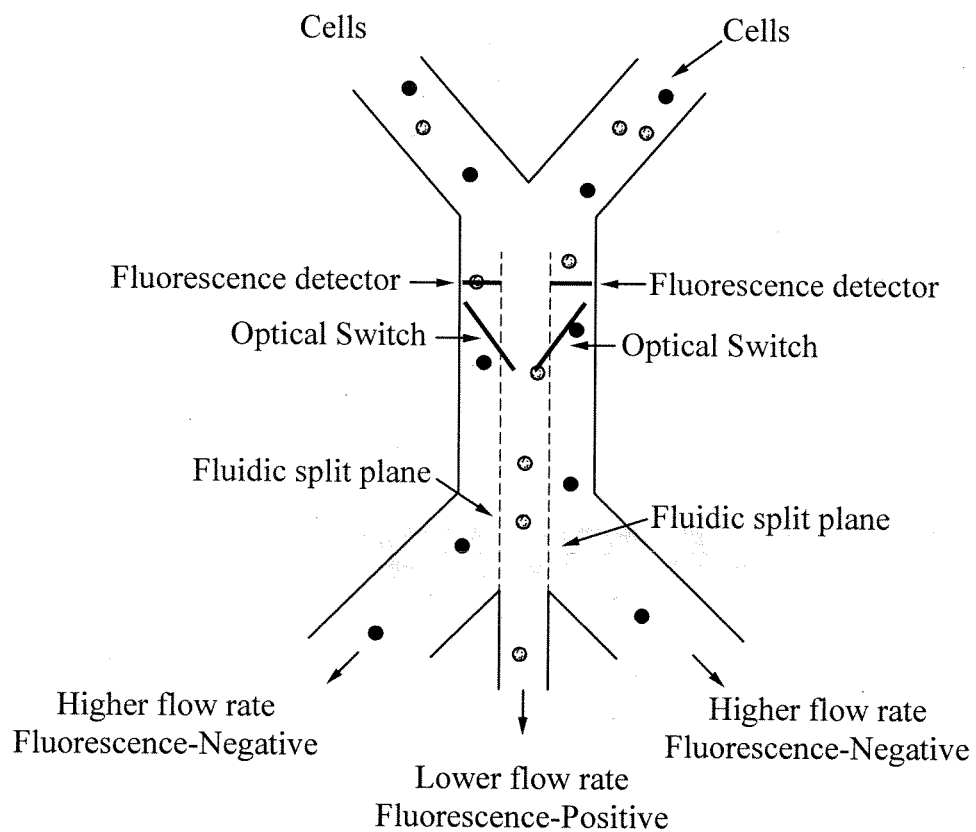

Although only the 1×2 microfluidic channel design with flow through one input main channel into a bifurcation to two output channels has been considered thus far in this description, microfluidic networks with 1×N, or M×N, outputs can be utilized. Optical or fluidic switching can be achieved in these larger networks by having an arbitrarily large number of independently modulated laser lines or independent lateral flow channels. Some embodiments are shown in FIG. 7a-c. Furthermore, cells can also be fed back multiple times through the same sorter to increase the purity of the sort, or alternatively, channels can also be arranged in a cascade for multiple levels of sorting.

Two different activation modes can be considered when operating the optical switch in a mono-directional or bi-directional arrangement; a passive mode or an active mode. The passive mode is such that the state of the optical switch is either on or off, regardless of what cell may be flowing through the channel. In this case knowledge of when or how many cells are entering the switching region is not required, and consequently, depending on the state of the laser, all cells within the switching region are switched. Alternatively, in the active mode the cells are first detected as they enter a detection/selection region, and then are switched based on some decision process. FIG. 3a-b and FIG. 4a-b show examples of this mode that use a fluorescence detector placed just prior to the switching region. In this case, all fluorescent cells were directed to one output channel, and all non-fluorescent cells were directed to the other output channel. Other non-fluorescent detection/selection techniques for the decision process include Time-Of-Flight, scatter, imaging, capacitance, or any detection modality that can identify a desired cell. Regardless of the detection/selection method, switching using the active mode can be utilized to sort one population of cells from another based on some decision process.

In order to utilize the active mode, the optical beam must be modulated on or off in response to the decision process. Regardless of the number of lasers used, or whether the optical switch is mono-directional or bidirectional, the lasers can be modulated in many ways, including using an electro-optic modulator, modulating the laser power, shuttering the laser, using a liquid crystal modulator, using a galvanometer, and using an acousto-optic modulator. For the bi-directional optical switch with two lasers, the separate lasers can be turned on and off independently; however, when using a single laser source the two different orientations of the optical switch line can be achieved by using a polarization rotator (such as a liquid crystal modulator) and having each of the two different line patterns be each of two separate polarizations. Similarly, an acoustic-optic modulator or a galvanometer mirror can be used to modulate the position of a single spot used as the optical switch, or a two-axis acousto-optic modulator or two-axis galvanometer mirror can be used to draw two different line shapes to be used as the bi-directional optical switch.

FIG. 8 shows three different possible optical designs for performing the modulation and/or shuttering of the optical switch. In FIG. 8a the bi-directional optical switch is created from a single optical beam (laser) directed toward and passing through a Liquid Crystal Modulator (LCM). The LCM is a polarization rotator and therefore if the beam is polarized in one direction it will pass straight through the Polarizing Beam Splitter (PBS), through a cylindrical lens creating a line shape, through another PBS, and then through some focusing optics which focus the line onto the microfluidic switching region. This effectively creates one line of the bi-directional optical switch used to switch cells into one of the bifurcated channel outputs. To switch cells into the other output channel a mirror image line must be created. This is accomplished by rotating the LCM which alters the polarization of the beam. Consequently, when the beam strikes the first PBS it is directed into an alternate path through a different cylindrical lens (creating a line shape), through the other PBS, which directs the beam back through the focusing optics which focus the mirror image line onto the microfluidic switching region. Note that the cylindrical lenses were used to create the line shape for the bi-directional optical switch; alternatively the cylindrical lenses can be removed resulting in spots used for the optical switch. In FIG. 8b, rather than use the combination of the LCM and PBS, with or without the cylindrical lenses, an Acousto-Optic Modulator (AOM) can be used to create the lines or spots used in the bi-directional optical switch. This is achieved by configuring the AOM to obtain the desired line shape that is required. Also, the AOM can be used to shutter the optical beam in an on/off fashion, directing the beam to a beam stop for the Optical Switch off condition. FIG. 8c shows the combination of the systems described in FIG. 8a and FIG. 8b. In any configuration that uses an AOM to vary the direction of the beam, a galvanometer mirror, either one-axis or two-axis, depending on the desired beam motion, may be used in place of the AOM.

Many variations for the optical pattern can be considered when optimizing switching efficiency for mono- or bidirectional optical switches. As mentioned above a laser line has been used as the optical switch pattern. The line might be generated by a cylindrical lens, by scanning a galvanometer mirror or an acousto-optic modulator, by a diffractive optic, by a custom refractive optic, or by any other technique. To date the line has been generated using a cylindrical lens, by scanning a galvanometer or by using an acousto-optic modulator. The length of the line can be arbitrarily long or as short as a single point. The line can have higher intensity at the top of the line and gradually taper down in intensity toward the end of the line. Additionally the line might be a curved arc which optimizes the output direction of the cells. Additionally, in real time the angle of the line or the shape of the line might vary (i.e. swivel to optimize output). For implementations with multiple output channels, any arbitrary pattern of lines in 2D space might be generated to optimize the direction of each output cell. Alternatively, the line might be created by an array of discrete spots.

Figure 9A:
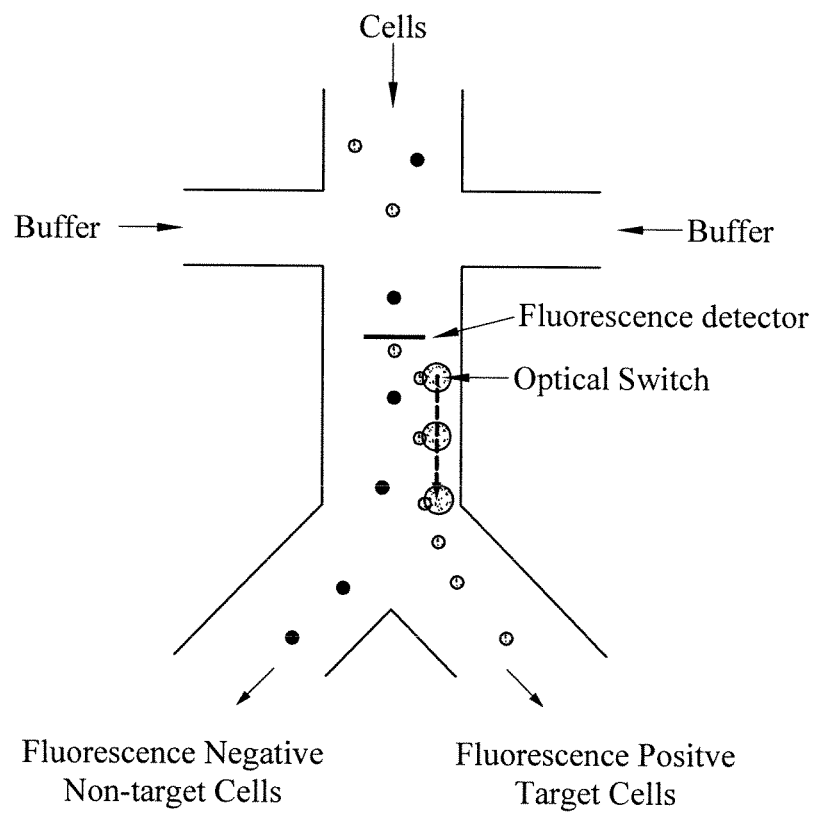
FIGS. 9a and 9b are plan views of a sheath flow skewed optical switch network with a laser spot optical switch that is translated parallel to the cell flow or at an angle to the cell flow.
Figure 9B:
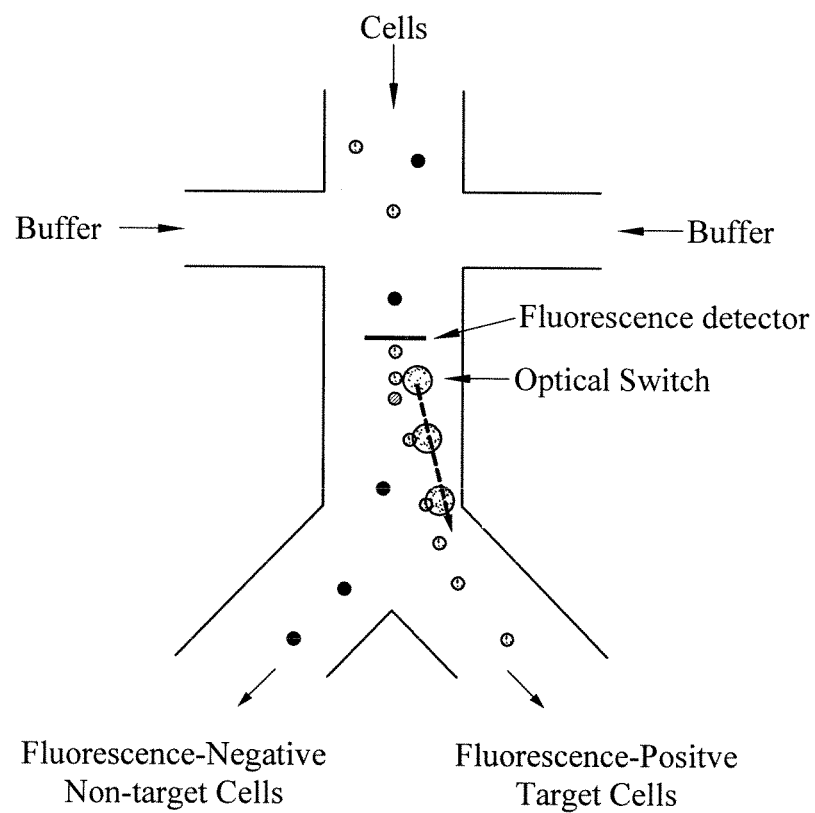

To further improve the performance of the sorting mechanism in terms of throughput, yield efficiency, and purity, the optical switch has been configured such that the laser spot is swept alongside a selected cell as it flows down the main channel toward the bifurcation junction, thereby increasing the total interaction time between the cell and the laser. The optical switch utilizes a laser spot which is translated, in a straight line, down the length of the main channel toward the bifurcation junction. The line swept by the spot can be parallel with the walls of the main channel (FIG. 9a), or can be at some angle relative to the cell flow stream (FIG. 9b). Therefore, the angle can range from 0-90 degrees. The ability to sweep the spot is achieved using either an AOM or scanning galvanometer mirrors. The optical switch is triggered to sweep by a decision based on detection of the desired cell using fluorescence or other detection modality that can identify a desired cell; for example Time-Of-Flight, scatter, imaging, or capacitance. The cell position can be either off-set or centered in the main channel, which dictates the length of the line swept by the spot and the laser power used to achieve efficient switching/sorting. Thus, as a desired cell is detected the optical switch is turned on, and the spot appears alongside the desired cell. The spot then tracks alongside the selected cell and uses optical forces to direct the selected cell into the desired output channel.

Two approaches to facilitate efficient triggering of the optical or fluidic switch are described below. Typical to both methods is the use of a temporal signal to analyze the moving cell, and use this information to generate a decision to switch, or not to switch. This temporal signal is essentially a measure of a signal as a function of time, which can yield a distinctive temporal fingerprint in terms of both peak intensity and peak width. The signal may be fluorescence, scatter (for instance, forward scatter), capacitance, imaging, or any detection modality that can identify a desired cell. One approach is to utilize a single laser source coupled with two or more detectors to accomplish both cell detection and cell identification. FIG. 10a-d show this approach using one laser source combined with a fluorescence detector and a forward scatter detector. The temporal signals from these detectors are used as the information for the switch decision. The presence of a cell is verified by the forward scatter signal and when this signal is coupled with a fluorescence signal intensity which is within a predetermined range; this "gating" information is then used to trigger the optical switch. Note that only a single fluorescence detector is shown, however multiple fluorescence detectors can be used for further refined cell identification. In the case depicted the cell stream is centrally located by using equal flow rate sheath buffers, with output channels having different widths used to create a splitting plane to the right of the cell stream. However, any configuration used to manipulate the position of the cell stream and splitting plane, as discussed above, can be used. Also, common to both configurations is the presence of an error checking detector, which verifies whether a cell has been switched or not. The detection in this case can be based on fluorescence, scatter (for instance forward scatter), capacitance, imaging, or any detection modality that can identify a desired cell.

Figure 10A:
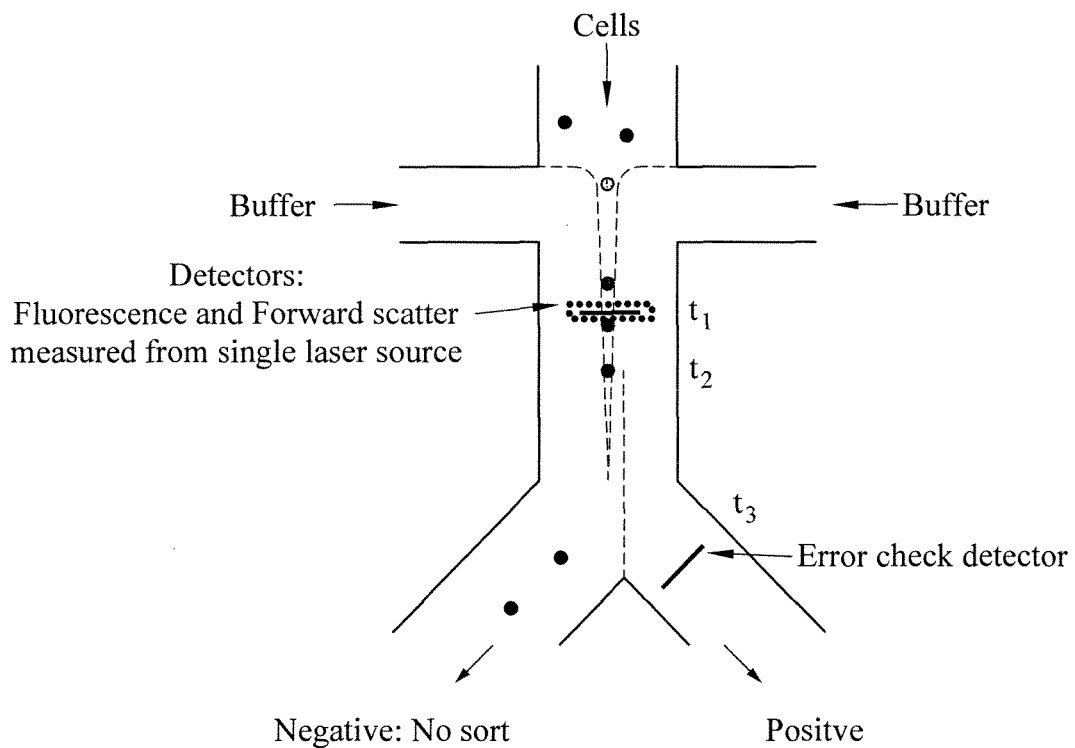
FIGS. 10a, 10b, 10c and 10d show a detector arrangement and timing/trigger diagram using a single laser source for the cell detection and trigger decision method.
Figure 10B:
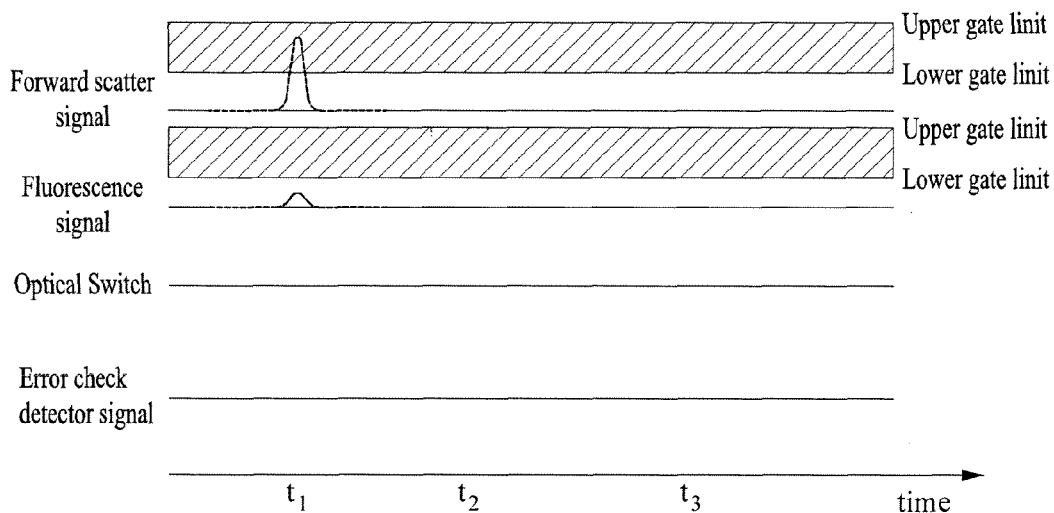
Figure 10C:
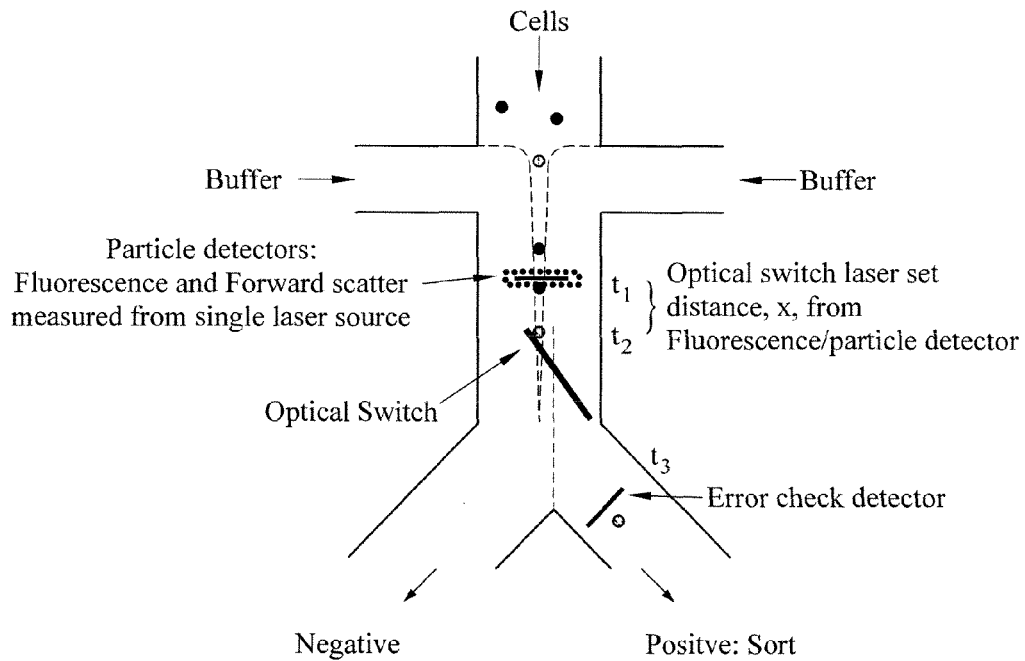
Figure 10D:
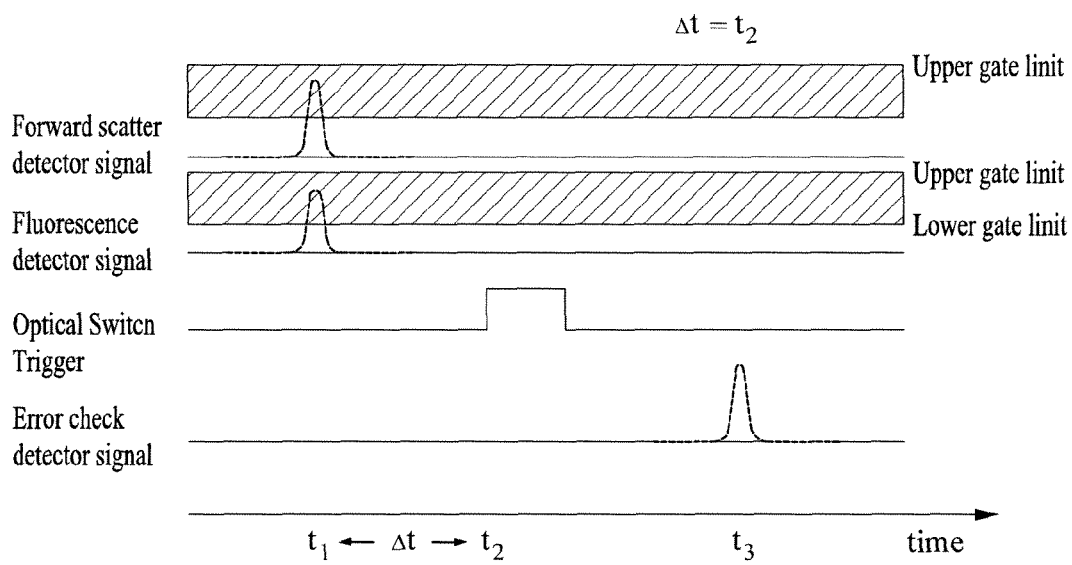

FIG. 10a-b show the detector arrangement and the timing/trigger diagram for when the sort parameter is negative and the optical or fluidic switch is not triggered. The cells enter the main fluidic channel and are focused into a single file by sheath buffer flowing from both sides. As a cell passes the through the laser in the detection/selection region, both fluorescence and forward scatter signals are detected simultaneously, or nearly simultaneously. Although the presence of a cell is successfully detected via the forward scatter signal (at time $t_1$), the fluorescence signal is below the gating level and the optical switch is not triggered (at time $t_2$). Thus, no error check signal (at time $t_3$) is obtained since no cell was switched. Alternatively, FIG. 10c-d show the detector arrangement and the timing/trigger diagram for when the sort parameter is positive and the optical or fluidic switch is triggered. Here, as a cell passes through the laser in the detection/selection region, both fluorescence and forward scatter signals are again detected (at time $t_1$) simultaneously, or nearly simultaneously, but the fluorescence signal is within the gating level and the optical or fluidic switch is triggered (at time $t_2$). An error check signal (at time $t_3$) is obtained since a cell was switched. In this approach the trigger time (at time $t_2$) is a preset value ($\Delta t$) measured from the initial detection time ($t_1$), and this $\Delta t$ value is determined by the speed of the cells and the position of the optical switch relative to the detection/selection region. This approach is satisfactory to achieve efficient sorting; however as a means to further improve the triggering accuracy a second approach is used.

FIG. 11a-d shows this second approach, in which two laser sources are used instead of one. Also, as with the single laser approach described above, the temporal signals from these detectors are used as the information for the switch decision. One laser is used in a detection zone to separately accomplish cell detection prior to the identification/selection region. The detection in this case can be based on fluorescence, scatter (for instance forward scatter), capacitance, imaging, or any detection modality that can identify a desired cell. The second laser is coupled with two or more detectors and is used to accomplish cell detection and cell identification. Again, identification in this case can be based on fluorescence, scatter (for instance forward scatter), capacitance, imaging, or any detection modality that can identify a desired cell. The purpose for two sequential cell detection steps is such that the cell flow rate can be obtained from the time difference ($\Delta t$) between the first detection (at time $t_1$) and the second detection (at time $t_2$). Knowing the spacing between detector windows (d) will yield the flow rate ($v=d/\Delta t$), and this value combined with the known distance the optical or fluidic switch is from the identification window (x) is then used to calculate the triggering time for the optical switch ($t_3=x/v$). Again switching only occurs when specific gating levels are reached for the cell identification step. Although only a single fluorescence detector is shown for identification, multiple fluorescence detectors can be used. In the case depicted the cell stream is centrally located by using equal flow rate sheath buffers, with output channels having different widths used to create a splitting plane to the right of the cell stream. However, any configuration used to manipulate the position of the cell stream and splitting plane, as discussed above, can be used. Also, common to both configurations is the presence of an error checking detector, which verifies whether a cell has been switched or not. The detection in this case can be based on fluorescence, scatter (for instance forward scatter), capacitance, imaging, or any detection modality that can identify a desired cell.

Figure 11A:
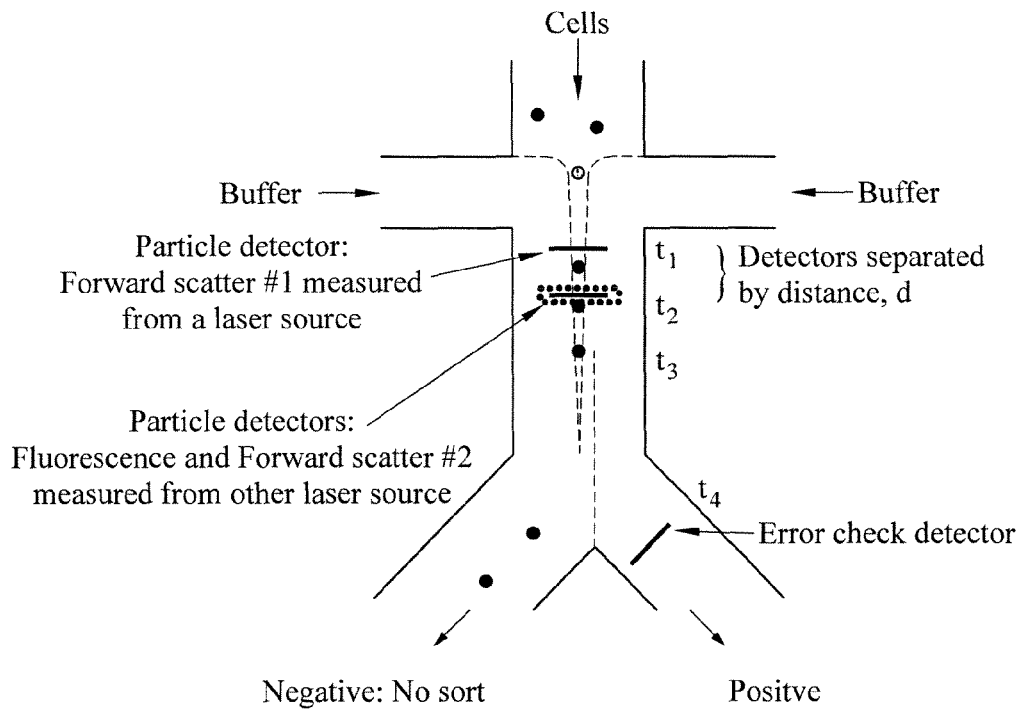
FIGS. 11a, 11b, 11c and 11d show a detector arrangement and timing/trigger diagram using two laser sources for the cell detection and trigger decision method.
Figure 11B:
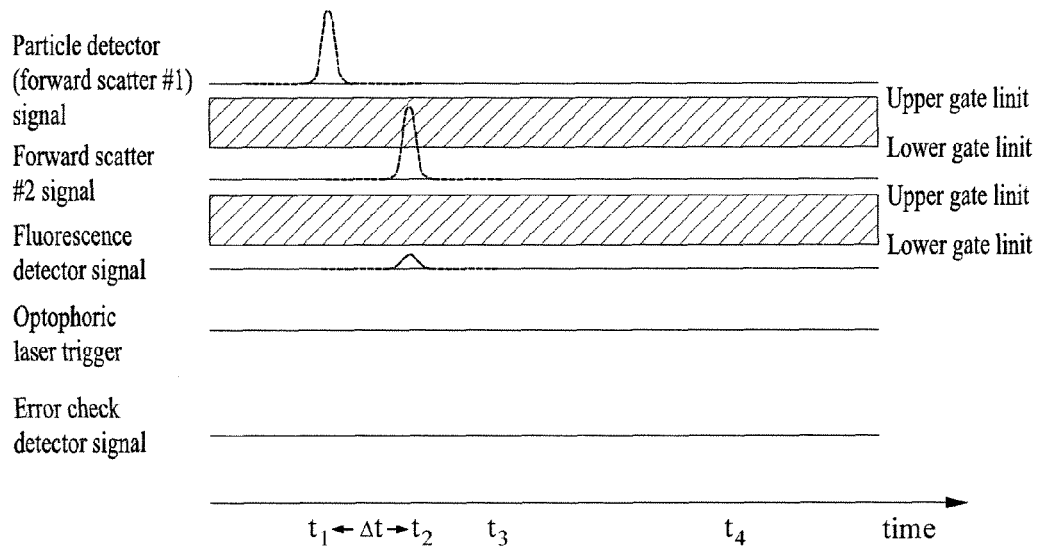

FIG. 11a-b shows the detector arrangement and the timing/trigger diagram for when the sort parameter is negative and the optical or fluidic switch is not triggered. The cells enter the main fluidic channel and are focused into a single file by sheath buffer flowing from both sides. The presence of a cell is verified by the forward scatter signal (at time $t_1$) as it passes through the detection window region. As the cell passes through the identification/selection window a second forward scatter signal is obtained (at time $t_2$), however, this signal is coupled with a fluorescence signal intensity (at time $t_2$) which is not within the gating level and the optical or fluidic switch is not triggered (at time $t_3$). No error check signal (at time $t_4$) is obtained since no cell was switched. Even without sorting a cell the flow rate (v) of the cell stream is obtained using ($t_1$), ($t_2$) and the known distance (d) between the detection and identification windows. This is obtained using the relationships: $\Delta t = (t_2) - (t_1)$ and $v = d/\Delta t$.

Figure 11C:
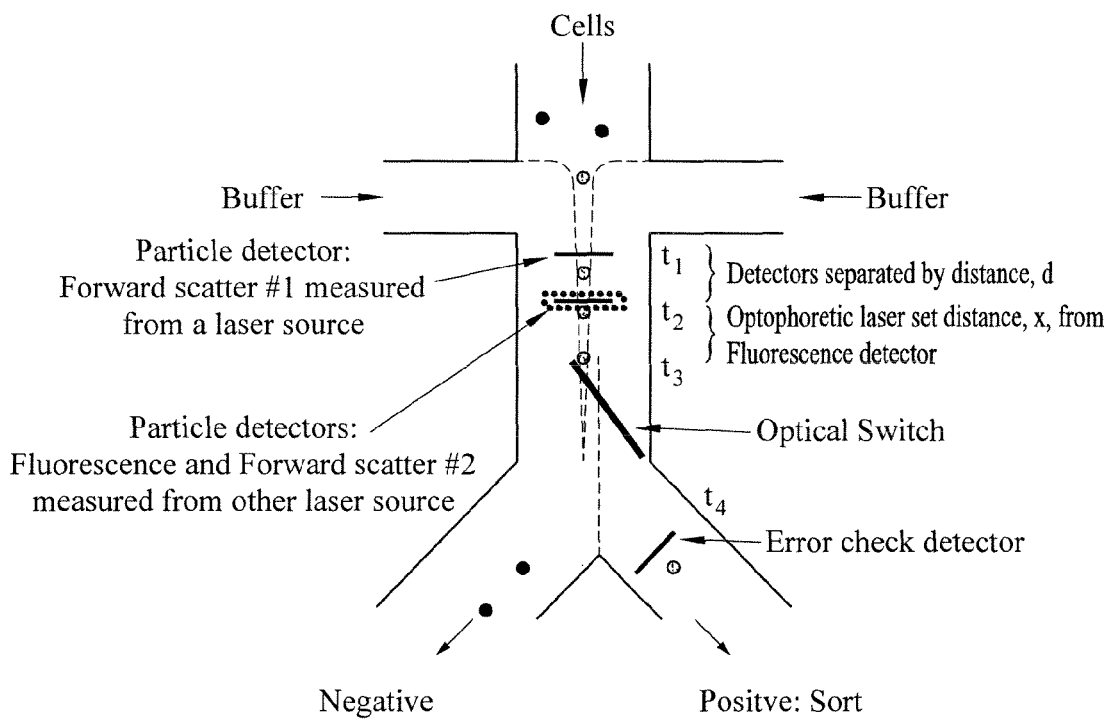
Figure 11D:
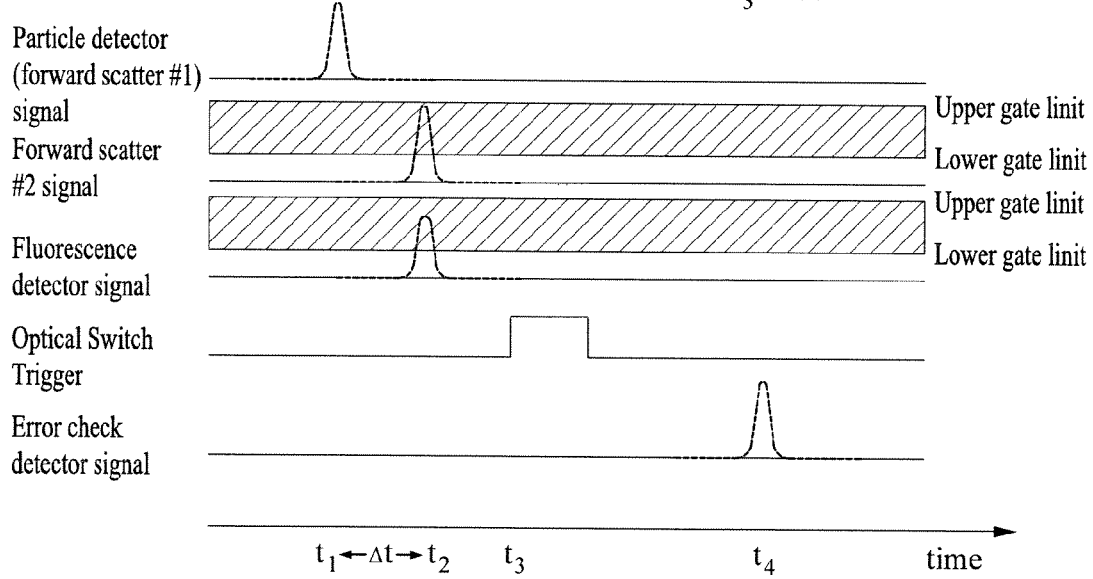

Alternatively, FIG. 11c-d show the detector arrangement and the timing/trigger diagram for when the sort parameter is positive and the optical or fluidic switch is triggered. Here, the presence of a cell is again verified by the forward scatter signal (at time $t_1$) as it passes through the detection window region. As the cell passes through the identification/selection window a second forward scatter signal is obtained (at time $t_2$), and this signal is coupled with a fluorescence signal intensity (at time $t_2$) which is within the gating level and the optical or fluidic switch is triggered (at time $t_3$). An error check signal (at time $t_4$) is now obtained since a cell was switched. In this approach the trigger time ($t_3$) is not a preset value, but rather it is calculated using the cell stream flow rate (v) and the known distance (x) between the optical switch and the identification window. This is obtained using the relationships: $\Delta t = (t_2) - (t_1)$; $v = d/\Delta t$; $(t_3) = x/v$. This approach allows for more efficient sorting as it can account for fluctuations in cell flow rate, and therefore more accurately trigger the optical or fluidic switch. An added benefit of this approach for optical switching is, for each individual cell, the possibility of adjusting the rate at which the laser spot is translated down the channel such that it matches the velocity of the cell as determined above, thus maximizing the interaction time between the cell and the laser spot of the optical switch. The translation velocity of the laser spot would be varied by varying the driver for the AOM.

Another approach to improving the sorting efficiency, while incorporating the triggering approaches described above, is to centralize the cells in the main channel using channel designs which create a true sample core, whereby the core is completely surrounded by the sheath buffer. Variability in the location of a cell along the channel height can cause variability in cell detection and fluorescence intensity. Ensuring that the cells are in a core flowing in the center of the main channel may improve sorting efficiency, since this minimizes any variability due to radial distribution of cells, and controls the distance the cell needs to be moved to effect efficient sorting. Such a core flow can be achieved with a 2-dimensional pinch of the input flow stream with sheath buffer.

Figure 12:
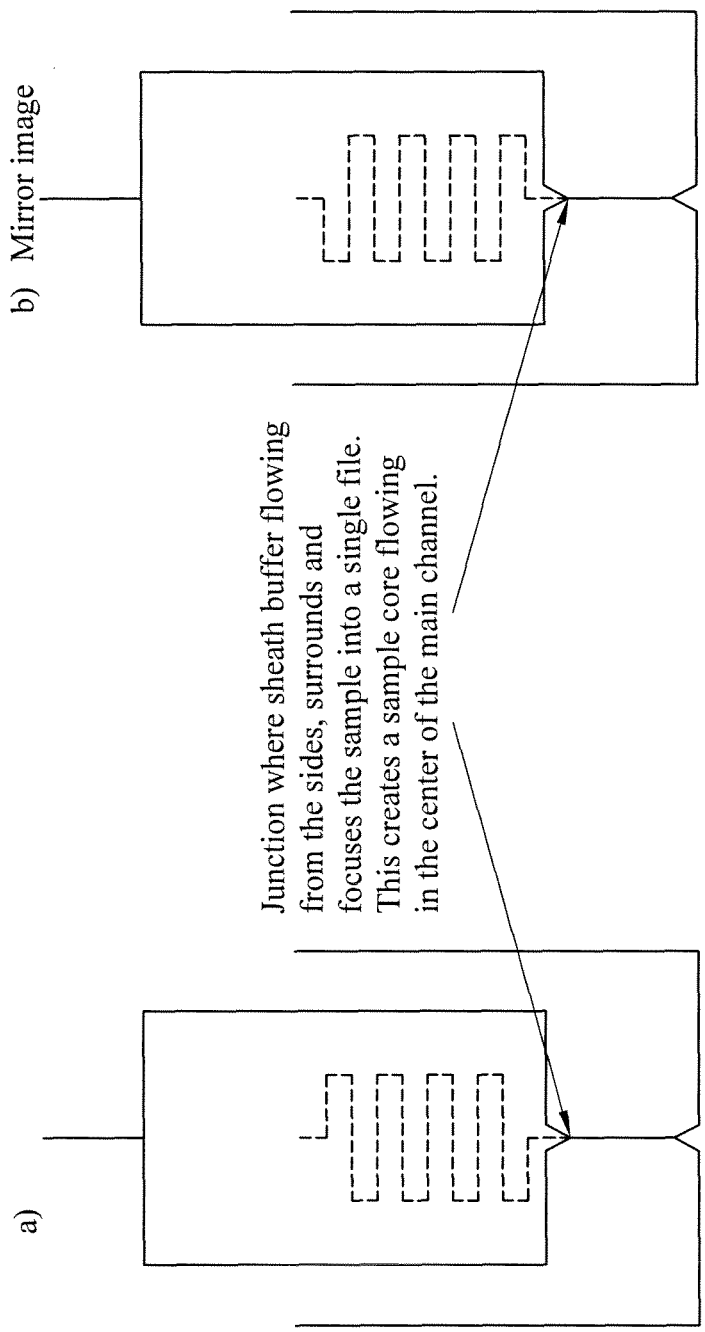
FIG. 12 is a schematic of a representative design for photolithography masks for microfluidic channel networks in both bottom and top glass substrates that provides a 2-dimensional sheath flow pinch of the cell flow in the main channel when these substrates are bonded to form a single network.
Figure 13:
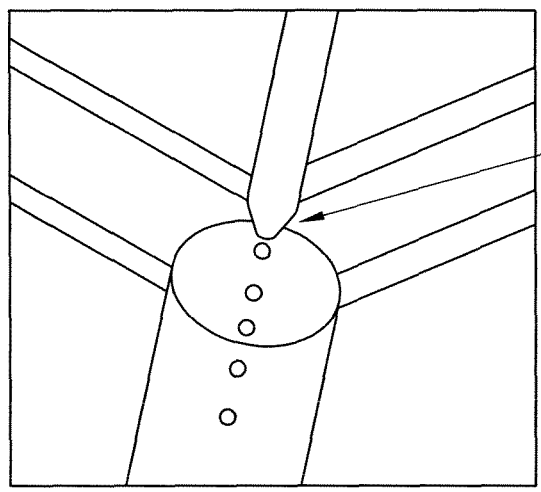
FIG. 13 shows a 3-dimensional illustration of the design described in FIG. 12.

This approach requires a bottom substrate and a top substrate; each with microfluidic channel networks formed in them. FIG. 12a-b and FIG. 13 show one method to accomplish this, in which the channel design on one substrate is the mirror image of the design on the other substrate. Thus, when the two substrates are brought together, with the channel designs facing each other, the channel networks overlay and form complete fluidic conduits. FIG. 12a-b show one type of design used in this approach, with the sample channel shown as a dashed line. The key feature of this approach is to ensure that the sample channels are shallower than the sheath channels, such that when the substrates are brought together the sample conduit appears to enter the junction as a hole. This is shown in FIG. 13, where the cells can be seen to enter the junction, and then are pinched from all sides creating a sample core which flows in the center of the main channel. Note that the channels can be formed by wet chemical etch or laser etch of glass or quartz, by molding or embossing in plastics or polymers.

Another method involves having a series of intersecting channels arranged such that in the first junction/intersection the cells are pushed vertically toward one wall of the main channel, the next junction/intersection forces this cell stream vertically into the center of the main channel, and then a final pinch flow from both sides at a third junction/intersection creates the complete sheath buffer shroud around a sample core flowing in the main channel. This is shown in FIG. 14 and FIG. 15, with one possible channel schematic shown in FIG. 16. In this example, at junction (A) sample flows from the top substrate into the junction and down into the channel in the bottom substrate, where the side sheath buffer flows into the junction from the sides. The sample is slightly focused and pushed to the top wall of the bottom channel as it continues to flow toward the next junction (B). At junction (B) the sample flows along the top of the bottom channel from junction A to junction (B). Here a second sheath buffer flows into the junction (B) from the top substrate and the sample is pushed down to the middle of the channel in the bottom substrate. The sample continues to flow along the middle of the bottom channel toward the next junction (C). Here a third sheath buffer flows into junction (C) from both sides, and the sample is pinched into single file. The sample is now surrounded by sheath buffer as it continues to flow, as a sample core, centered both horizontally and vertically within the main input channel.

Another method uses a shallow channel in the axis orthogonal to the 1-D sheath buffer to minimize the effects of a parabolic velocity dispersion. In one-dimensional flow focusing in microfluidic channels, particles or cells in the inlet center stream are pinched along only one direction. In the direction perpendicular to the pinch and the direction of flow, a parabolic velocity profile remains. Particles near the center of channel flow fast while ones close to channel wall flow slow. As a result, particles or cells travel down the flow channel with a distribution of velocities, which complicates synchronization of detection and switching events. FIG. 34 shows a method to overcome the intrinsic problem in 1-D microfluidic flow focusing, but using a channel depth comparable to size of particles or cells in the orthogonal direction. For example particles or cells with a diameter of 10 micrometer, channel depth can be 15 micrometer. In this case, the particles or cells occupy most the channel in the depth direction, so that they experience a velocity that averages out the velocity distribution and narrows the velocity dispersion in the channel.

All of the microfluidic channel network designs described in FIGS. 1-16 have been produced in glass substrate utilizing conventional photolithographic masking and isotropic etching of the masked glass substrates. The isotropic etch typically produces microfluidic channels that have a depth $d_e$ at the center of the channel and a width $w = w_p + 2 \times d_e$ at the top of the channel, where $w_p$ is the width of the photolithography pattern that defines the channel. The bottom profile of the channel has a quarter-round contour of radius $d_e$ at each edge due to the isotropic etch and the top of the etched channel is open. A glass substrate, typically a glass cover slip, is thermally bonded to the substrate with the etched microfluidic channels to seal the tops of the channels and complete a microfluidic channel network. Holes are typically drilled in the top substrate prior to the thermal bonding to provide vias for ingress and egress of fluid flow to the microfluidic channel network, but alternately, holes also could be drilled into the etched bottom substrate rather than the top substrate. The depth $d_e$ of the channels depends on the rate of the chemical etch process and the duration of the etch step. The depth of the microfluidic channels is typically in, but not limited to, the range 10 µm to 100 µm. The width of the microfluidic channels is typically, but not limited to, 2 to 5 times the depth. This is achieved by using lines on the photolithography mask that are typically, but not limited to, the range 5 µm to 400 µm. As mentioned previously, other substrates may be used, such as plastics or moldable or castable polymers. In these cases, the microfluidic channels typically have rectangular cross sections, but otherwise are similar to the channels in the glass substrates. The size of the glass substrate in which the microfluidic channel network is produced is typically in, but not limited to, the range of 5 mm×5 mm to 25 mm×50 mm with a total thickness in, but not limited to, the range 500 µm to 2 mm. The top substrate is typically the same size, with thickness in, but not limited to, the range 300 µm to 1 mm. The vias are typically, but not limited to, 200 µm to 600 µm in diameter. The completed substrate, with a microfluidic channel network and a bonded cover plate with vias for fluidic ports for ingress and egress of fluid flow, is termed a microfluidic sorting chip or chip for brevity.

The microfluidic channels networks shown in FIGS. 1-16 typically have only described the local geometries of the inlet microfluidic channel, the sheath buffer pinch junction channels, the cell identification and optical switch main channel, and the bifurcation of the main channel to the outlet channel. This description needs to be expanded to provide for regions in each channel to make the connections to reservoirs in a macro-scale fluidic device or cartridge that provides the interface to the vias described above to provide ingress and egress of the fluid flow from the network. The cross section and length of each of these microfluidic channels typically needs to be adjusted to assure appropriate controlled flow within the entire microfluidic channel network, depending on the technique selected to achieve the flow in the channels. Both the cross section and the length of these channels are determined by the pattern used to produce the photolithography mask.

Figure 17:
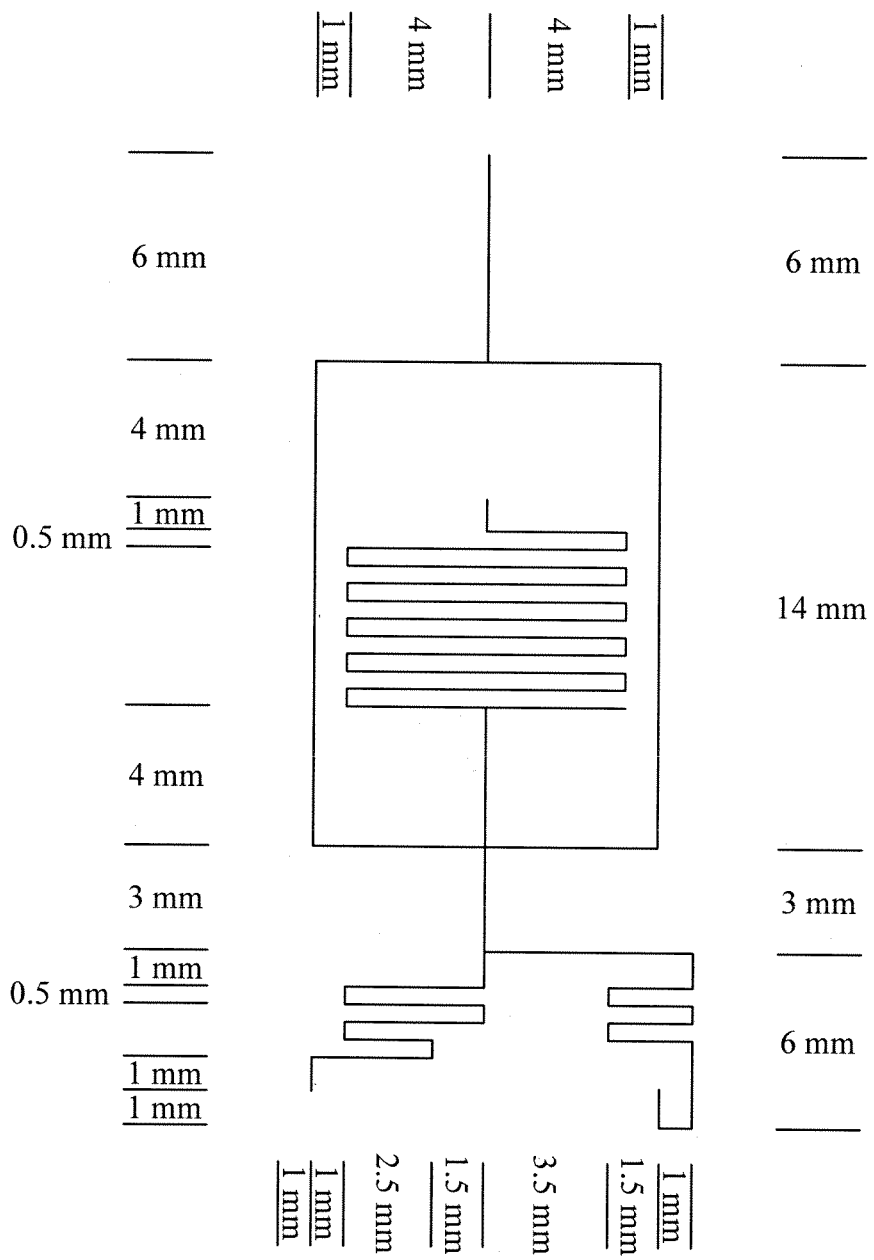
FIG. 17 is a representative embodiment of a photolithography mask for a complete microfluidic channel network, with a T-pinch junction and a T-bifurcation junction to the outlet channels, to implement the optical switch based cell sort method.

FIG. 17 shows one embodiment of a mask for a complete microfluidic channel network that has an inlet channel, two sheath channels to a T-pinch junction and two outlet channels from a T-bifurcation junction. This mask was designed to provide a 7:1 volumetric pinch ratio (the sheath flow rate is seven times greater than the cell inlet flow rate). The length of the channels was designed to provide both sufficient pressure drop to enable the use of either standard low flow syringe pumps or low pressure pneumatic controllers to establish the flow. The design also reflects the balance of pressures needed to enable use of only two pumps, one for the cell inlet channel and one for the two sheath channels, with the outlets maintained at atmospheric pressure. The sheath channel inlet is at the termination at the top of the design, the cell inlet channel originates below this in the center of the two sheath channels and is long enough to provide the appropriate pressure drop to set the 7:1 pinch ratio, and the two outlets are located at the termini at the bottom left and right.

Figure 18:
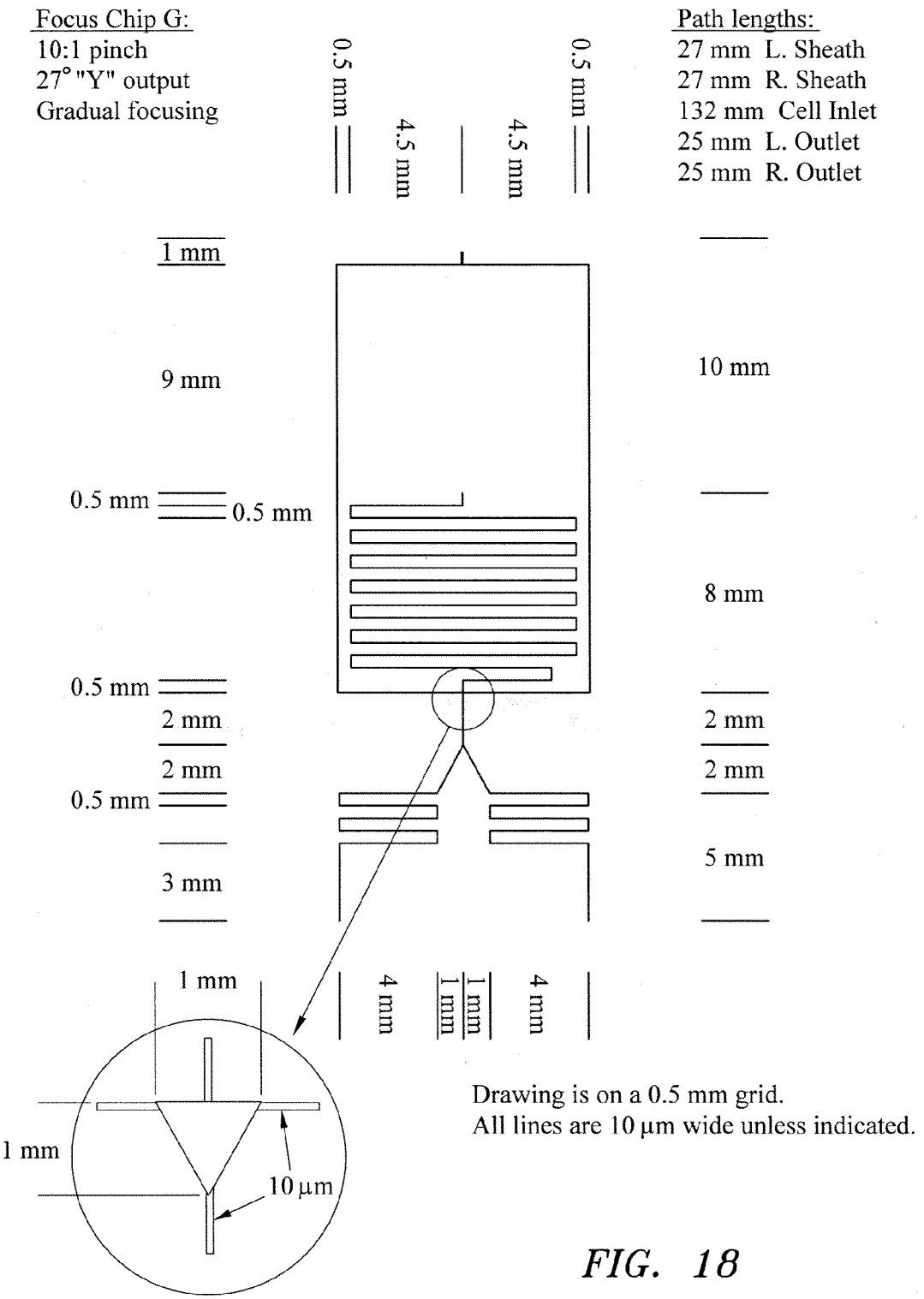
FIG. 18 is a representative embodiment of a photolithography mask for a complete microfluidic channel network, with a triangle-pinch junction and a Y-bifurcation junction to the outlet channels, to implement the optical switch based cell sort method.

FIG. 18 shows another embodiment that incorporates a triangular junction for the pinch junction and a Y-bifurcation junction, in a design that provides a 10:1 volumetric pinch ratio. Otherwise the design is geometrically similar to that of FIG. 17. Many other designs are clearly possible, but they all share the common features of needing to provide for fluidic ingress and egress and to provide appropriate pressure drops and pressure balances for the method chosen to establish the fluid flow. Similar design conditions are used to produce the photolithography masks used to make the microfluidic channel networks for 2-dimensional pinch flow networks described previously.

Figure 19:
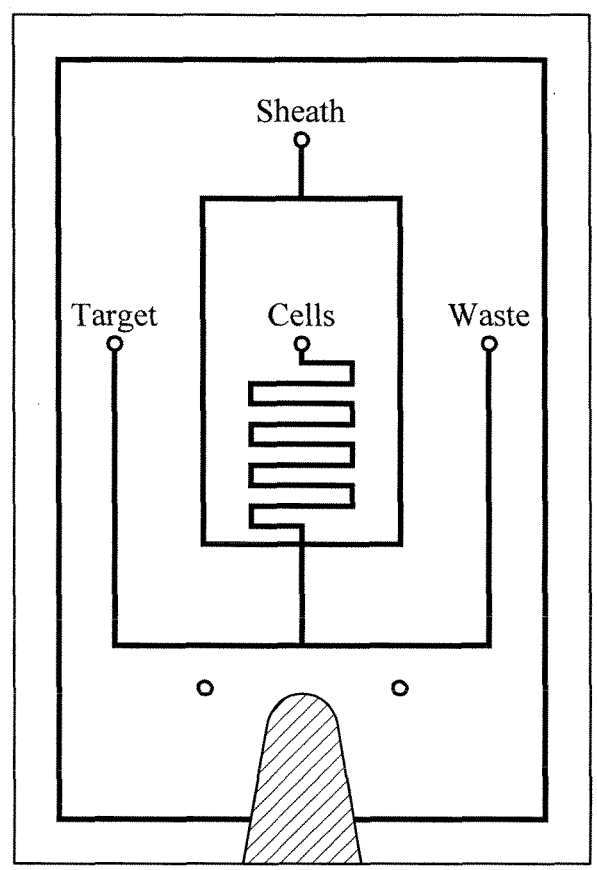
FIG. 19 shows a preferred embodiment of a microfluidic channel network in a completed microfluidic cell sorting chip.

FIG. 19 shows a preferred embodiment of a microfluidic channel network in a completed microfluidic sorting chip. The two inlet ports, for the cell sample flow and for the sheath buffer flow are identified, as are the two outlet ports, for the fluorescence-positive target cells and for the fluorescence-negative non-target cells, the waste stream. The chip is 24 mm by 40 mm. The thickness of the etched substrate is 1.1 mm. The thickness of the bonded cover plate is 550 µm. The microfluidic channels are 50 µm deep. The cell inlet microfluidic channel is 110 µm wide. The sheath flow and outlet microfluidic channels are 150 µm wide, as is the main microfluidic channel. The sheath flow pinch junction is an inverted equilateral triangle, 300 µm per side, connecting the cell inlet channel through the base of the triangle, at the top of the junction, with the two sheath flow pinch channels from each side to the main channel through the apex of the triangle, at the bottom of the junction. This microfluidic channel network design is optimized to use pneumatic control of the flow at all four ports to establish the network flow.

Microfluidic connections to the chip may be made in a variety of ways. One method is to use flexible microfluidic tubing directly connected to the ports, either by gluing or using various tubing adapters that can be attached to the surface of the chip at the ports. This tubing can be connected directly to syringe pumps or similar systems that provide volumes for handling both the cell sample and the sheath buffers and provide the pressure to flow these volumes through the chip. Using the syringe pumps for handling the sample volume requires that the pump be cleaned and reloaded for each sample and introduces the possibility for carry over or contamination from one sample to the next.

An improved method for microfluidic connections to the chip utilizes a cartridge that is directly adhered to the chip using a UV-curable adhesive, a PSA (pressure sensitive adhesive) bonding sheet, or other conventional bonding methods, such as thermal bonding. The cartridge has four built-in reservoirs that separately provide interface connections to the cell inlet channel, the two sheath channels (from one reservoir), and each of the two outlet channels. Such a cartridge provides the possibility of sterile handling of both the cell sample and the sorted target cells and waste stream, since they can be completely confined to the volumes of the cartridge before and after the cell sort. The flow for such a cartridge and chip system can be provided by using two pneumatic pressure controllers that separately pressurize the cell inlet and sheath buffer reservoirs to induce flow through the microfluidic channel network of the chip to the outlet reservoirs that are at atmospheric pressure.

An improved flow control method is provided by using four pneumatic controllers that separately pressurize each of the cell inlet, sheath buffer, target cell collection and waste collection reservoirs. Such a flow control system provides the ability to separately adjust the volumetric pinch ratio at the sheath pinch junction, the flow velocity of the cells in the main microfluidic channel for the fluorescence analysis and optical switch, and the split ratio at the switching bifurcation to enable biased flow, as described previously.

Figure 20:
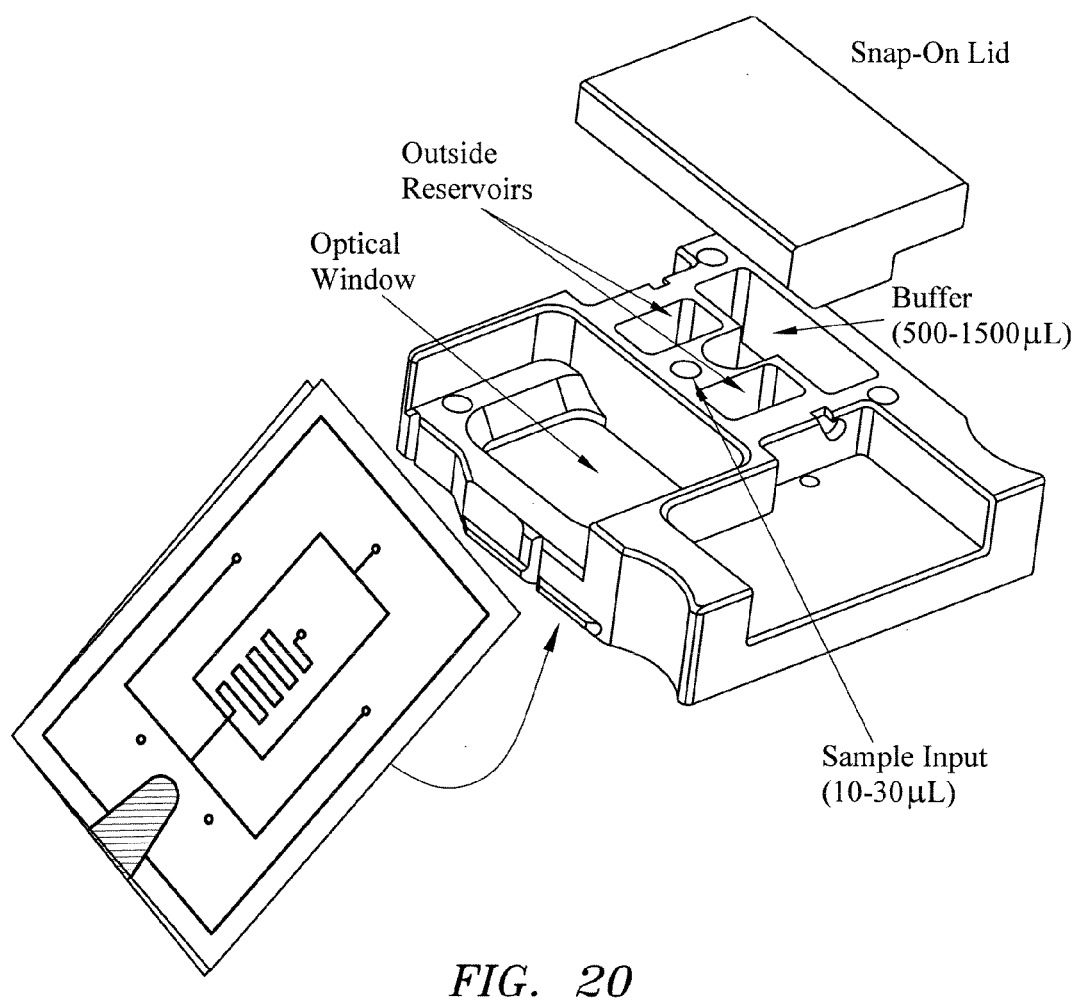
FIG. 20 shows a preferred embodiment for a self-contained disposable cartridge for the optical switch based microfluidic channel network cell sorter.

FIG. 20 shows a preferred embodiment of a self-contained disposable cartridge that provides fluidic reservoirs for the cell sample volume, the sheath buffer volume and the two outlet collection volumes for target cells and waste respectively. The cartridge is manufactured from acrylic plastic and may either be machined or cast. Other plastics or suitable materials may be substituted for acrylic if appropriate. The cell sample volume is typically conical in shape, tapering towards the port to the inlet microfluidic channel. In the preferred embodiment, the inlet reservoir contains a polypropylene insert to minimize cell adhesion and consequently maximize cell yield. The chip is bonded with UV adhesive to the optical window region, and the outlet ports from the chip interface with their respective reservoir volumes. The reservoir volumes are sealed with the snap-on lid that has drilled ports for connection between the pneumatic controllers and the individual reservoirs. The lid contains a silicone gasket to aid in sealing against the cartridge body. It also incorporates a 0.1 µm polypropylene filter to create a gas permeable, liquid tight interface between the cartridge volumes and the external environment. This maintains aseptic conditions on the cartridge and minimizes any biohazard contamination to the user or the instrument.

The cartridge is prepared for a cell sorting run by first priming the microfluidic channel network through the sheath port with sheath buffer solution, using an ordinary syringe with a luer fitting. In this way the channels are primed and the sheath reservoir is filled with 800 µl and each outlet reservoir is filled with 200 µl. The cell sample reservoir is aspirated of excess buffer liquid and then 5-25 µl of cell sample is placed into the sample input reservoir using a pipette. The cartridge lid is then applied and snapped into place, providing a self-contained system in which to perform the cell sorting run.

The cartridge is designed to be placed in a holder that positions the main channel of the chip such that the optical imaging system that projects the optical switch beam into the channel is appropriately aligned and focused into the channel. The cartridge holder also includes a pressure manifold plate that has four to six ports, connected by external tubing to the four pneumatic controllers. Each manifold port is sealed to its respective cartridge lid port with an o-ring, and these seals are made leak free by pressing the manifold against the cartridge lid with a cam-lock mechanism. FIG. 29 shows a preferred embodiment for a cartridge holder for fluidic switching that integrates two pneumatic valves on the manifold in order to shorten the volume and path length of the pneumatic pulse. The manifold coupling pneumatic pressure from a source to the pneumatic pressure port is done without intervening tubing. This allows faster switching speeds for higher performance and supplements the performance gain from the switch configurations shown in FIGS. 27-28.

Figure 21:
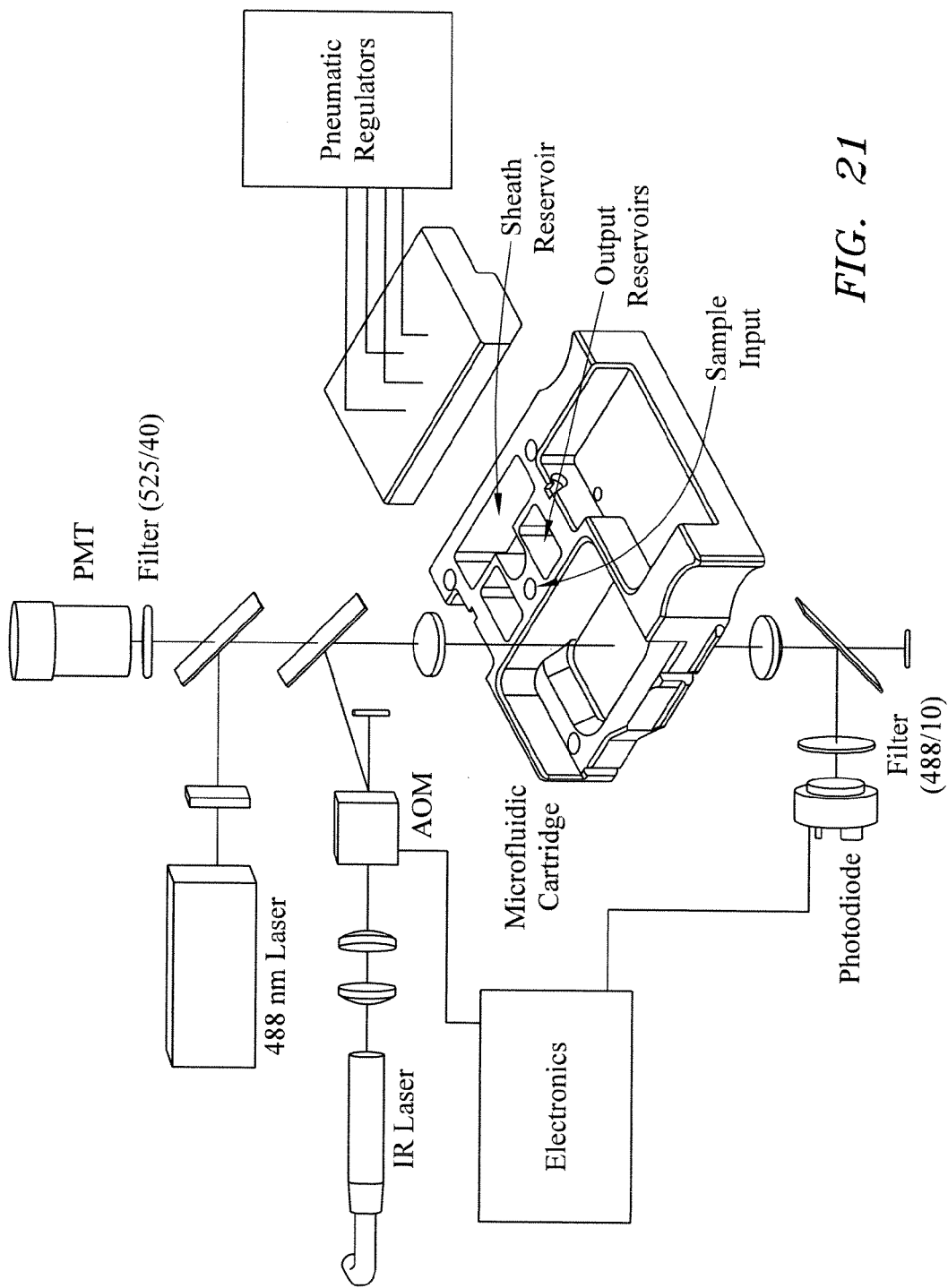
FIG. 21 shows a preferred embodiment of the optical system for the optical switch based microfluidic channel network cell sorter.

A preferred embodiment of the optical system for the optical switch is shown in FIG. 21. The cartridge, with the pneumatic manifold connecting to the snap-on lid, is positioned such that the optical switch region is at the focus of both a lens system viewing from above the cartridge and a lens system viewing from below. The output beam from a 488 nm laser is projected through the imaging system into the main channel just upstream of the sorting region, as shown in FIGS. 3-7 and 9-11, to provide excitation for the detection of fluorescence from fluorescence-positive target cells. The fluorescence emission is collected by the same lens and imaged through a dichroic mirror and an appropriate fluorescence emission filter to a photomultiplier tube. The signal from the photomultiplier tube is processed by the electronics to measure the level of the fluorescence from the cells and determine the presence of fluorescence-positive target cells in the flow stream in the main channel. The fluorescence excitation is not limited to the 488 nm wavelength, but can be at any wavelength that is appropriate for the fluorophores used to identify the target cells. If a different excitation illumination is used, the wavelength of the fluorescence emission filter must be changed accordingly. When fluorescence-positive cells are identified, the electronics triggers the AOM to direct the beam from the IR-laser, typically a 1070 nm laser operation between 5 W and 20 W output power, into the main channel at the optical switch position. In the preferred embodiment, the AOM is controlled to produce an optical switch pattern as described in FIG. 9b, although any of the optical switch methods previously described could be implemented. The lens below the cartridge images the 488 nm excitation illumination onto a photodiode. The signal detected by this photodiode is used to help distinguish fluorescently labeled cells from smaller debris that may carry the fluorescent label, and also to identify clumps of cells that might have formed. These events are rejected as candidates for sorting to the target output channel.

Yet another preferred embodiment would incorporate appropriate imaging and optical filtering to provide a forward scattering signal based on the illumination of the cell by the 488 nm laser that is used to excite the fluorescence. The optics would provide a range of angular sensitivity, such as, but not limited to this range, 0.8° to 10°, for the detection of the forward scattering signal. This signal can help characterize cells in addition to the fluorescence signal, as well as help distinguish cells from debris. The forward scattering illumination is not limited to the fluorescence excitation laser, but could be at any other wavelength provided by an additional light source that is properly imaged into the main channel.

Yet another preferred embodiment would incorporate additional fluorescence detection channels that are sensitive to fluorescence emissions at different wavelength, typically using a single excitation wavelength, such as, but not limited to, 488 nm. Each detection channel would incorporate a PMT with an appropriate dichroic mirror and emission filter for the fluorescence emission wavelength of the additional fluorophore. From two to four fluorescence detection channels are readily accommodated in this manner. Using more than one fluorophore in this manner provides the ability for multiple detection criteria to identify the target cells for sorting with the optical switch.

Yet another preferred embodiment would incorporate an error checking capability that provides optical illumination, typically as a narrow line across one of the channels in the network, and typically at a longer wavelength, perhaps, but not limited to, 785 nm from a solid state laser, that is outside the range of wavelengths used for fluorescence detection and forward scatter detection, but is shorter than the optical switch wavelength that is typically at 1070 nm. This source can be appropriately imaged into the microfluidic channel network to provide lines that can be used to detect passage of particles through any vertical plane in the network. This provides additional ability to check the performance of the optical switch performance and provides additional capability for the timing of the trigger of the optical switch, as described in FIG. 11.

Yet another preferred embodiment of the optical system would incorporate an additional optical illumination path at, but not restricted to, 750 nm, e.g., as produced by band pass filtering the light from an LED, and illuminating a region of the microfluidic channels with that light. That region would be imaged through a 750 nm pass filter onto a CCD camera to provide visualization of the performance of the cells flowing in the microfluidic channel network at the bifurcation junction and/or at the pinch junction. The filters before the camera would be adequate to block any shorter wavelength radiation associated with the excitation or detection of fluorescence and with the forward/side scatter optics and the error detection optics. The filters would also block the longer wavelength, 1070 nm light from the optical switch.

The preferred embodiment of the cartridge shown in FIG. 20 is designed to hold the microfluidic channel network in a horizontal configuration, so that all of the channels and inlet/outlet ports are at the same vertical level. This minimizes the effects of gravity on the pressure drops through the microfluidic channels, leading to more stable and controllable flow in the network. However, gravity will still have an effect on the cells in the flow, particularly as the cells pass from the cell sample reservoir into the cell inlet microfluidic channel. Another preferred embodiment of the sorter, to help control the effects of gravity on settling of the cells in this reservoir and on their settling in the relatively slower flow in the inlet microfluidic channel before the cells flow speeds up at the pinch junction, is to enhance the buoyancy of the cells, such that settling of the cells is minimized. Increasing the buoyancy can be achieved by using additives in the sample buffer. Examples of these rheological control additives, particularly those that are either pseudoplastic or shear thinning, or both, are xanthan gum, carageenan, sodium carboxymethylcellulose, methylcellulose, hydroxypropylmethylcellulose, hydroxyethylcellulose, hydroxypropylcellulose, hydroxypropyl guar, Gum Arabic, Gum Tragacanth, Alginate, polyacrylates,carbomer. Other additives include Histopaque™, which is a mixture of polysucrose and sodium diatrizoate, and Optiprep™, which is a 60% w/v solution of iodixanol in water. The concentration of these additives used depends on the density of the cell being sorted. For instance, in the case of Optiprep™ the concentration can range from 5% to 40%. Finally, salinity of the sample buffer and addition of sucrose can also be used to adjust the buoyancy of cells.

The buffers that are used for the cell sample volume and for the sheath flow can be any buffers that are biologically compatible with the cells that are being sorted, and are compatible with optical illumination that is used both for the fluorescence detection modality and for the optical switch, i.e., the buffer has sufficiently low absorbance at the fluorescence excitation/detection wavelengths and the optical switch wavelength. A preferred embodiment of the sheath buffer uses PBS/BSA, phosphate buffered saline (PBS) at pH 7.2 with 1% bovine serum albumin (BSA) fraction 5. A preferred embodiment of the cell buffer uses PBS/BSA with 14.5% Optiprep for live cell samples and 27% Optiprep for a variety of formalin fixed cell samples.

The performance of the optical switch method of cell sorting in a microfluidic channel network is evaluated by the throughput, purity and recovery of the sort as previously described. The cartridge described in FIG. 20 is optimized to allow measurement of the performance, since it is made of acrylic, the bottoms of the target and waste collection reservoirs are transparent and the cells that are sorted into these reservoirs can be quantified as to both number and fluorescence labeling using an inverted fluorescence microscope. Several of the switching configurations described in FIGS. 3-11 were evaluated. These evaluations were performed using a 50:50 mix of live HeLa:HeLa-GFP cells that was sorted using either a 1- or 2-sided stationary laser spot, or a 0° or 8° 1-sided laser sweep. The laser was swept at 240 Hz. The laser ON time was 4 msec and the laser power was 20 W for all switch modes. For the swept spot method, the focused IR laser spot was translated about 70 µm along the main channel.

Figure 22:
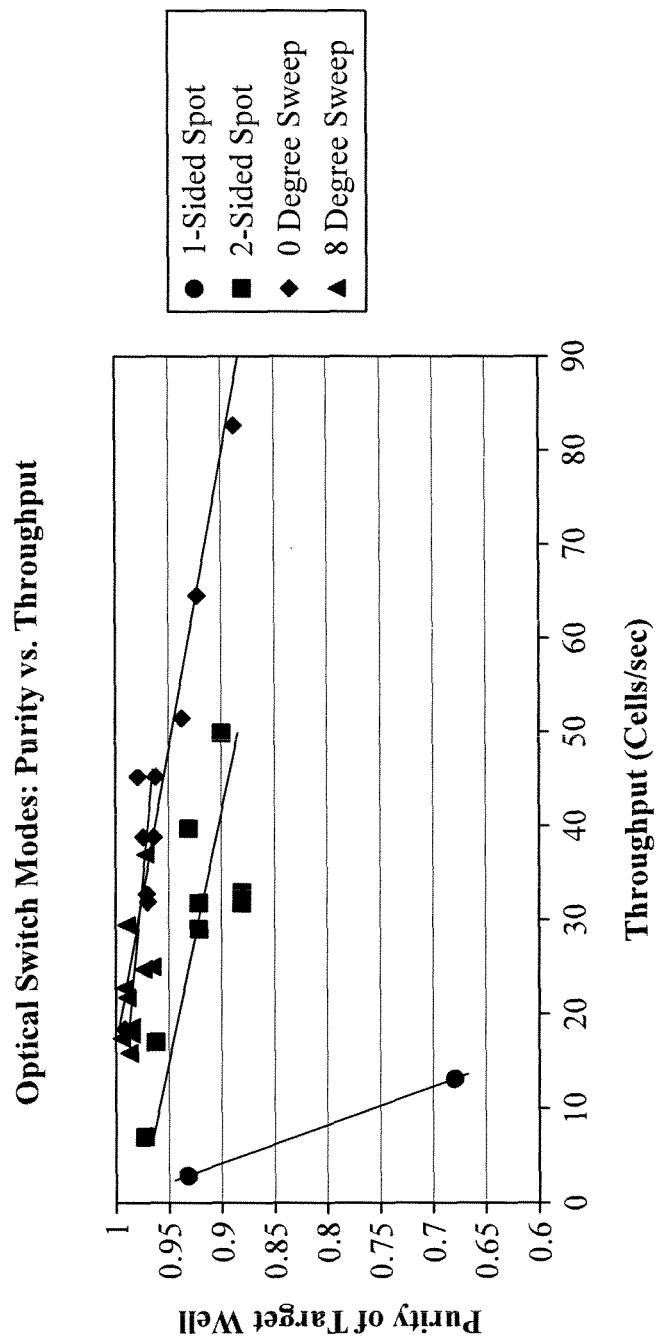
FIG. 22 shows representative performance of the optical switch based microfluidic channel network cell sorter for various implementations of the optical switch.

As shown in FIG. 22, the bidirectional optical switch with laser spots, described in FIG. 6, gave good results for purity and recovery for the 50:50 mixes of target:non-target cells up to a throughput of 50 cells/s. However, at lower subpopulation concentrations (data not shown), it was not an efficient use of laser power to switch non-target cells, and coincidence errors increased at higher cell throughput rates. Additionally, small particulates that were not switched would contaminate the target reservoir.

FIG. 22 also shows the performance of the 1-sided switching methods, described in FIG. 9, with a stationary laser spot or a spot that is translated in the direction of flow, either parallel or at a slight angle to the flow. The sample core flow stream was biased to the waste outlet such that all the cells went to waste by default in the absence of the optical switch. Both of these methods gave improved performance, as shown by the plots. The fact that the performance of these two methods crosses, suggests that the triggering of the optical switch was not optimal, and suggests that the active triggering of the optical switch as described in FIGS. 10 and 11 will improve performance.

FIG. 23 shows an example of a pneumatic fluidic switch that serves to sort cells or particles in a 1×2 microfluidic channel network, i.e., a network with one main input channel and two output channels extending from the bifurcating junction. A "Y" geometry for the bifurcation junction is shown in FIG. 23, but other bifurcations such as a "T" geometry may also be used. In general these microfluidic channels are produced in optically transparent substrates to enable projection of cell detection optics into the channel. This substrate is typically, but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 µm to 100 µm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels.

The flow conditions are set such that pneumatic pressures P0>P1>P2 and cells in fluid flow preferentially from highest pressure to lowest pressure. When pressure P1 is increases such that P0>P2>P1, then fluid flow is perturbed and reestablishes equilibrium when fluid preferentially flows down the opposite branch of the "Y" junction. The system can be returned to its original state by restoring the P0>P1>P2 relationship.

The performance of the sorting mechanism in terms of throughput (the temporal rate of cells entering the sorting region at the top of the bifurcation junction) is limited by the back-propagation of the fluid as shown in FIG. 23. When the fluidic switch is activated, the particle motion is seen to reverse direction and flow upstream before establishing a new flow path. The time delay induced by this motion limits the speed of the switch and the frequency of events to achieve acceptable yield efficiency (the fraction of target cells in the target output channel) and purity (the ratio of the number of target cells to the total number of cells in the target output channel).

FIG. 24 shows one embodiment of a two-channel fluidic switch that serves to sort cells in a 1×2 microfluidic channel network, i.e. a network with one main input channel and two output channels extending from a bifurcation junction. A "Y"

geometry for the bifurcation junction is shown in FIG. 24, but other bifurcations such as a "T" geometry may also be used. A pair of lateral flow channels are positioned between an analysis region and the bifurcation junction. The lateral flow channels may be symmetric in dimension or one side may be larger than the other to support faster switching in one direction. In general these microfluidic channels are produced in optically transparent substrates to enable projection of cell detection optics into the channel. This substrate is typically, but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 μm to 100 μm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels.

The flow conditions are set such that when the fluidic switch, in this case from pneumatic pressure, is turned off so that the pressures P3=P4 in the junction region, all cells will preferentially flow into one of the output channels, for example the right output channel. When the fluidic switch is turned on changing pressure such that P3>P4, a plug of fluid displaces the flow stream such that the cells in proximity of the fluid plug are directed into the left output channel. The setting and control of the flow conditions in the microfluidic channel network can be achieved by direct drive pumping, pneumatic pumping, electro-kinetics, capillary action, gravity, or other means to generate fluidic flow.

The performance of the sorting mechanism in terms of throughput (the temporal rate of cells entering the sorting region at the top of the bifurcation junction), yield efficiency (the fraction of target cells in the target output channel, 12), and purity (the ratio of the number of target cells to the total number of cells in the target output channel, 12), are impacted by various factors, each of which affects the implementation of the optical switch. The fluidic switch can be characterized by several parameters such as the pressure differential (P4 vs. P3) projected into the sorting junction region of the microfluidic channel network, the position of the switching channels with respect to the bifurcation junction, the duration of activation of the fluidic switch, the maximum pressure used to produce the fluid displacement, etc. The selection of particular values of these parameters for the fluidic switch is a critical function of, among other things, the topology and geometry of the microfluidic channel system, the flow rates (cell velocities) within the microchannel system, the ability to control the position of cells flowing in the main channel (whether they are flowing in the center of the main channel or off-set to one side), the amount of displacement of the cells necessary to achieve reliable switching, the depth of the channels, the shape of the channels, and the forces produced by the cells' interactions with the optical switch.

Figure 25B:
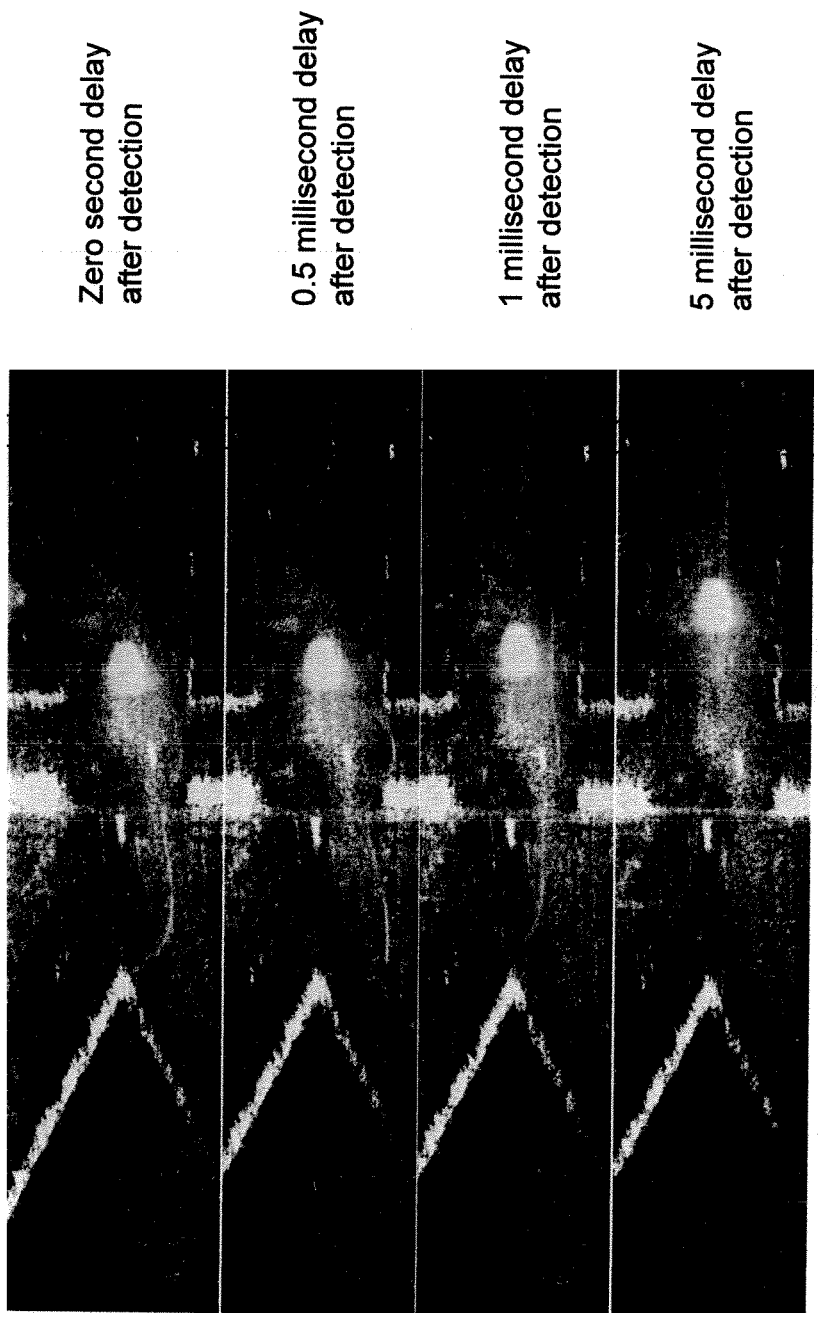

FIG. 25 shows one embodiment of a one-channel fluidic switch that serves to sort cells in a 1×2 microfluidic channel network, i.e. a network with one main input channel and two output channels extending from a bifurcation junction. A "Y" geometry for the bifurcation junction is shown in FIG. 25, but other bifurcations such as a "T" geometry may also be used. A single lateral flow channel may be positioned on either side of the main channel between the analysis region and the bifurcation. In general these microfluidic channels are produced in optically transparent substrates to enable projection of cell detection optics into the channel. This substrate is typically, but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 μm to 100 μm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels.

The flow conditions are set such that when the fluidic switch, in this case from pneumatic pressure, is turned off so that the pressure in the junction region is neutral, all cells will preferentially flow into the output channel on the same side as the lateral channel, in this case for example, the right output channel. When the fluidic switch is turned on changing pressure such that P3>P2, a plug of fluid displaces the flow stream such that the cells in proximity of the fluid plug are directed into the left output channel. The setting and control of the flow conditions in the microfluidic channel network can be achieved by direct drive pumping, pneumatic pumping, electro-kinetics, capillary action, gravity, or other means to generate fluidic flow.

Figure 26:
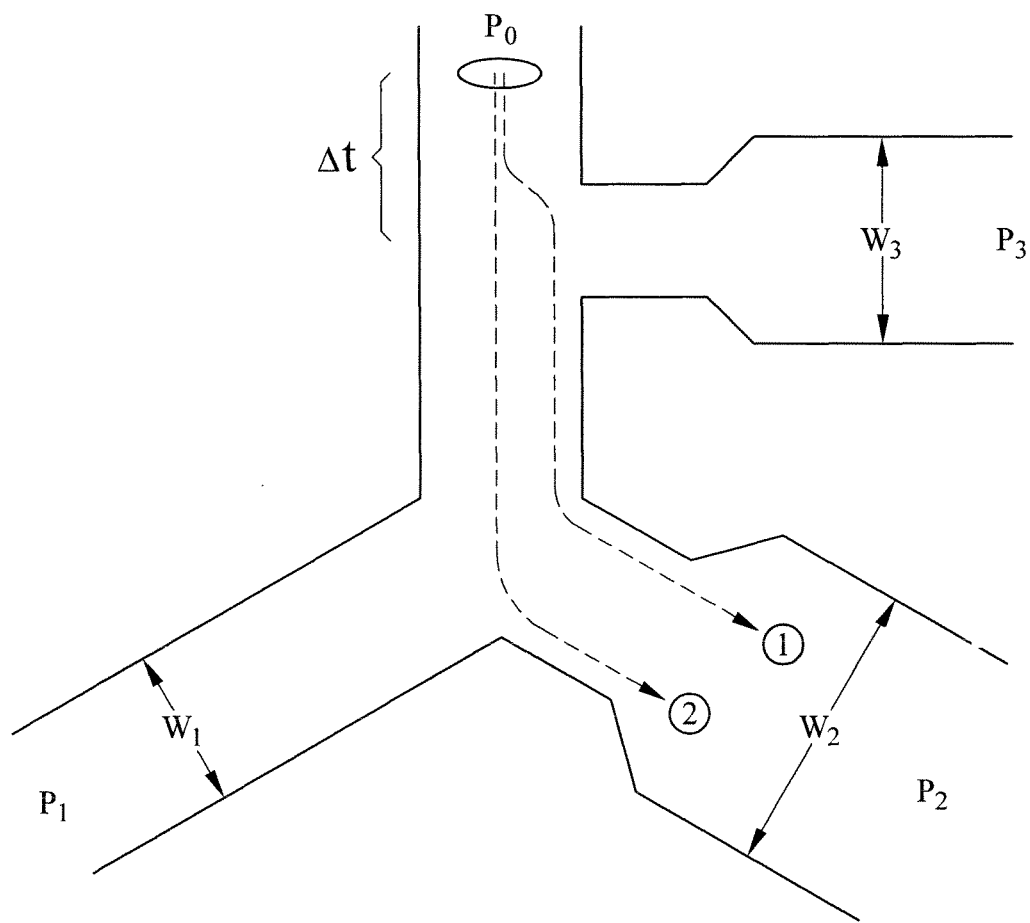
FIG. 26 shows a preferred embodiment of a Y" shaped sorting junction in a microfluidic channel with a one-channel fluid switch.

A preferred embodiment of a one-channel fluidic switch is shown in FIG. 26. An off-set flow is achieved by having the right channel wider than the left channel. The switch channel is also wider than the primary channel along the majority of its path length and tapers at the point of fluid insertion. This lowers the peak amplitude of the applied pneumatic pressure necessary to achieve sorting by concentrating the force on a smaller cross sectional area. This allows for faster operation and improved throughput.

The performance of the sorting mechanism in terms of throughput (the temporal rate of cells entering the sorting region at the top of the bifurcation junction), yield efficiency (the fraction of target cells in the target output channel), and purity (the ratio of the number of target cells to the total number of cells in the target output channel), are impacted by various factors, each of which affects the implementation of the optical switch. The fluidic switch can be characterized by several parameters such as the maximum pressure projected into the sorting junction region of the microfluidic channel network, the position of the switching channels with respect to the bifurcation junction, the duration of activation of the fluidic switch, etc. The selection of particular values of these parameters for the fluidic switch is a critical function of, among other things, the topology and geometry of the microfluidic channel system, the flow rates (cell velocities) within the microchannel system, the ability to control the position of cells flowing in the main channel (whether they are flowing in the center of the main channel or off-set to one side), the amount of displacement of the cells necessary to achieve reliable switching, the depth of the channels, and the shape of the channels. For mammalian cells, channels with cross sections of approximately 50 μm×150 μm with pressure drops of 0.5 to 1.0 psi over path lengths of 20-50 mm will achieve flow velocities of 1-5 μL per minute and use of switching pressures of 1-3 psi is sufficient to achieve switching rates of hundreds of events per second. For general application to particles of 100 nm to 100 μm, typical pressure drops for sample and sheath flow are in the range of 0.1 to 10 psi over path lengths of 10 to 100 mm. A ratio of 2:1 for sheath to target pressures is selected with the current chip design to ensure appropriate pinch of the sample stream. Channel cross sections can be made in the range of 5 to 150 μm deep by 10 to 1,000 μm wide, depending on the type of cell or particle being run through the chip.

Figure 27:
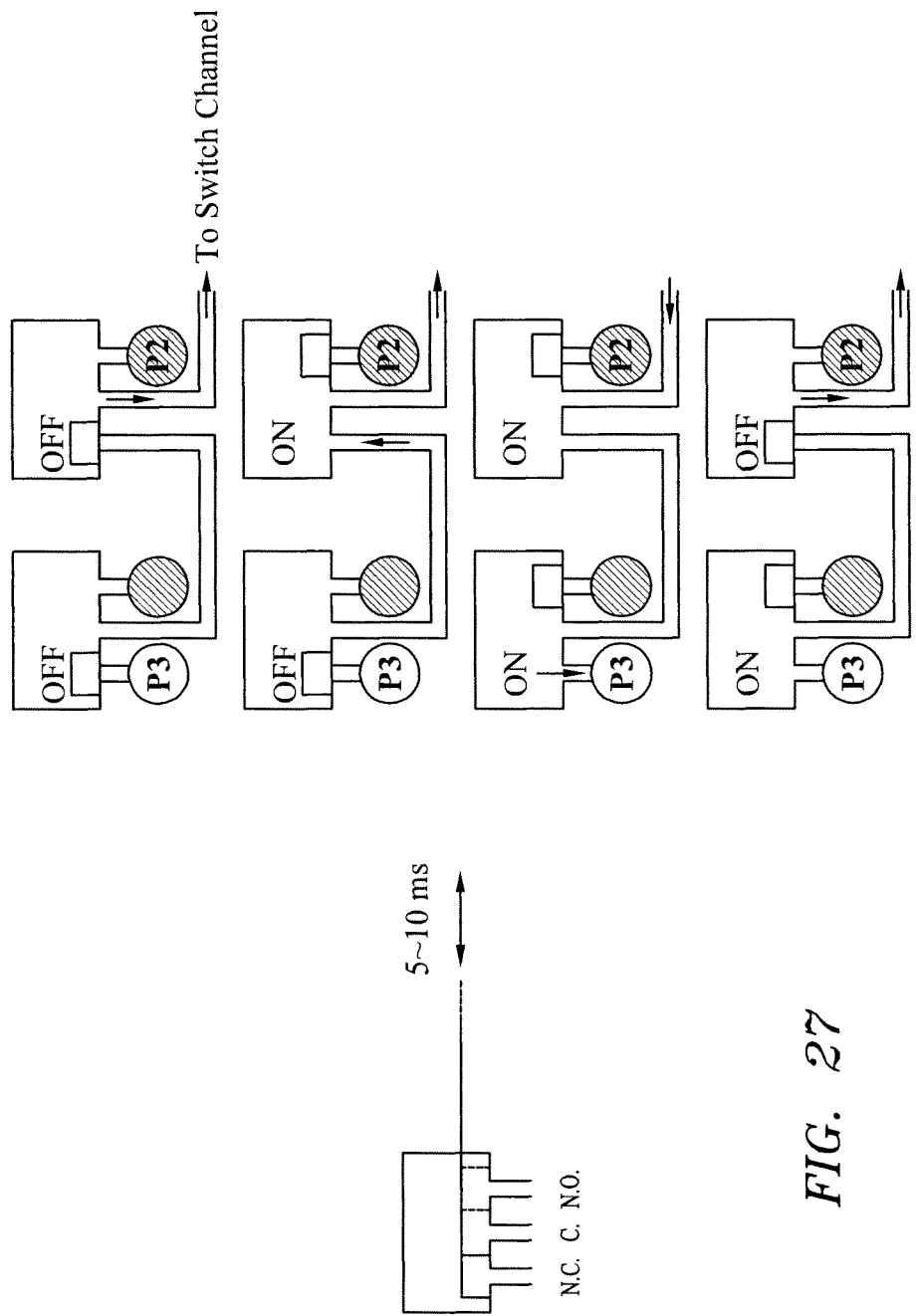
FIG. 27 shows a coupling of two switching valves to minimize pneumatic switching response time and control the pneumatic profile in a one-channel fluid switch.

FIG. 27 shows a two-valve switch configuration that allows control over the maximum pressure, rise time, decay time and total time of a pneumatic pressure pulse to actuate the fluidic switch. Three ports may be connected to pneumatic pressure sources, ambient air, or vacuum. For rapid switching, P1 is held at a high pressure greater than ambient air and P2 and P3 are at ambient air. In the neutral position, both valves are closed or off. When a switching event is desired, the first valve opens, which applied pneumatic pressure to the switch channel. A second valve opens after a brief delay (e.g., less than 5-10 milliseconds), which rapidly bleeds the excess pressure from P1 out of port P3. The first valve is closed to bleed the remaining pressure in the switch channel to ambient levels and then the second valve closes to return the system to its neutral position. This allows the pneumatic pulse to be shorter than the off-on-off cycle time of a single valve (e.g., approximately 5 to 10 milliseconds). Selecting a pressure P1 that is several times greater than the maximum pressure desired (e.g., 8 psi for a pulse with a desired 2 psi peak) combined with ambient air or vacuum at ports P2 and P3, the pneumatic pressure pulse may be shaped for maximum performance of the fluidic switch.

Figures 28A, 28B:
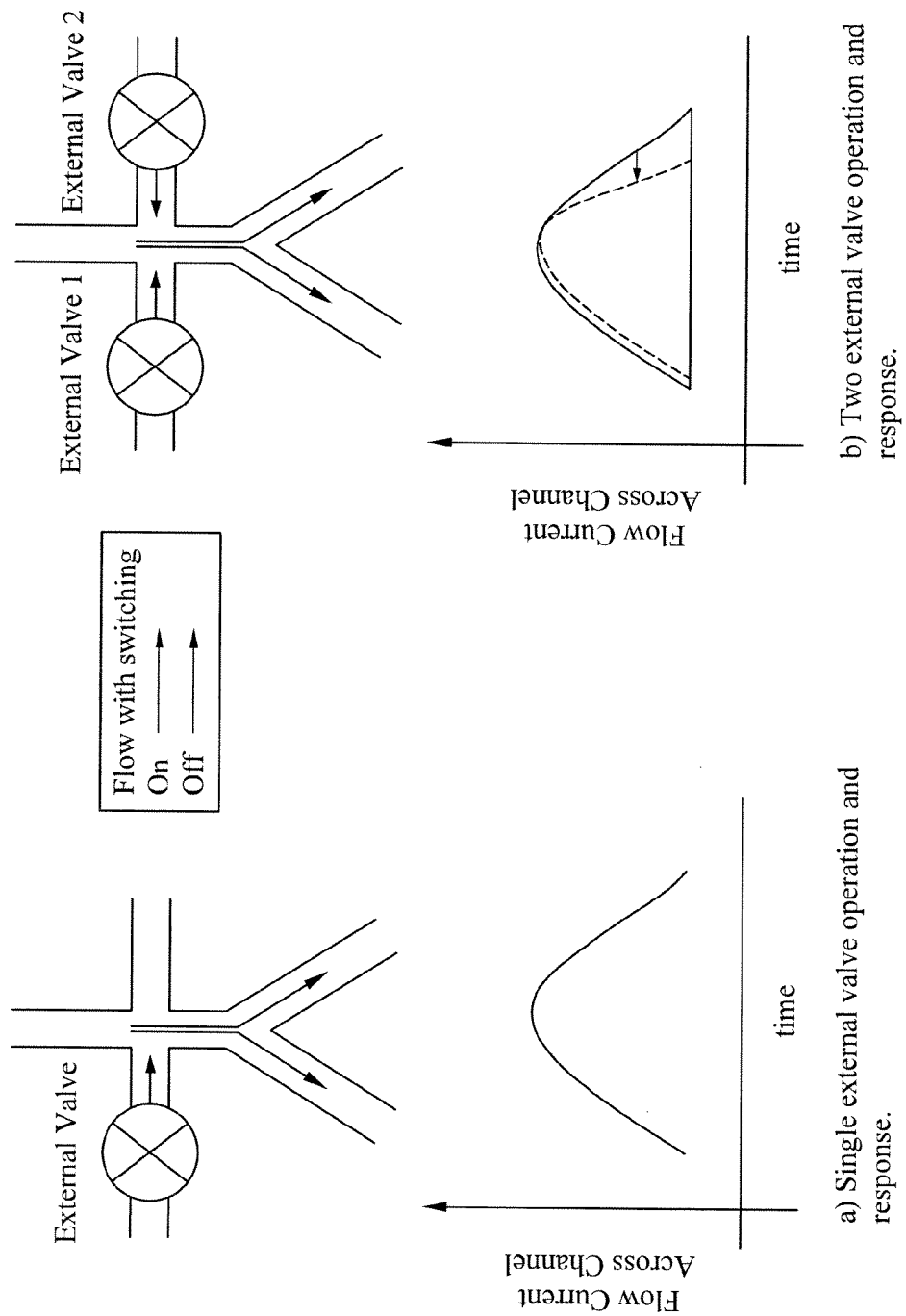
FIGS. 28a and 28b show a coupling of two switching valves and graphs of flow current across channel as a function of time to minimize pneumatic switching response time and control the pneumatic profile in a two-channel fluid switch.
Figure 29:
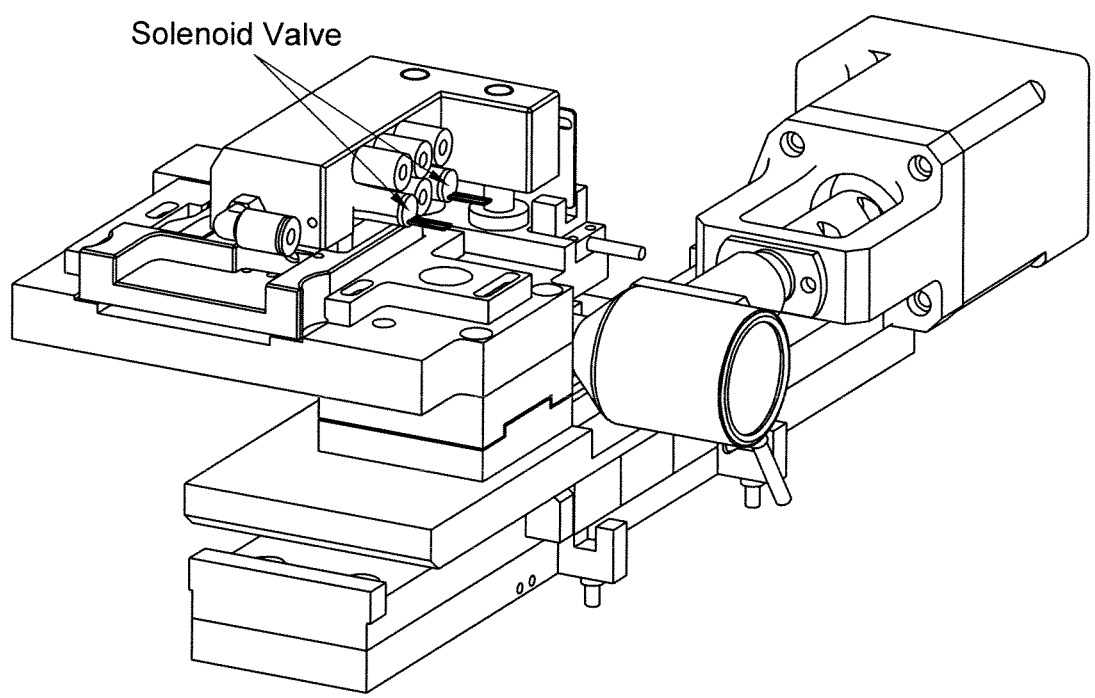
FIG. 29 is a cartridge holder for pneumatic control of microfluidic chips.

FIG. 28 shows two valve configurations for the two-channel fluidic switch in FIG. 24. In the first, a single valve modulates a high pressure source, and the second channel is at ambient air. In this configuration, the shortest possible pulse is determined by the off-on-off cycle time of the valve (e.g., 5-10 milliseconds). In the second configuration, a valve is placed on each lateral channel of the fluidic switch. In this case, both valves may be used to modulate external pressure sources. The second valve may be opened after the first valve with a variable time delay that is shorter than the off-on-off cycle time of the valves. In this way, the pneumatic pressure pulse may be shortened to increase the speed and performance of the fluidic switch.

Figure 30:
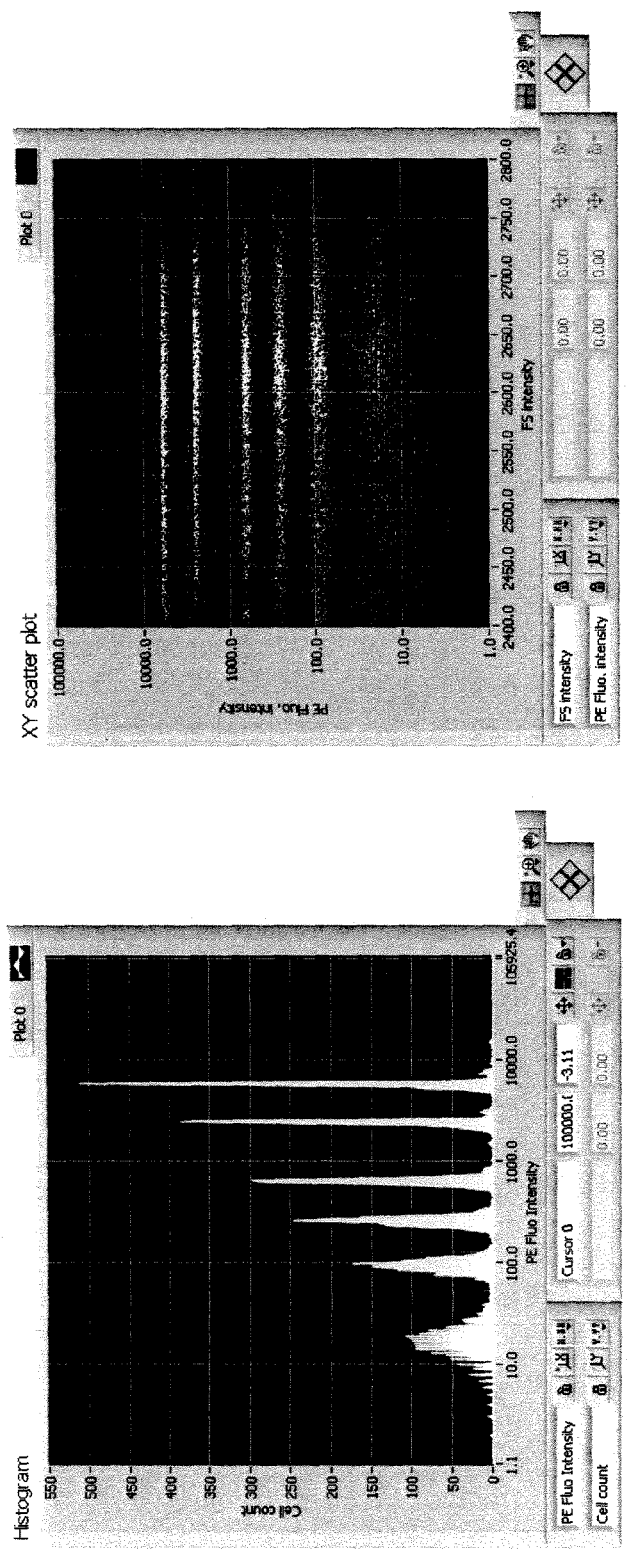
FIG. 30 shows a measurement of fluorescent calibration beads performed on the instrument described herein.
Figure 31A:
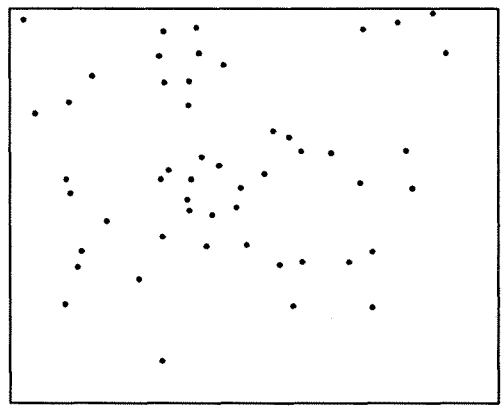
FIG. 31a shows a fluoresence microscope image of DAP1-stained Jurkat cells and FIG. 31b shows a fluorescence microscope image of target Jurkat cells with CellTracker Green.
Figure 31B:
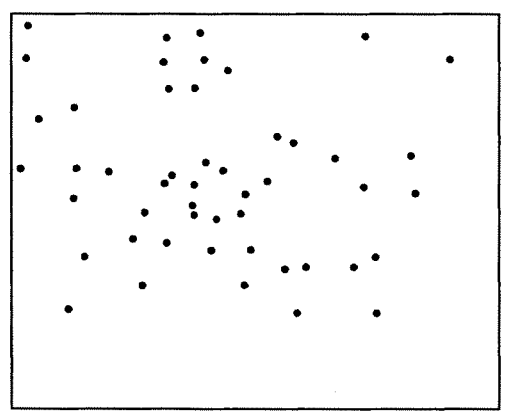

A complete fluidic switch-based cell sorting instrument has been constructed. Examples of measurements obtained using this instrument are shown in FIGS. 30-31. In FIG. 31, fluorescent calibration beads (e.g., Spherotech SPHERO beads or BD Quantibrite beads) were measured and show clear separation of six intensities. Statistics of mean intensity, standard deviations and CV's are consistent with the manufacturers' recommended values. FIG. 31 shows an example of sorting a cell population. In this example, a target population of 1% Jurkat cells stained with CellTracker™ Green (Invitrogen Corp.) were spiked into an unstained population of Jurkat cells. The cells were sorted using a pressure of 0.3 psi for the sample, 0.6 psi for the sheath buffer, and 1.5 psi for the switching valve. Approximately 35 thousand cells were analyzed and 336 target cells were identified and sorted into the target well. Inspection of the target reservoir found 331 target cells out of a total of 369 cells. This results in a calculated recovery of 99% and purity of 90%.

Figure 32:
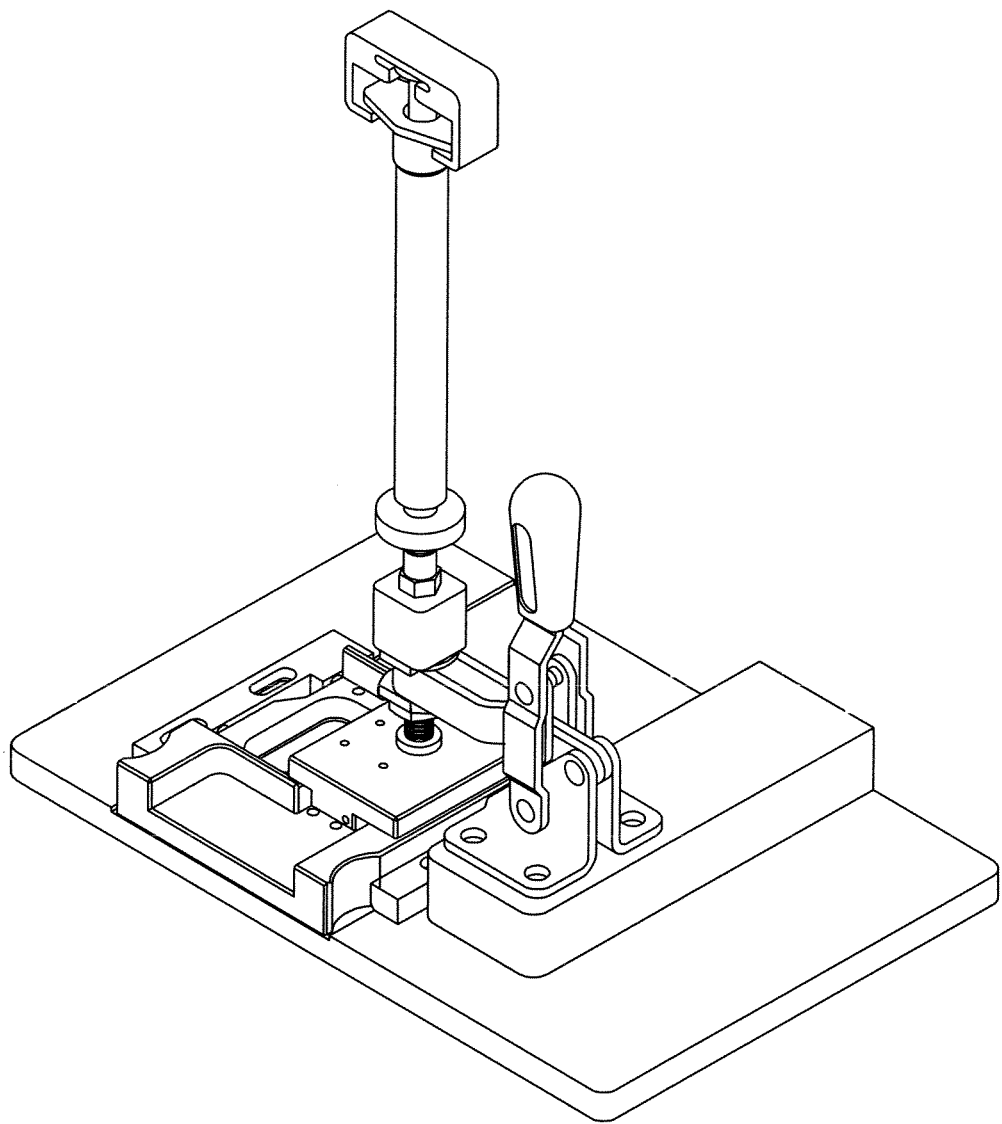
FIG. 32 shows a microfluidic cartridge priming station. The invention describes of priming station for priming of microfluidic devices.

To operate microfluidic chips, an initial fluid priming of all microfluidic channels is required in a manner that does not trap bubbles or introduce dust particles, which impede flow. This requires application of a reproduceable volume of air at a steady pneumatic pressure from a clean high pressurized air source. Generally, dust-free systems like a clean bench or a laminar hood are necessary for priming microfluidic devices. The device, a priming station, shown in FIG. 32 satisfies those requirements in a simple and economical way. A clamp on the priming station physically holds a cartridge and provides sealing for high pressure access. A small sub-micron pore filter is attached to the clamp to supply high pressure air to a fluid filled reservoir without dust. A removeable syringe may be used to provide a controllable volume of air or an automated valve connected to a high pressure source may be used. This uniformly distributes a predetermined volumed of bubble-free fluid throughout the microfluidic channels.

FIG. 33 shows a method for dilition cloning of cells for monitoring growth and separating clonal populations. Microwells with a volume of a few nanoliters may be microfabricated using a variety of materials, including but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 μm to 100 μm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels. An example of an array of nanowells is shown in FIG. 33. In this case, the wells are 100 μm×100 μm squares with a depth of 70 μm and fabricated using PDMS soft lithography. The wells are sterilized in a plasma and inserted into a 24-well tissue culture plate. Cells in suspended in media are loaded into each well and settle by gravity into the nanowells where they may be monitored periodically to observe growth kinetics or to harvest preferred clonal colonies at a single time point. These wells also may be incorporated into the output reservoirs of a sorting device as a fixed element or as a removeable insert.

Figure 35:
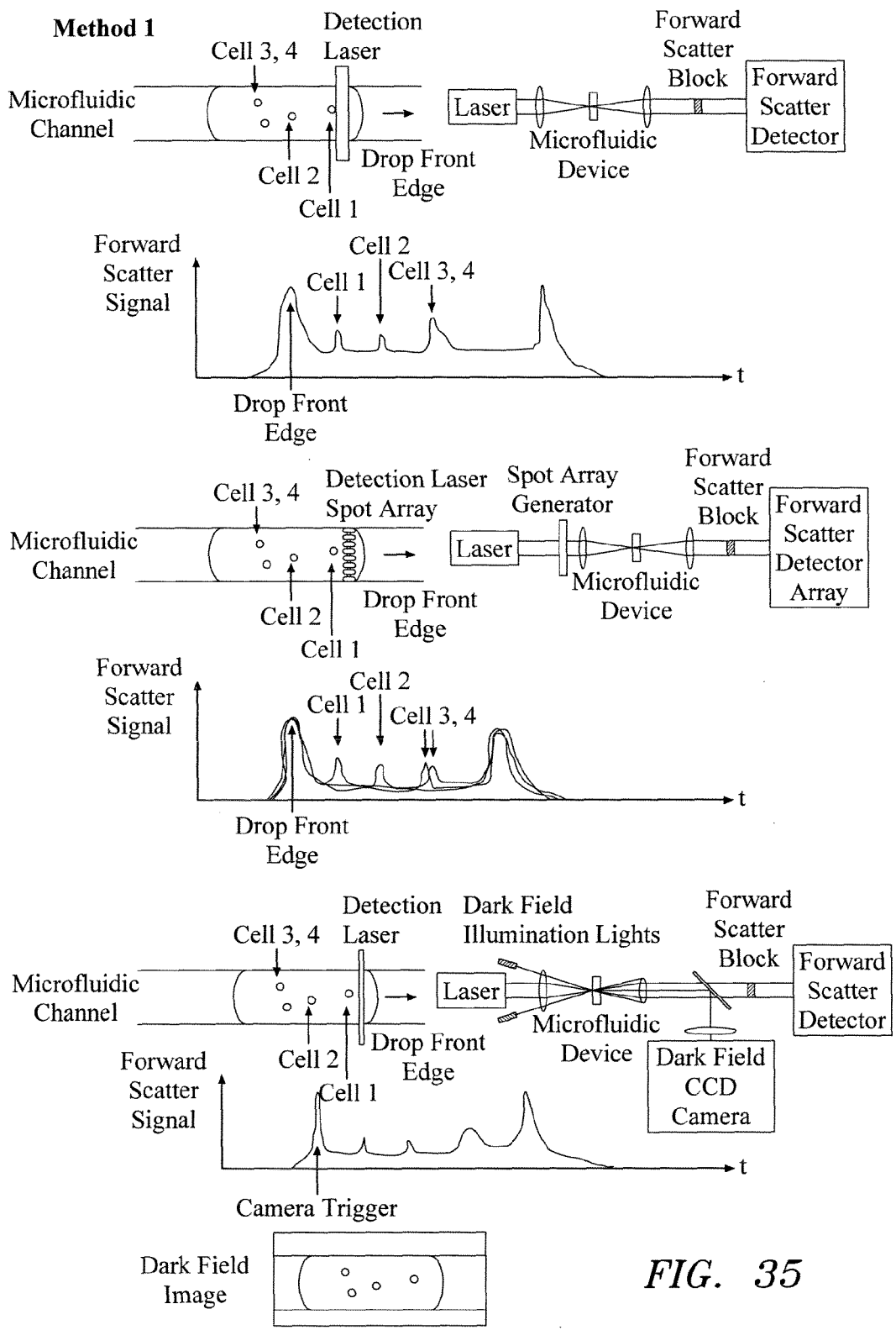
FIG. 35 shows cell/particle detection inside multi-phase microfluidic drops. The invention describes several detection methods for cell/particle counting inside multi-phase microfluidic drops.

FIG. 35 shows optical detection methods for cell/particle counting inside a multi-phase microfluidic drop (for example, cells/particles encapsulated in drops inside a microfluidic channel). By applying suitable signal processing, the numbers of cells/particles inside the drops can be detected based on signal peaks from the cells/particles. In one method, the entire channel is illuminated and a single detector measures a signal, such as forward scatter, that indicates the presence or absence of a cell in the drop. A more sophisticated detection uses an array of forward scatter detectors arranged across the channel and orthogonal to the direction of flow in order to provide a better spatial resolution for counting and localizing the cells/particles inside the drops. In yet another approach, dark field illumination and imaging can be added to a single detector scatter measurement. When forward scatter signal detects the front edge of the drops, a CCD camera can be synchronized to take a dark field image of the drops. The cells/particles will be bright spots in the images, which can be processed and identified for counting.

In many sorting situations, the target population of cells or particles may be small, but the surface area of the collection reservoir is large. Particles may stick to the reservoir wall, which reduces collection efficiency. FIG. 36 shows approaches to minimizing the cell or particle interaction with surfaces. In one method, sorted target cells are collected in a confined area that displaces less volume than the fluid to minimize contact between cells and collection reservoir walls. Due to surface tension, collected liquid forms a drop wetted on the confined area. In another method, the surface of the collection reservoir can made hydrophobic by coating with a hydrocarbon or fluorocarbon-based silanization. Because of the hydrophobic coating, the collected liquid with cells or particles will be confined in a drop near outlet holes. In another method, a separate, fitted but removable container can be used for collection of sorted cells. This separate container can be used for further treatment of cells, which will minimize loss of cells while transferring sorted cells from collection reservoir to another reservoir (a multi-well culture plate, for example). The collection container has a hole on the bottom to access to the outlet hole in microfluidic devices.

The diameter of the hole may be made less than one millimeter so that surface tension prevents leaking through it. A gasket made of soft material (for example, Silicone-based rubber, PDMS) is inserted between the collection container and the microfluidic device for sealing and bonding.

Often it is desired to recover samples after cytometric analysis. FIG. 38 shows a microfluidic device that pinches cell flow for analysis but recovers cells with less dilution. The sample is flow focused using a sheath buffer, as shown in FIG. 2 and FIG. 38. After the sample passes the analysis region, the microfluidic channel splits into three channels. The center channel is the sample recovery channel, and the channels to the left and right collect the excess sheath buffer to reduce sample dilution. By appropriate selection of channel widths and applied pressures, the degree of sample dilutions may be adjusted from 1:1 dilution to the dilution of the sheath flow (typically 1:20). Under some conditions, i.e., very dilute samples, the collected specimen may be concentrated instead.

Figure 37:
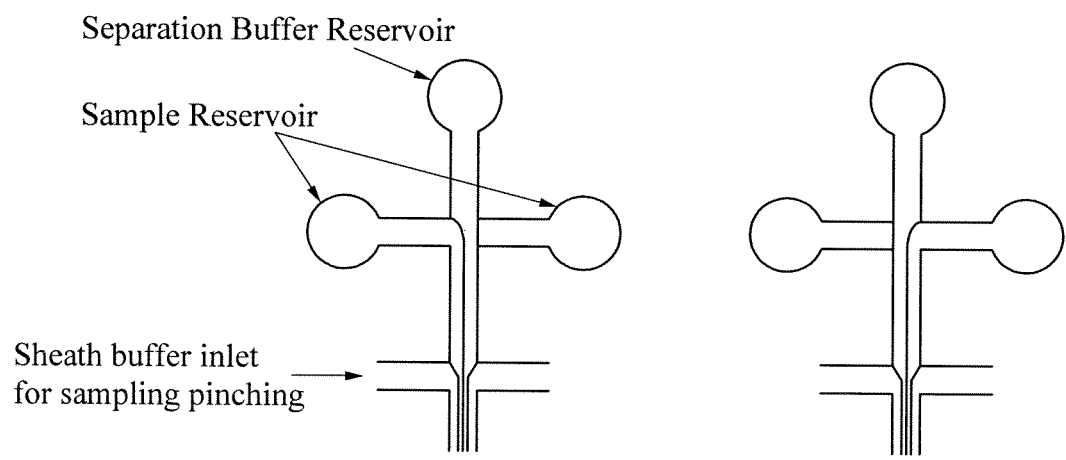
FIG. 37 is a microfluidic device for multiple sample analysis or sorting. The invention describes several microfluidic devices for multiple sample analysis or sorting.

FIG. 37 shows a microfluidic device design for multiple sample analysis or sorting. This design does not require changing cartridges or realignment after loading different samples that may cause changes in the fluorescent background. This invention includes three sample reservoirs two for samples and one for a buffer to separate the two samples from cross contamination. By adjusting pressure, each sample can be injected and pinched for flow cytometric analysis. For example, with two samples A and B, for an analysis of A the reservoir of sample A is applied with highest pressure and the buffer reservoir is at an intermediate pressure while the reservoir of sample B is kept at the lowest pressure. By alternating which channel has the highest pressure, the desired channel will flow to the analysis region (highest pressure) or it will be inhibited from flowing (lowest pressure). Pure buffer may be introduced between each sample to allow clear separation of signals in the analysis region. The number of samples that can be loaded and run sequentially can be increased by two for each independent separation buffer channel added to the microfluidic chip.

FIG. 38 also shows an example of a microfluidic device that can multiplex two samples with adjustable dilution. This device utilizes two sample channels, A and B, and a separation buffer. To analyze sample A, the following pressure setting is used, P_sw_A<P_sw_B<P_B<P_sb<P_A<P_sth. To analyze sample B, the following pressure setting is used, P_sw_B<P_sw_A<P_A<P_sb<P_B<P_sth. To prevent cross contamination between samples, a separation buffer may be flown down the channel in between measurements of Samples A and B. With additional pressure ports, this design is scalable to three or more samples. FIG. 38 shows an example of this device switching between two samples.

Although the foregoing invention has been described in some detail by way of illustration and example for purposes of clarity and understanding, it will be readily apparent to those of ordinary skill in the art, in light of the teachings of this invention, that certain changes and modifications may be made thereto without departing from the spirit or scope of the invention.

ENDNOTES

1. H. M. Shapiro, *Practical flow cytometry*, Wiley-Liss, New York, 2003.
2. Y. Fu, C. Spence, A. Scherer, F. H. Arnold and S. R. A. Quake, "Microfabricated fluorescence-activated cell sorter," *Nat. Biotechnol.* 17, pp. 1109-1111, 1999.
3. Y. Fu, H.-P. Chou, C. Spence, F. H. Arnold, and S. R. Quake, "An integrated microfabricated cell sorter," *Anal. Chem.* 74, pp. 2451-2457, 2002.
4. Wolff, I. R. Perch-Nielsen, U. D. Larsen, P. Friis, G. Goranovic, C. R. Poulsen, J. P. Kutter and P. Telleman, "Integrating advanced functionality in a microfabricated high-throughput fluorescent-activated cell sorter," *Lab Chip* 3, pp. 22-27, 2003
5. Li, P. C. H. & Harrison, D. J. Transport, manipulation, and reaction of biological cells on-chip using electrokinetic effects. *Anal. Chem.* 69, 1564-1568 (1997).
6. Dittrich, P. S. & Schwille, P. An integrated microfluidic system for reaction, high-sensitivity detection, and sorting of fluorescent cells and particles. *Anal. Chem.* 75, 5767-5774 (2003).
7. Fiedler, S., Shirley, S. G., Schnelle, T. & Fuhr, G. Dielectrophoretic sorting of particles and cells in a microsystem. *Anal. Chem.* 70, 1909-1915 (1998).
8. Y. Huang, K. L. Ewalt, M. Tirado, R. Haigis, A. Forster, D. Ackley, M. J. Heller, J. P. O'Connell, M. T. Krihak, "Electric manipulation of bioparticles and macromolecules on microfabricated electrodes," *Anal. Chem.* 73, pp. 1549-1559, 2001.
9. M. Durr, J. Kentsch, T. Muller, T. Schnelle and M. Stelzle, "Microdevices for manipulation and accumulation of micro- and nanoparticles by dielectrophoresis," *Electrophoresis* 24, pp. 722-731, 2003.
10. T. N. Buican, M. J. Smyth, H. A. Crissman, G. C. Salzman, C. C. Stewart and J. C. Martin, "Automated single-cell manipulation and sorting by light trapping," *Appl. Opt.* 26, pp. 5311-5316, 1987.

We claim:

1. A cell sorter comprising:
a cell inlet adapted to receive one or more cells in a fluidic medium;
first and second buffer inlets fluidically coupled to the cell inlet to provide buffer solution to the sorter,
a main fluidic channel fluidically coupled to the cell inlet and the first and second buffer inlets,
a first lateral flow channel fluidically coupled to the main fluidic channel, the first lateral flow channel positioned downstream of the first and second fluid buffer inlets,
a second lateral flow channel fluidically coupled to the main fluidic channel, the second lateral flow channel positioned downstream of the first and second fluid buffer inlets,
first and second outputs fluidically coupled to the main fluidic channel, the outputs being located downstream of the first and second lateral flow channels,
a detector adapted to detect cells of a given state and to generate a signal in response thereto, the detector positioned to detect cells at a position upstream of the first and second lateral flow channels,
a pneumatic lateral force switch coupled to the detector and the first and second lateral flow channels, and actuatable in response to the signal to generate a pressure pulse to cause fluid to move within the first and second lateral flow channels, the pneumatic lateral force switch comprising:
a first pneumatic valve connected to the first lateral flow channel,
a second pneumatic valve connected to the second lateral flow channel,
a control system configured to output timed control signals to actuate both the first and second pneumatic valves in a sequential manner characterized in that the first pneumatic valve is closed after the second pneumatic valve is opened and prior to the second valve closing, whereby in response to the signal to generate the pressure pulse, the pneumatic lateral force switch is activated to provide a lateral force on the cell so as to move the cell such that it selectively exits into the first or second outputs.

2. The cell sorter of claim 1 wherein the first and second lateral flow channels are positioned on opposite sides of the main channel, directly opposite each other.

3. The cell sorter of claim 1 wherein the first and second buffer inlets are of the same size.

4. The cell sorter of claim 1 wherein the first and second butler inlets are of different size.

5. The cell sorter of claim 1 wherein the first and second outputs are of the same size.

6. The cell sorter of claim 1 wherein the first and second outputs are of different size.

7. The cell sorter of claim 6 wherein the first output has a larger volumetric fluid flow than the second output.

8. The cell sorter of claim 7 wherein the first output is a waste output.

9. The cell sorter of claim 1 wherein the cell is a biological cell.

10. The cell sorter of claim 1 wherein the cell is a biological particle.

11. The cell sorter of claim 1 wherein the cell is a natural organic particle.

12. The cell sorter of claim 1 wherein the cell is a natural inorganic particle.

13. The cell sorter of claim 1 wherein the cell is a man-made organic particle.

14. The cell sorter of claim 1 wherein the cell is a man-made inorganic particle.

15. The cell sorter of claim 1 wherein the cells have diameters from substantially 100 nm to substantially 100 microns.

16. The cell sorter of claim 1, wherein the first pneumatic valve is connected to a pneumatic pressure source at a pressure that is greater than the maximum desired pressure of the pressure pulse.

17. The cell sorter of claim 1, wherein each of the first and second pneumatic valves have an off-on-off cycle time of about 5-10 milliseconds.

* * * * *